United States Patent
Chae et al.

(10) Patent No.: US 10,647,738 B2
(45) Date of Patent: May 12, 2020

(54) XYLENE-BASED AMPHIPHILIC COMPOUND AND USE THEREOF

(71) Applicant: Industry-University Cooperation Foundation Hanyang University Erica Campus, Gyeonggi-do (KR)

(72) Inventors: Pil Seok Chae, Gyeonggi-do (KR); Kyung Ho Cho, Seoul (KR)

(73) Assignee: Industry-University Cooperation Foundation, Gyeonggi-do (KR)

( * ) Notice: Subject to any disclaimer, the term of this patent is extended or adjusted under 35 U.S.C. 154(b) by 0 days.

(21) Appl. No.: 15/757,005

(22) PCT Filed: Apr. 15, 2016

(86) PCT No.: PCT/KR2016/003929
§ 371 (c)(1),
(2) Date: Mar. 2, 2018

(87) PCT Pub. No.: WO2017/039107
PCT Pub. Date: Mar. 9, 2017

(65) Prior Publication Data
US 2018/0273570 A1 Sep. 27, 2018

(30) Foreign Application Priority Data
Apr. 14, 2016 (KR) .................. 10-2016-0045394

(51) Int. Cl.
| | | |
|---|---|---|
| C07H 15/18 | (2006.01) | |
| G01N 33/68 | (2006.01) | |
| G01N 1/28 | (2006.01) | |
| C07H 1/00 | (2006.01) | |
| G01N 30/00 | (2006.01) | |

(52) U.S. Cl.
CPC ............. *C07H 15/18* (2013.01); *C07H 1/00* (2013.01); *G01N 1/28* (2013.01); *G01N 30/00* (2013.01); *G01N 33/68* (2013.01)

(58) Field of Classification Search
CPC .......... C07H 15/18; G01N 33/68; G01N 1/28; G01N 30/00
USPC ...................................... 536/55.1
See application file for complete search history.

(56) References Cited

U.S. PATENT DOCUMENTS

2009/0270598 A1  10/2009  Gellman et al.

FOREIGN PATENT DOCUMENTS

WO   WO 2014-182710 A1   11/2014

OTHER PUBLICATIONS

Cho et al. (Chem. Asian J. 2014, 9, 632-638).*
Chae, P.S. et al.,, "Maltose-neopentyl Glycol (MNG) Amphiphiles for Solubilization, Stabilization and Crystallization of Membrane Proteins," Nature Methods, 2010 ed., Electronic Publishing, (vol. 7), (Issue. 12), (p. 1003-1008), (Oct. 31, 2010).
Chae, P.S. et al., "Tandem Facial Amphiphiles for Membrane Protein Stabilization," J.Am.Chem.Soc., 2010 ed., Electronic Publishing, (vol. 132), (Issue. 47), (p. 16750-1675), (Nov. 4, 2010).
Chae, P.S. et al., "A New Class of Amphiphiles Bearing Rigid Hydrophobic Groups for Solubilization and Stabilization of Membrane Proteins," Chemistry-A European Journal, 2012 ed., Electronic Publishing, (vol. 18), (Issue. 31), (p. 9485-9490), (Jun. 22, 2012).
Cho, K.H. et al., "Novel Xylene-linked Maltoside Amphiphiles (XMAs) for Membrane Protein Stabilisation," Chemistry-A European Journal, 2015 ed., Electronic Publishing, (vol. 21), (Issue. 28), (p. 10008-10013), (May 26, 2015).
Cho, K.H. et al., "Novel Benzene-centered Maltoside Amphihiles (BMAs) for Membrane Protein Study," 115th General Meeting and Conference of the Korean Chemical Society, Apr. 15, 2015, 2015 ed., Chemical World, (vol. 55), (Issue. 4), (p. P-734), (Apr. 15, 2015).
Newstead, S. et al., "Insights into outer membrane protein crystallisation," Mol Membr Biol., 2010 ed., (vol. 25), (Issue. 8), (p. 631-638).
Newstead, S. et al., "Rationalizing α-helical membrane protein crystallization," Protein Science, 2008 ed., Cold Spring Harbor, (vol. 17), (p. 466-472).

* cited by examiner

*Primary Examiner* — Shaojia A Jiang
(74) *Attorney, Agent, or Firm* — Hammer & Associates, P.C.

(57) ABSTRACT

The present invention relates to a xylene-based amphiphilic compound, a method for preparing the same, and a method for extracting, solubilizing, stabilizing or crystallizing a membrane protein using the same. By using the xylene-based compound according to the present invention, a membrane protein may be stably stored in an aqueous solution for a long time, and may be applied in functional and structural analyses. The structural and functional analysis of the membrane protein is one of the fields of highest interest in biology and chemistry, and the xylene-based compound according to the present invention can be applied in research on protein structure that is closely related to development of a new drug.

13 Claims, 46 Drawing Sheets

[Fig. 1]
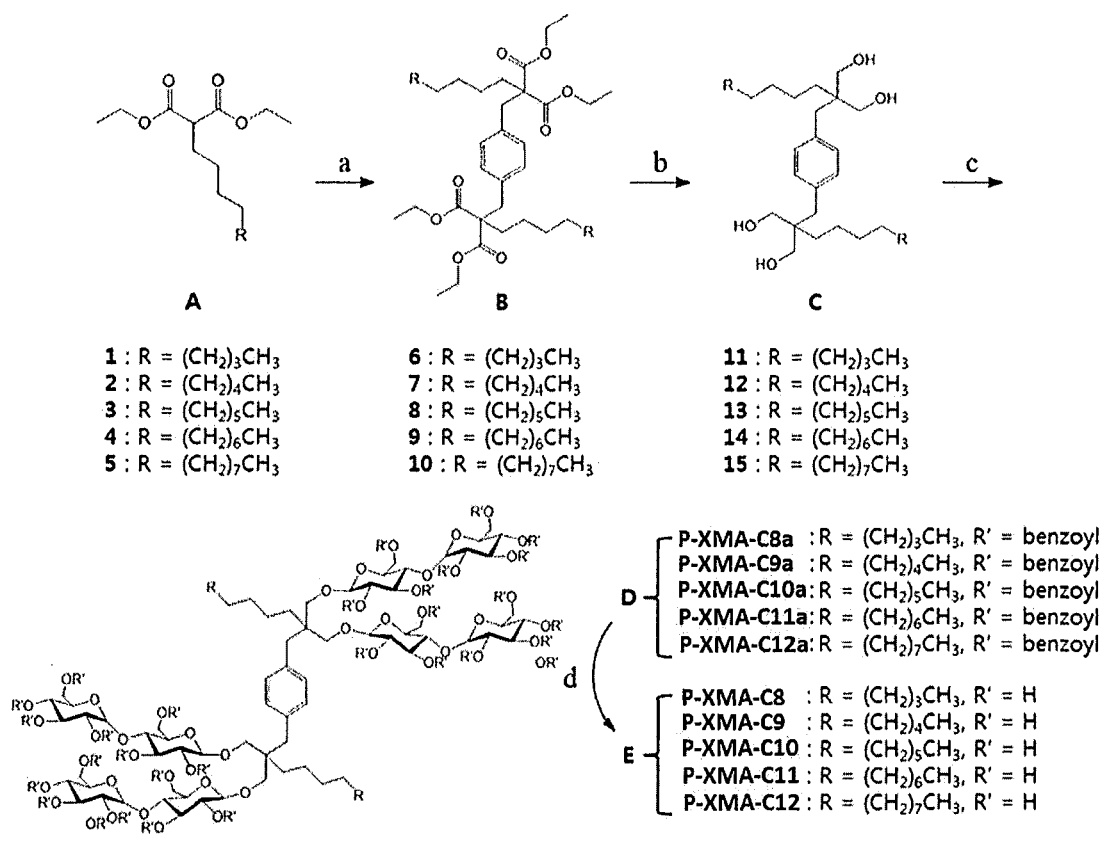
a) NaH, α,α'-Dibromo-p-xylene, THF, DMF, room temperature; (b) LiAlH₄, THF, room temperature; (c) Perbenzeoylate malotsylbromide, AgOTf, CH₂Cl₂, -45°C→ room temperature; (d) NaOMe, MeOH, room temperature.

[Fig. 2]
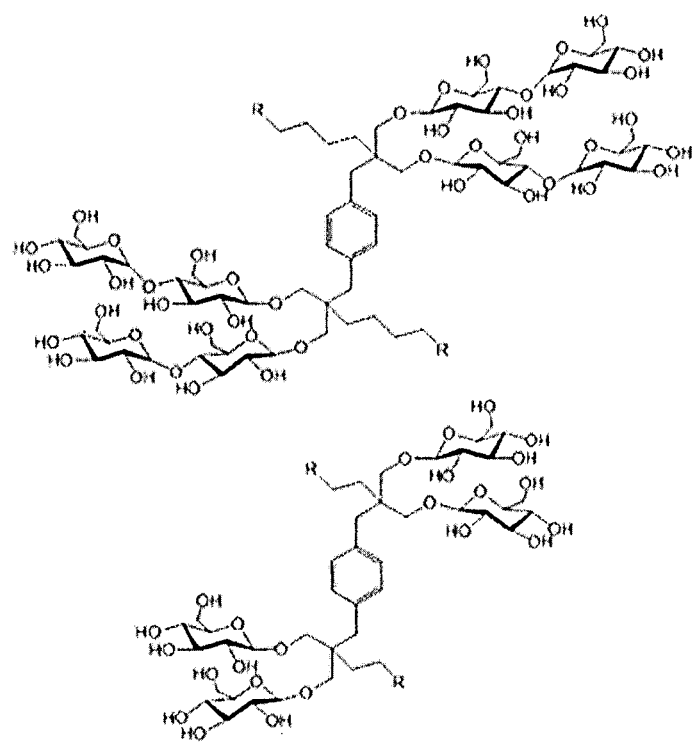
P-XMA-C8 : R = $C_4H_{10}$
P-XMA-C9 : R = $C_5H_{12}$
P-XMA-C10: R = $C_6H_{14}$
P-XMA-C11: R = $C_7H_{16}$
P-XMA-C12: R = $C_8H_{18}$
P-XGA-C4 : R = $C_2H_6$
P-XGA-C5 : R = $C_3H_8$
P-XGA-C6 : R = $C_4H_{10}$

[Fig. 3]
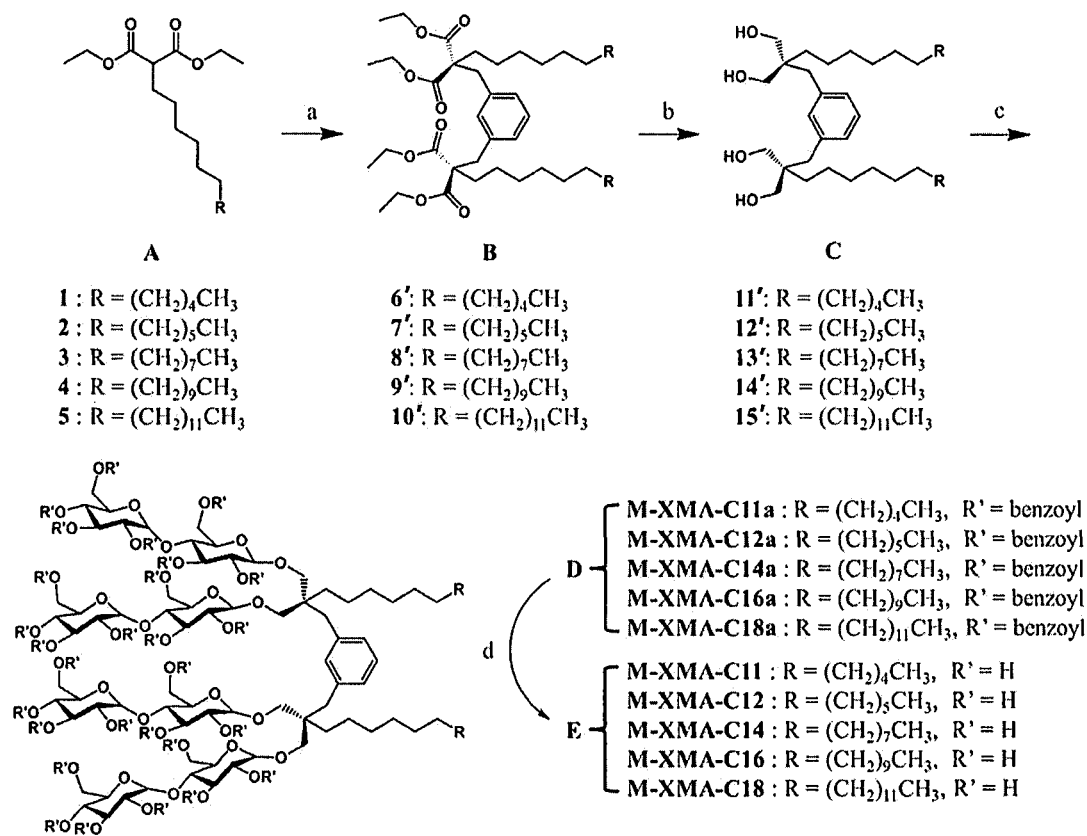
(a) NaH, m-xylylene dibromide, THF, DMF, room temperature; (b) LiAlH₄, THF, room temperature; (c) perbenzoylated maltosylbromide, AgOTf, CH₂Cl₂, -45 °C→room temperature; (d) NaOMe, MeOH, room temperature.

[Fig. 4]
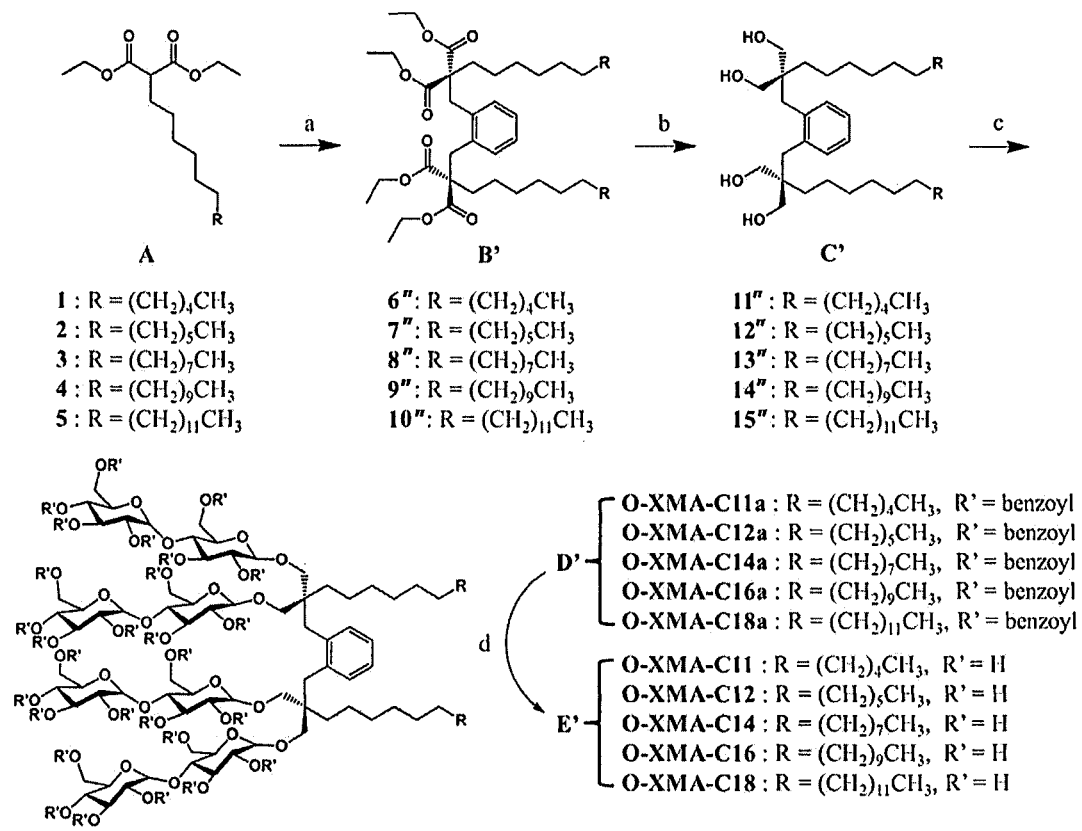
(a) NaH, o-xylylene dibromide, THF, DMF, room temperature; (b) LiAlH₄, THF, room temperature; (c) perbenzoylated maltosylbromide, AgOTf, CH$_2$Cl$_2$, -45 °C→room temperature; (d) NaOMe, MeOH, room temperature.

[Fig. 5]
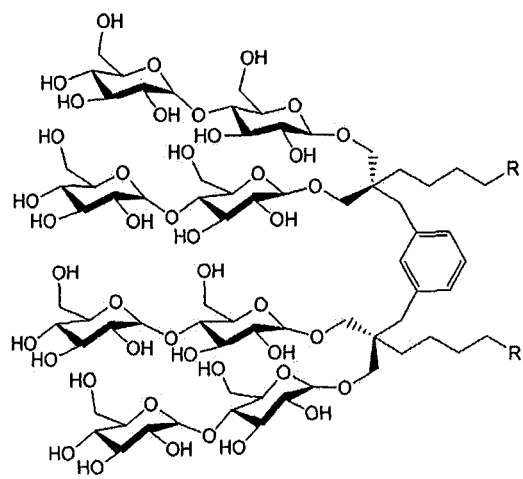
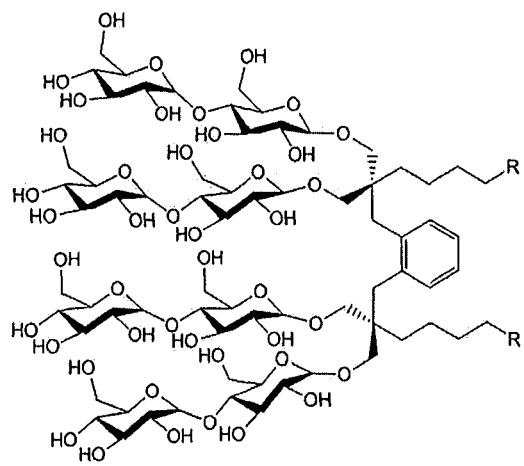
M-XMA-C11 : R = $n$-$C_7H_{15}$
M-XMA-C12 : R = $n$-$C_8H_{17}$
M-XMA-C14 : R = $n$-$C_{10}H_{21}$
M-XMA-C16 : R = $n$-$C_{12}H_{25}$
M-XMA-C18 : R = $n$-$C_{14}H_{29}$
O-XMA-C11 : R = $n$-$C_7H_{15}$
O-XMA-C12 : R = $n$-$C_8H_{17}$
O-XMA-C14 : R = $n$-$C_{10}H_{21}$
O-XMA-C16 : R = $n$-$C_{12}H_{25}$
O-XMA-C18 : R = $n$-$C_{14}H_{29}$

[Fig. 6]
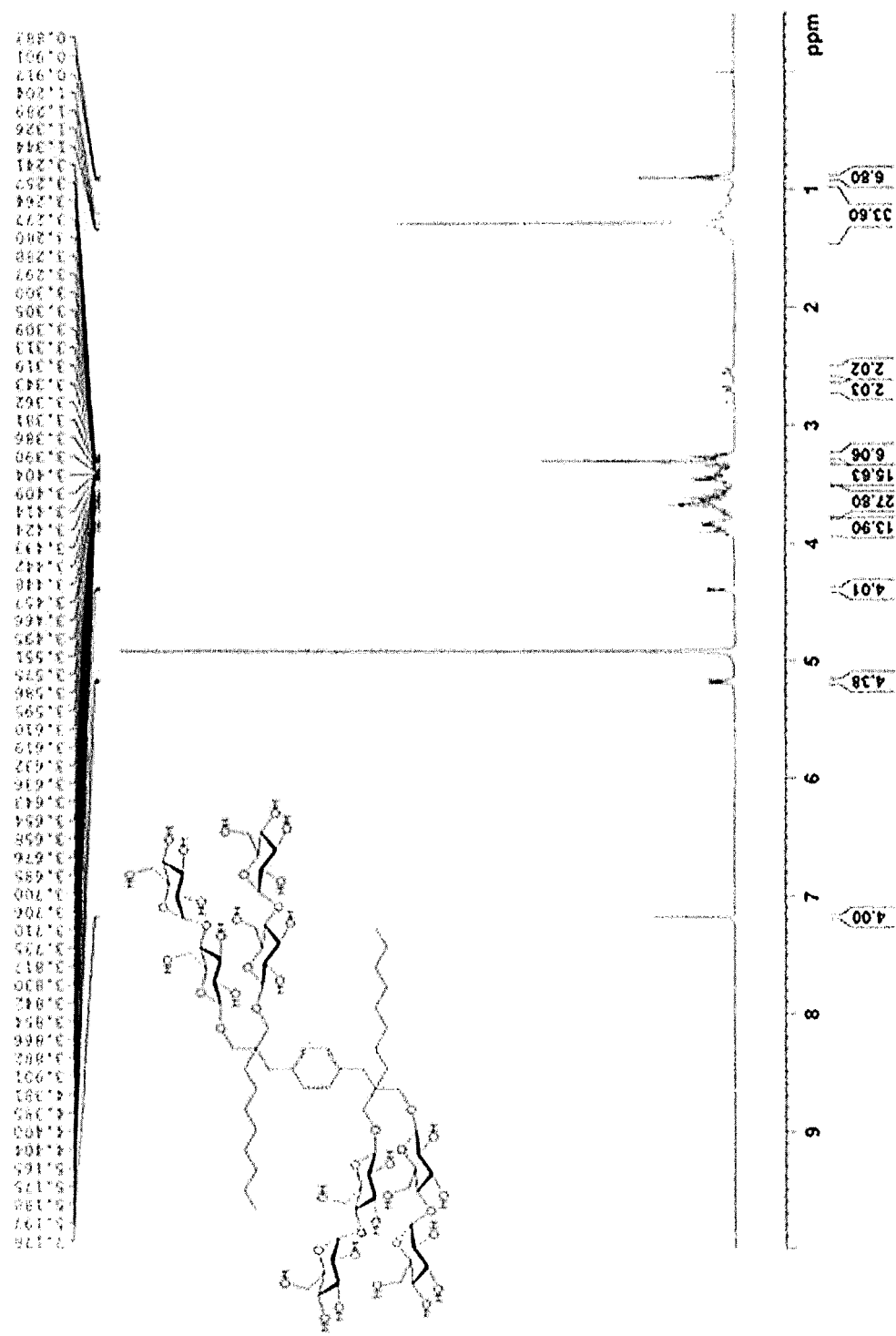

[Fig. 7]
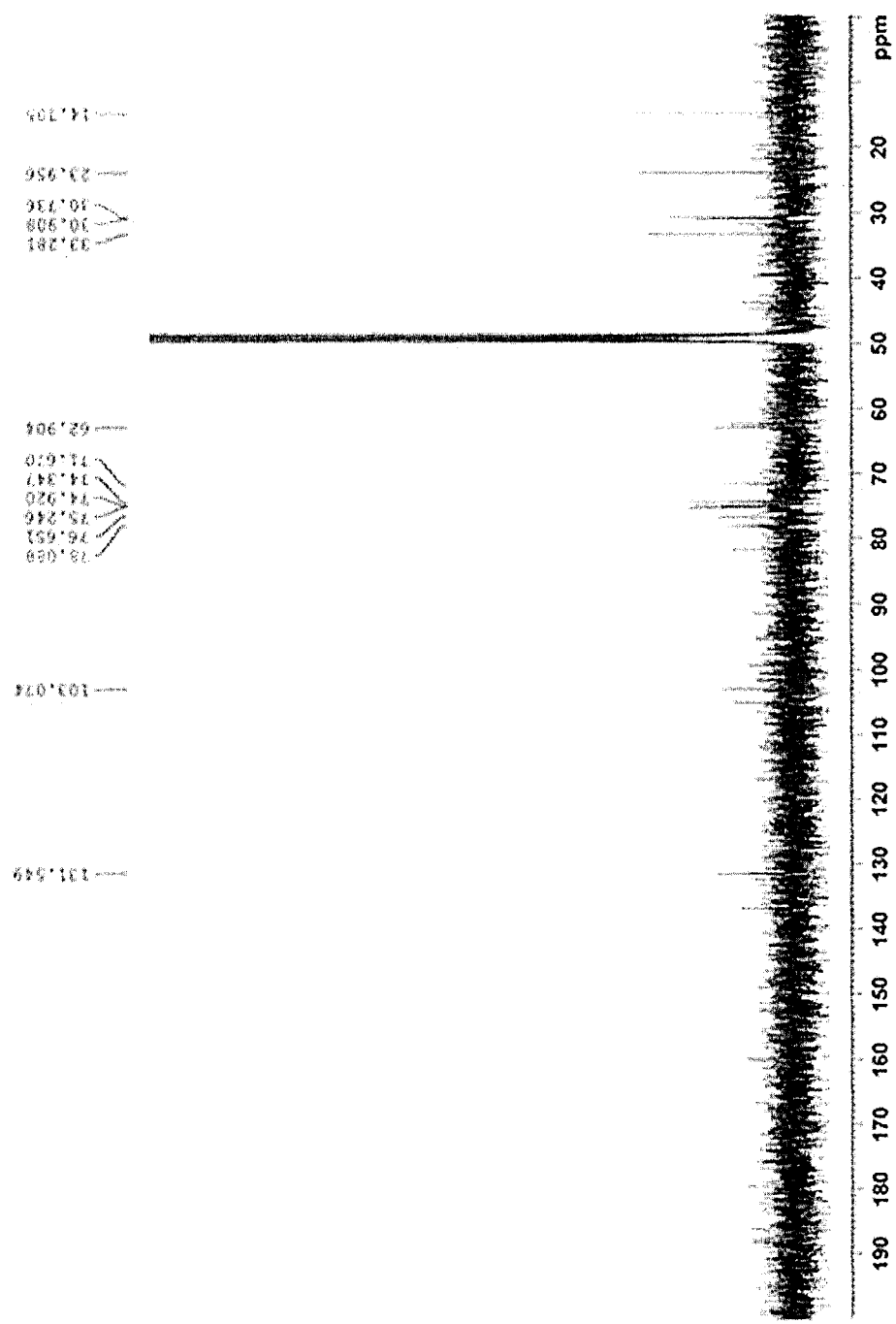

[Fig. 8]
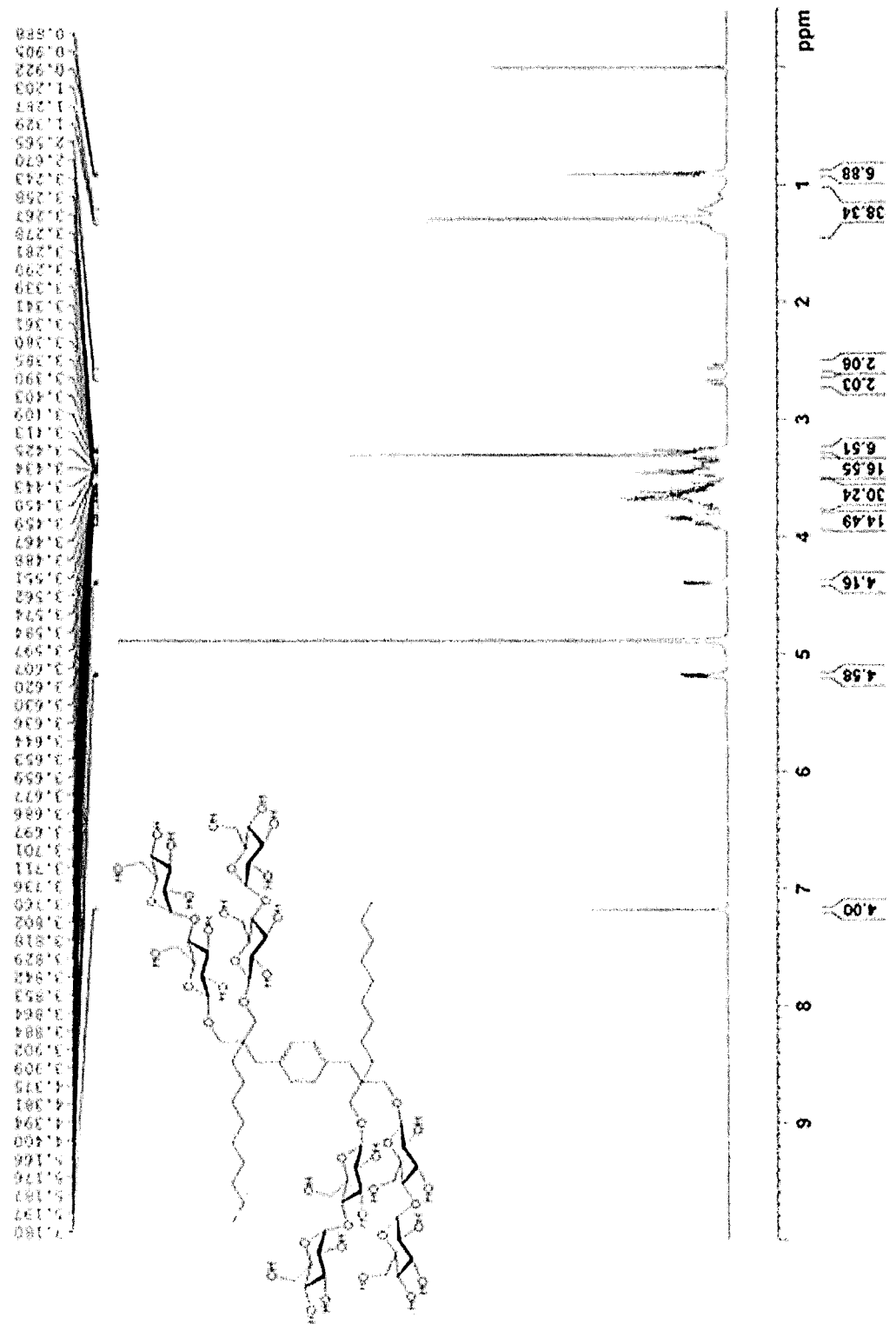

[Fig. 9]
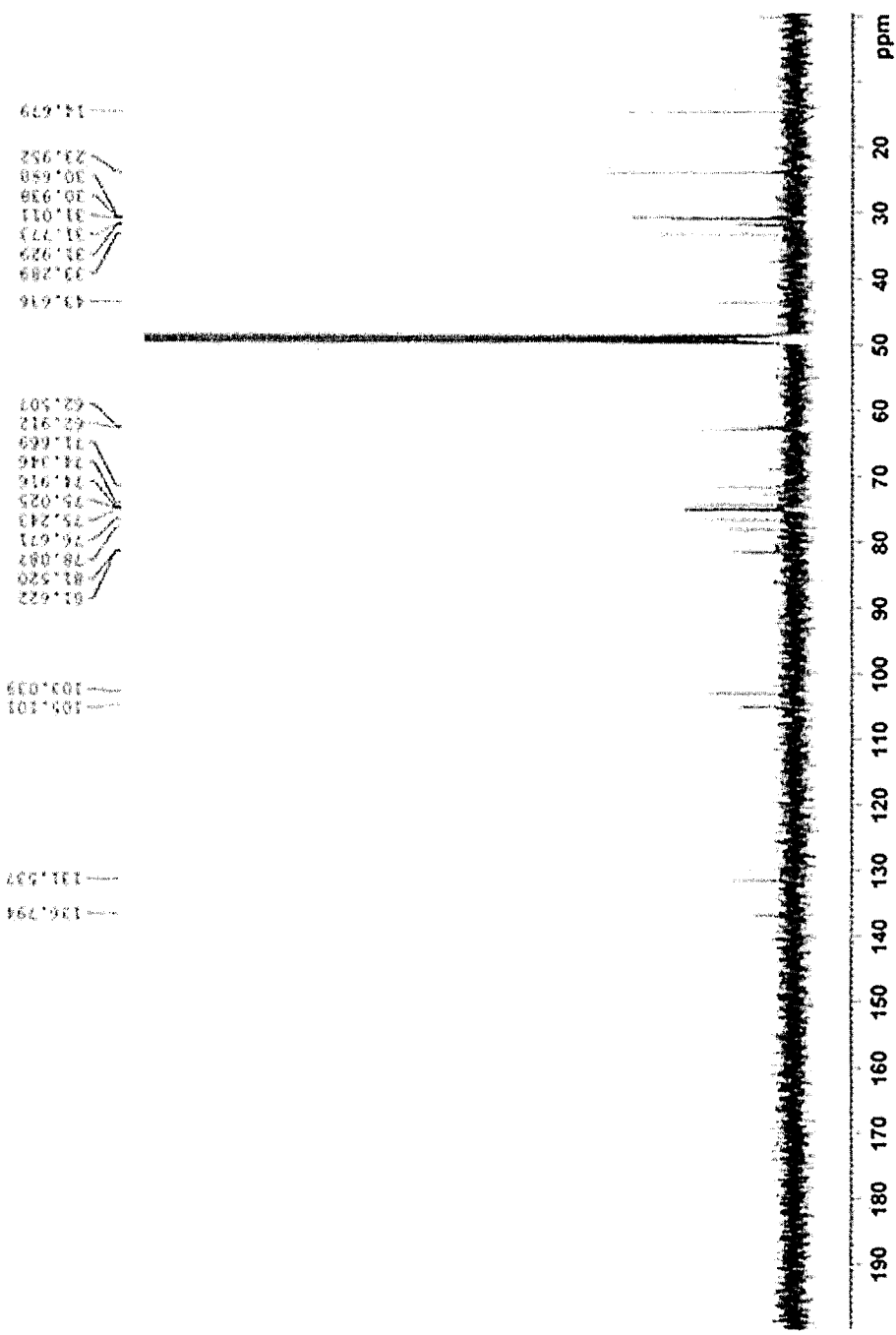

[Fig. 10]
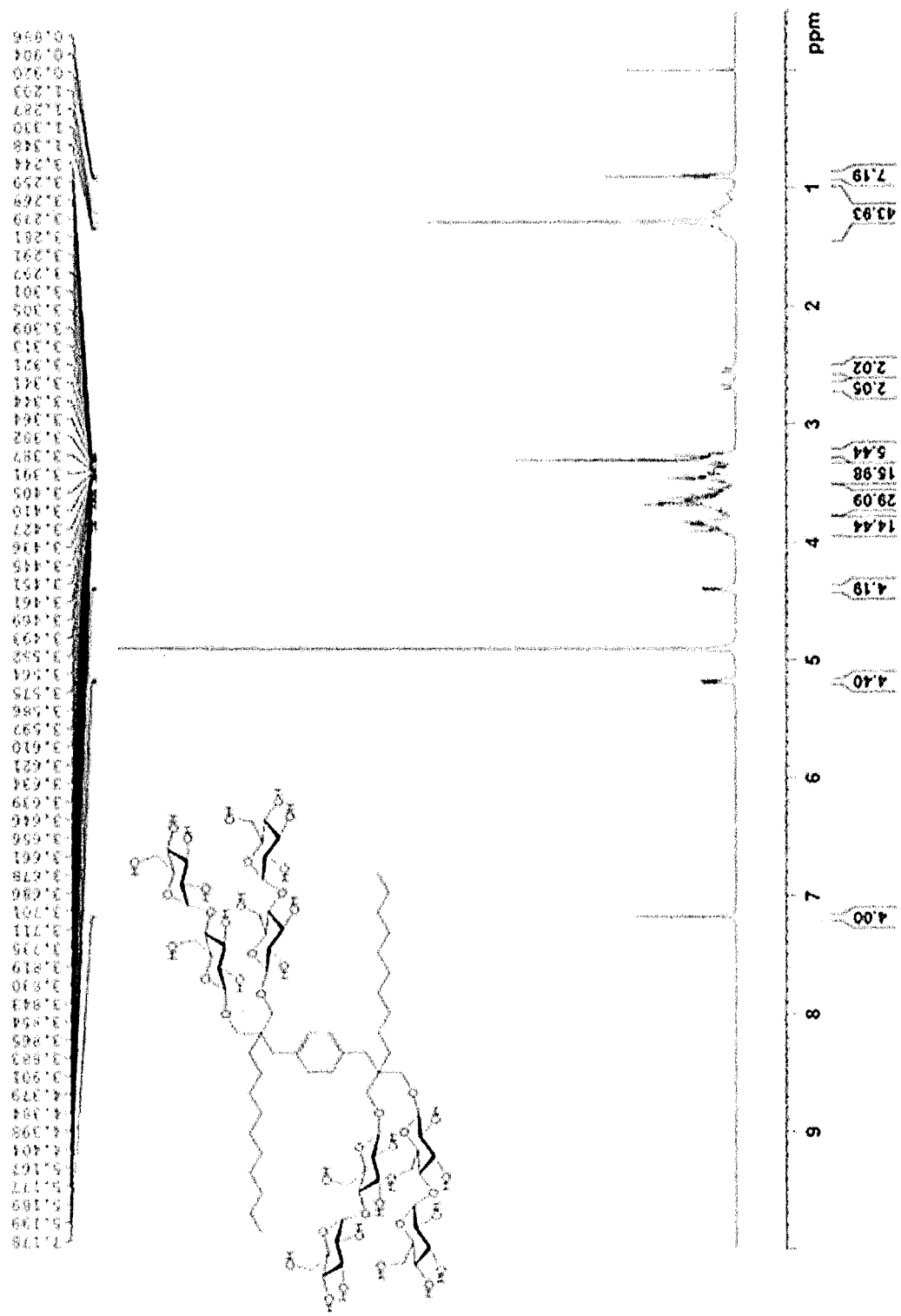

[Fig. 11]
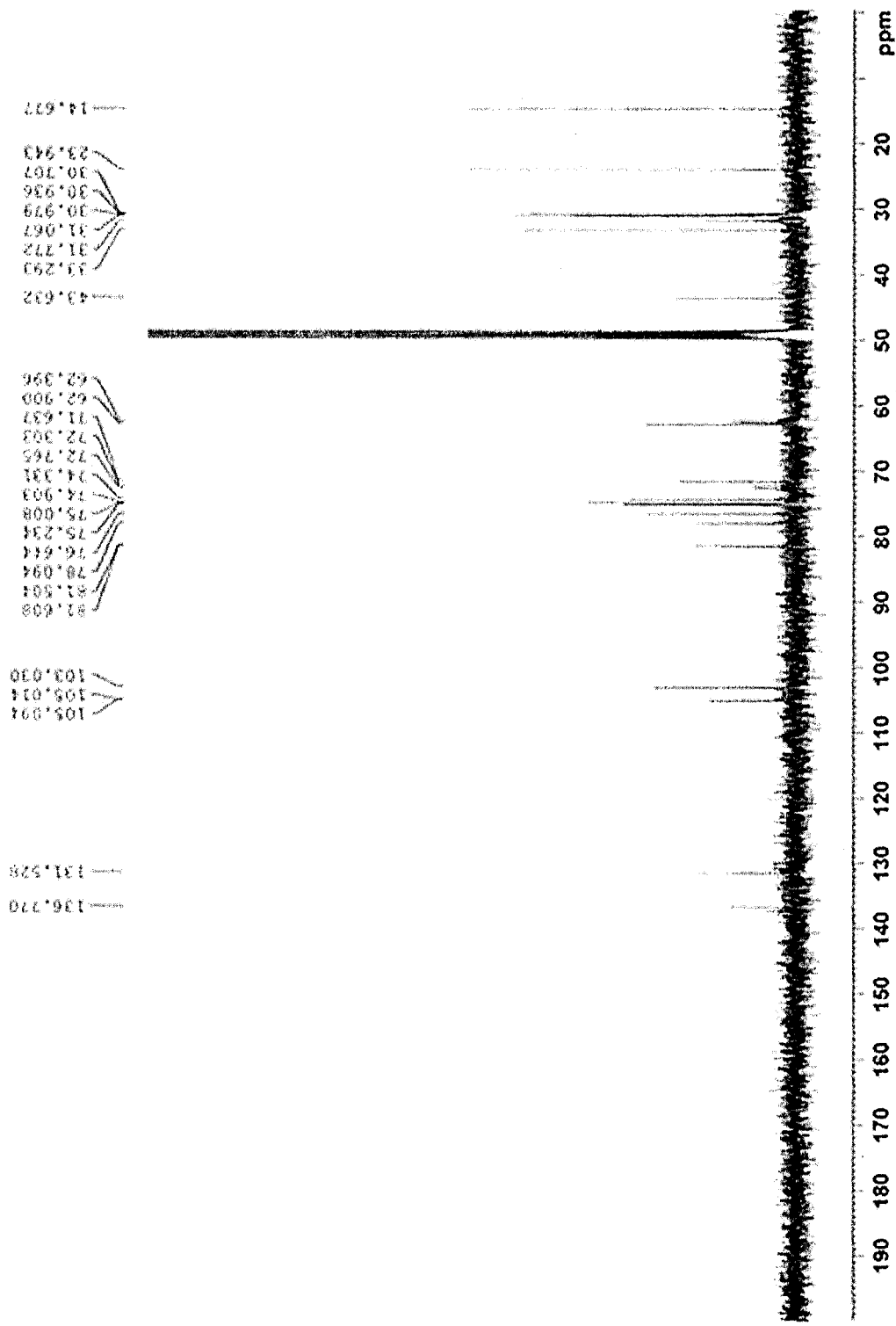

[Fig. 12]
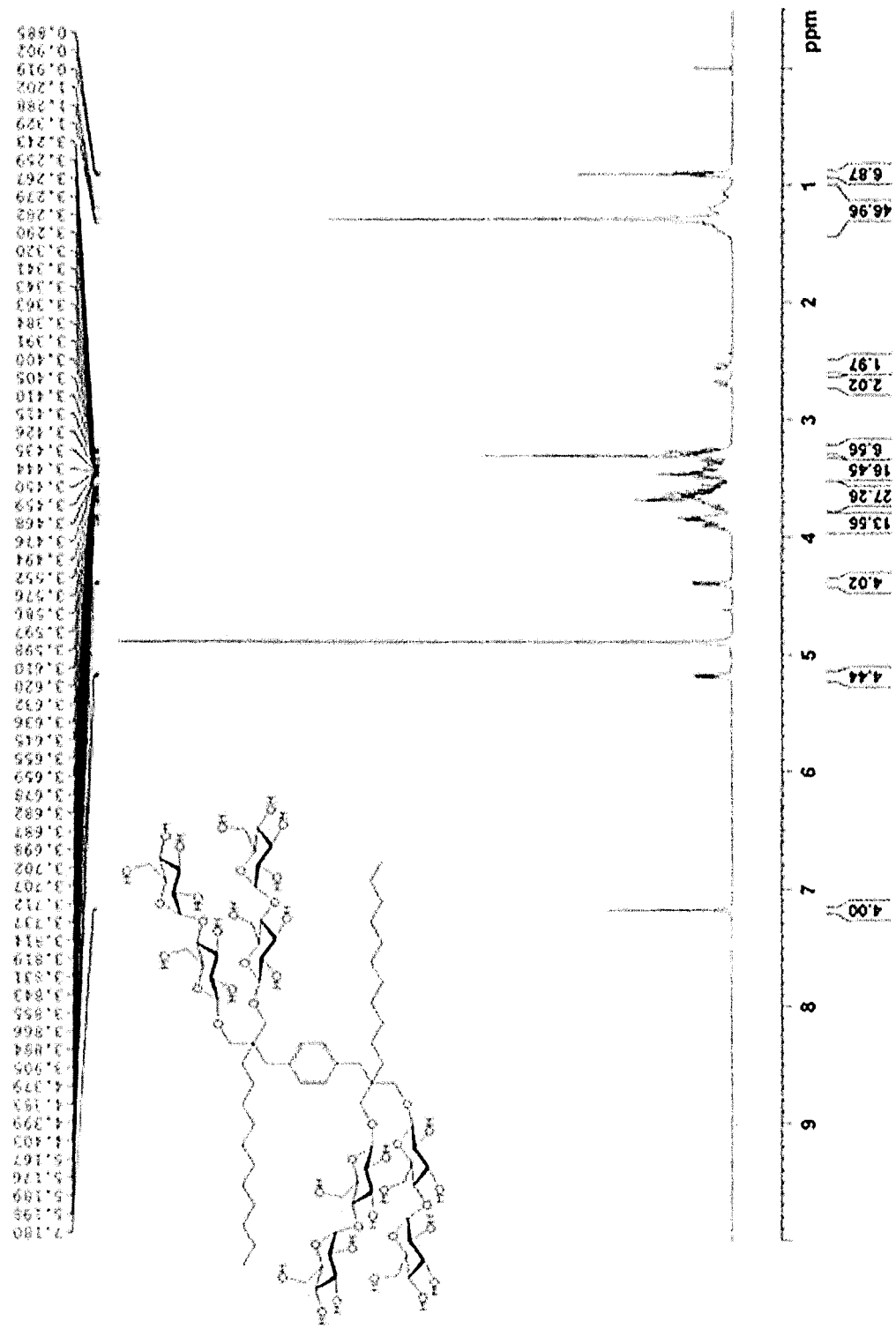

[Fig. 13]
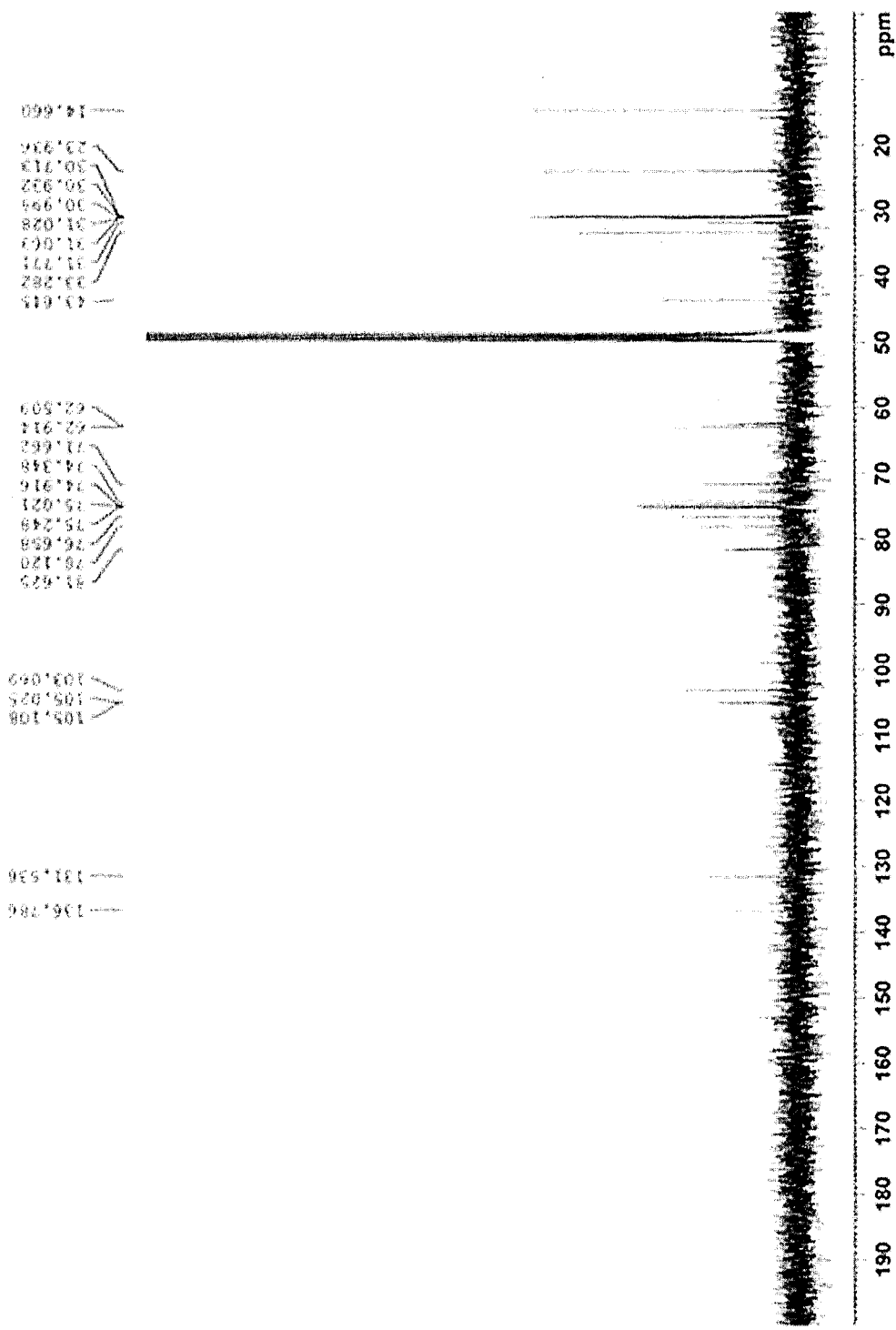

[Fig. 14]
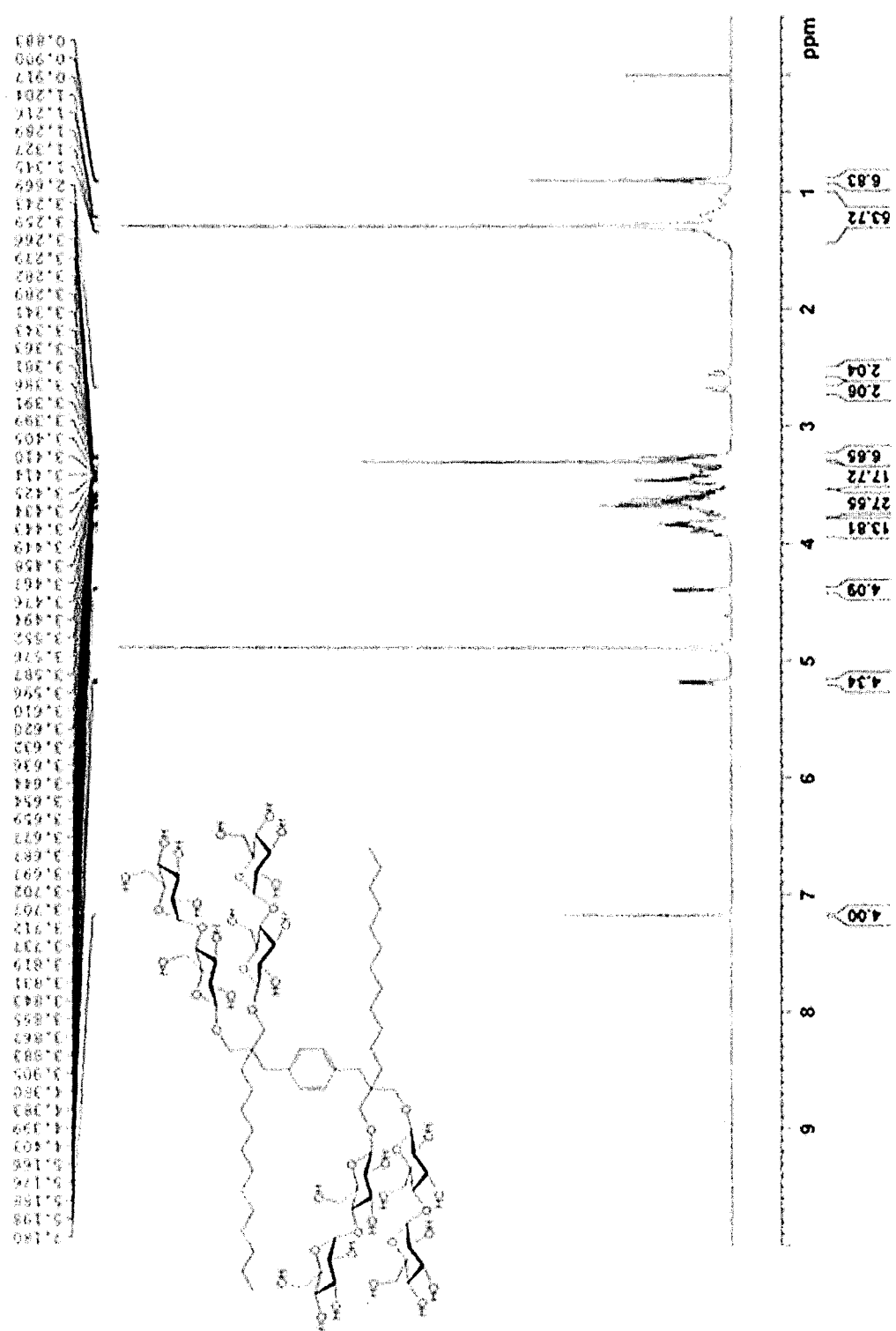

[Fig. 15]
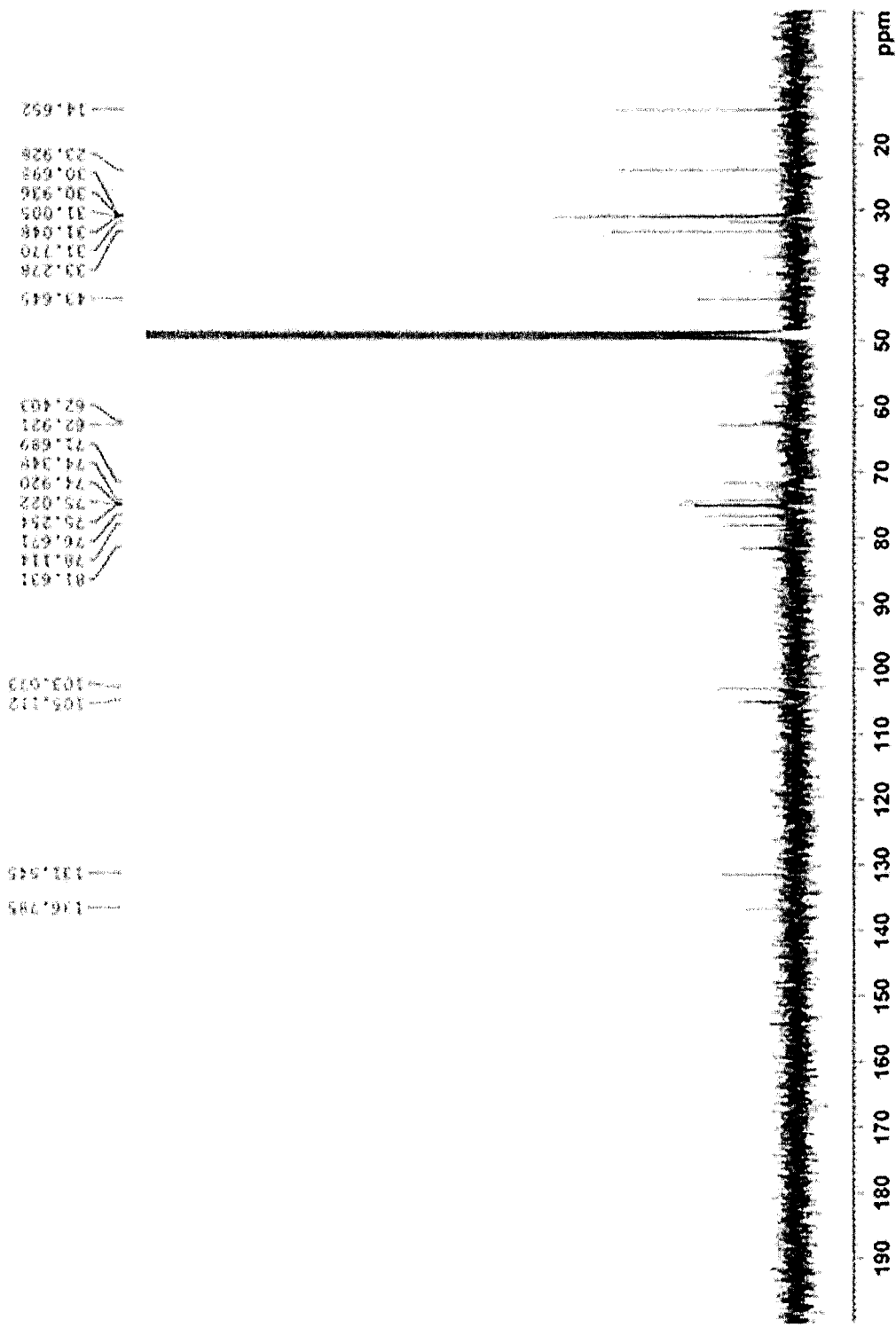

[Fig. 16]
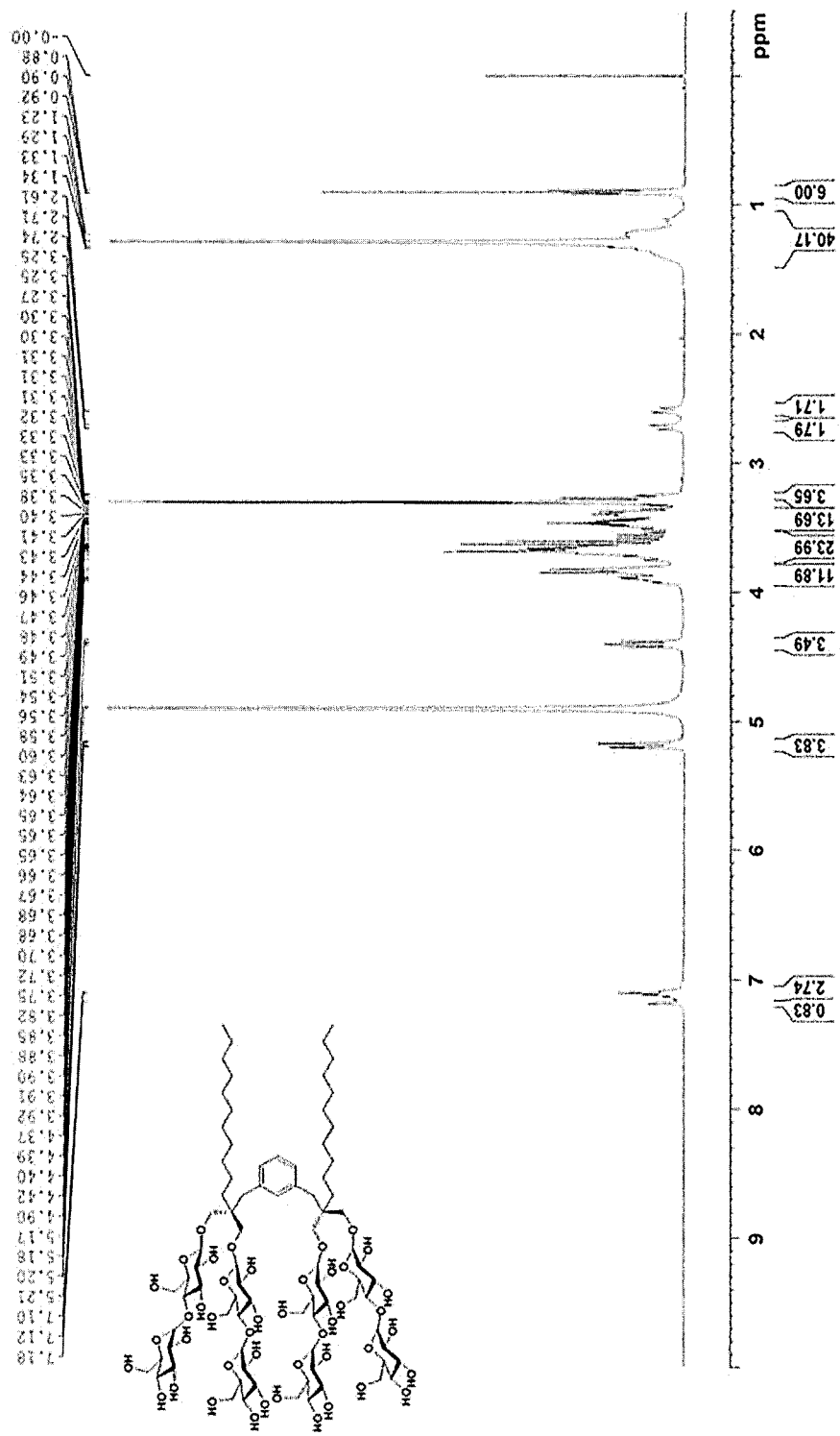

【Fig. 17】
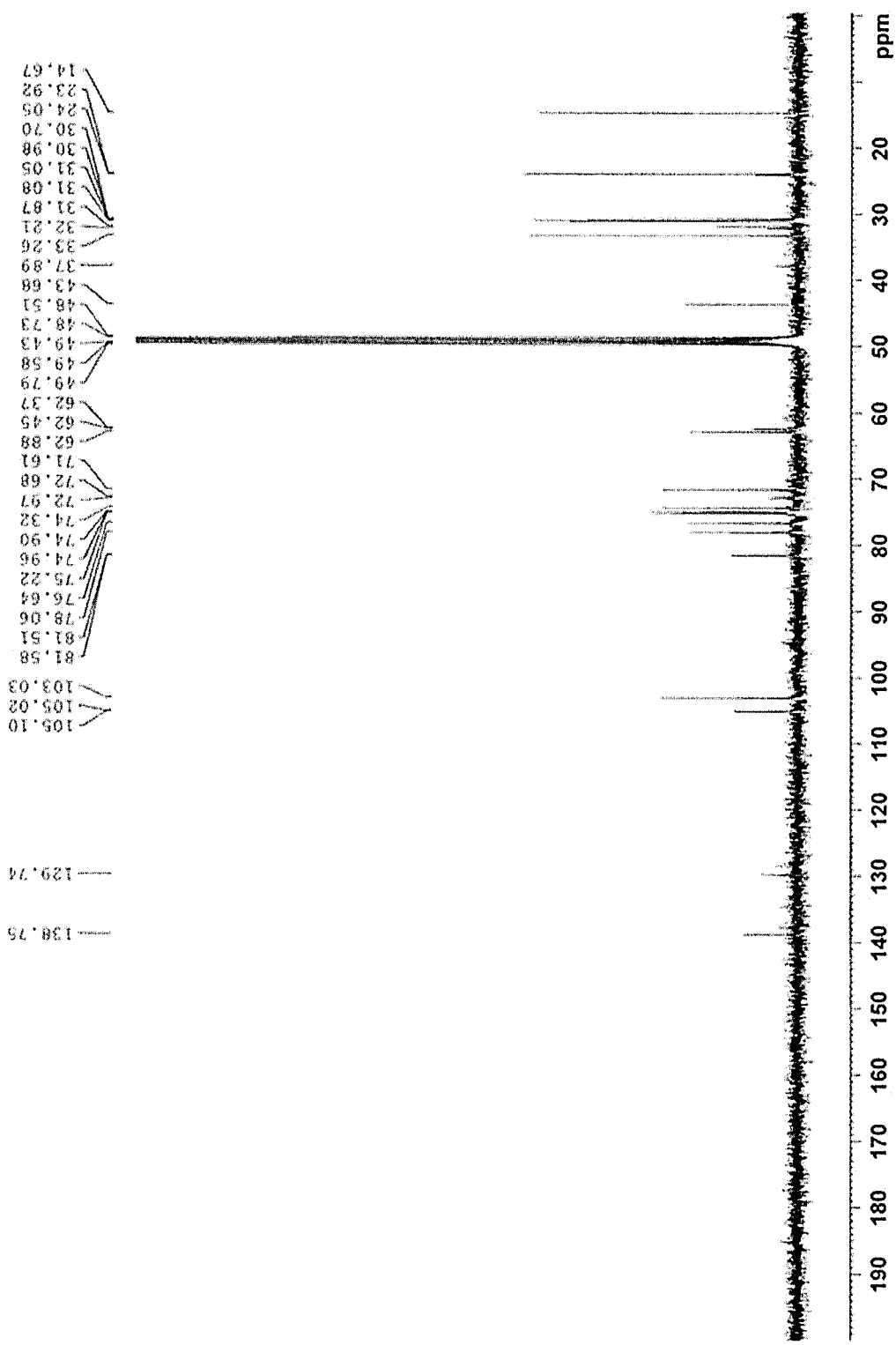

[Fig. 18]
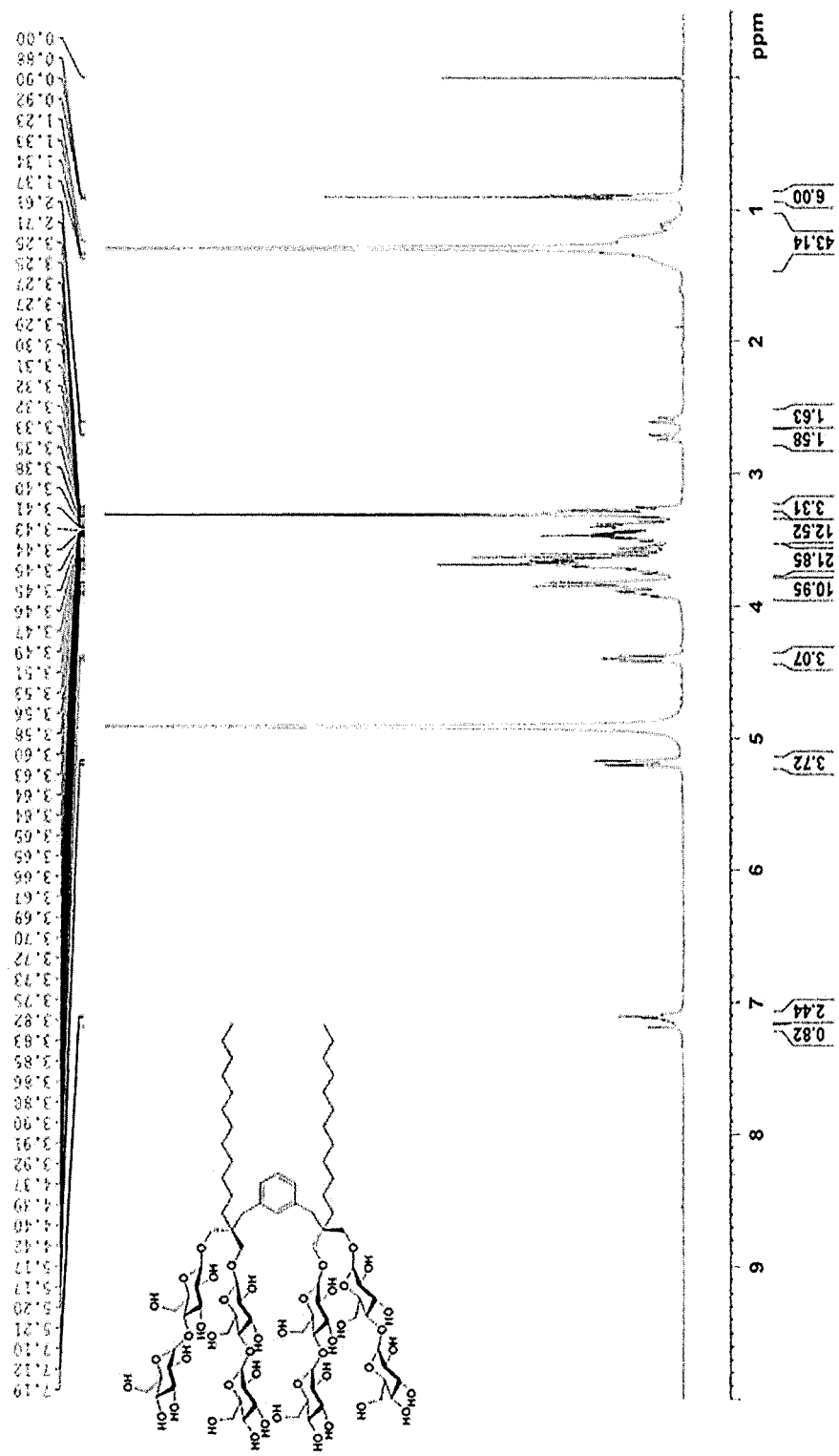

[Fig. 19]
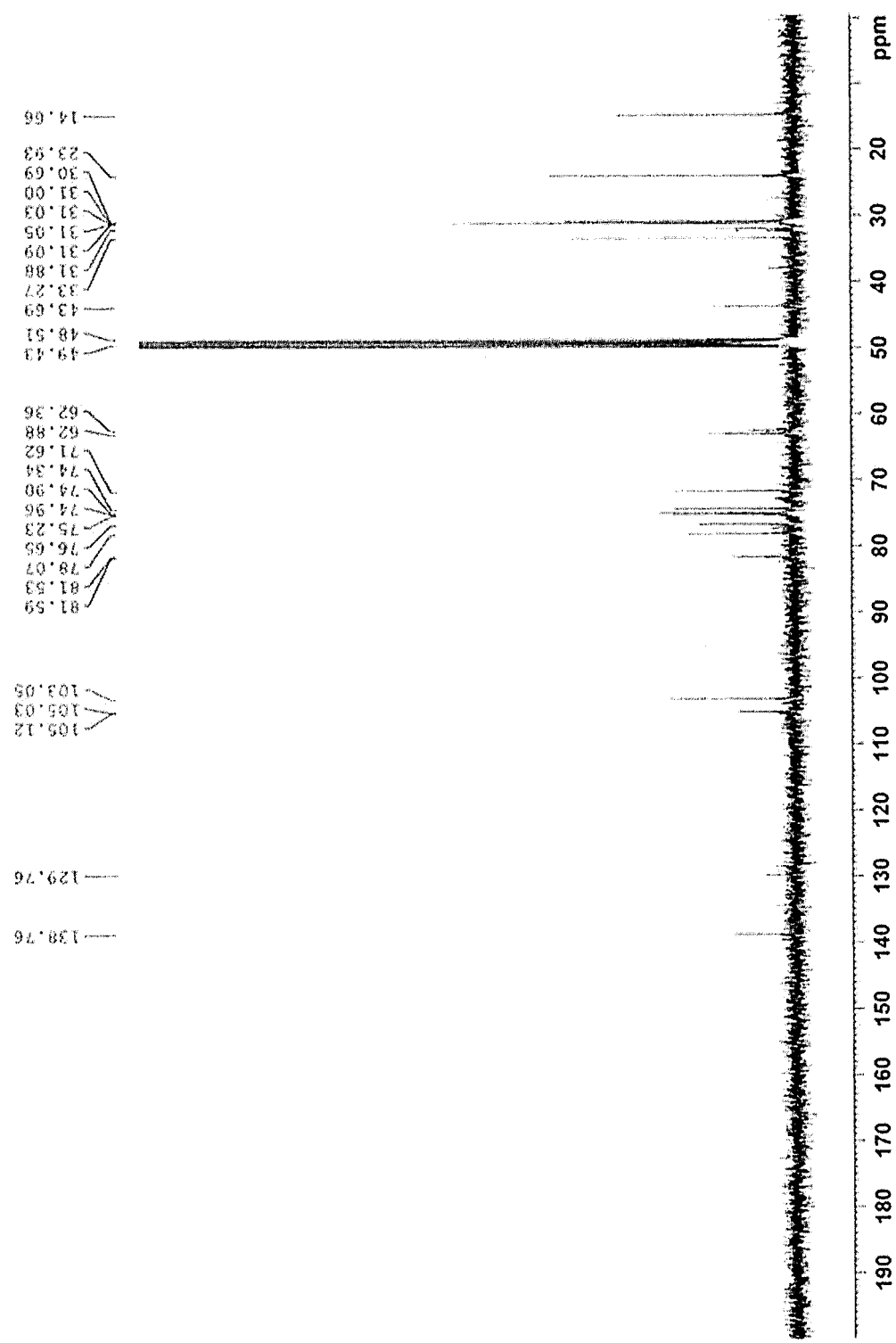

[Fig. 20]
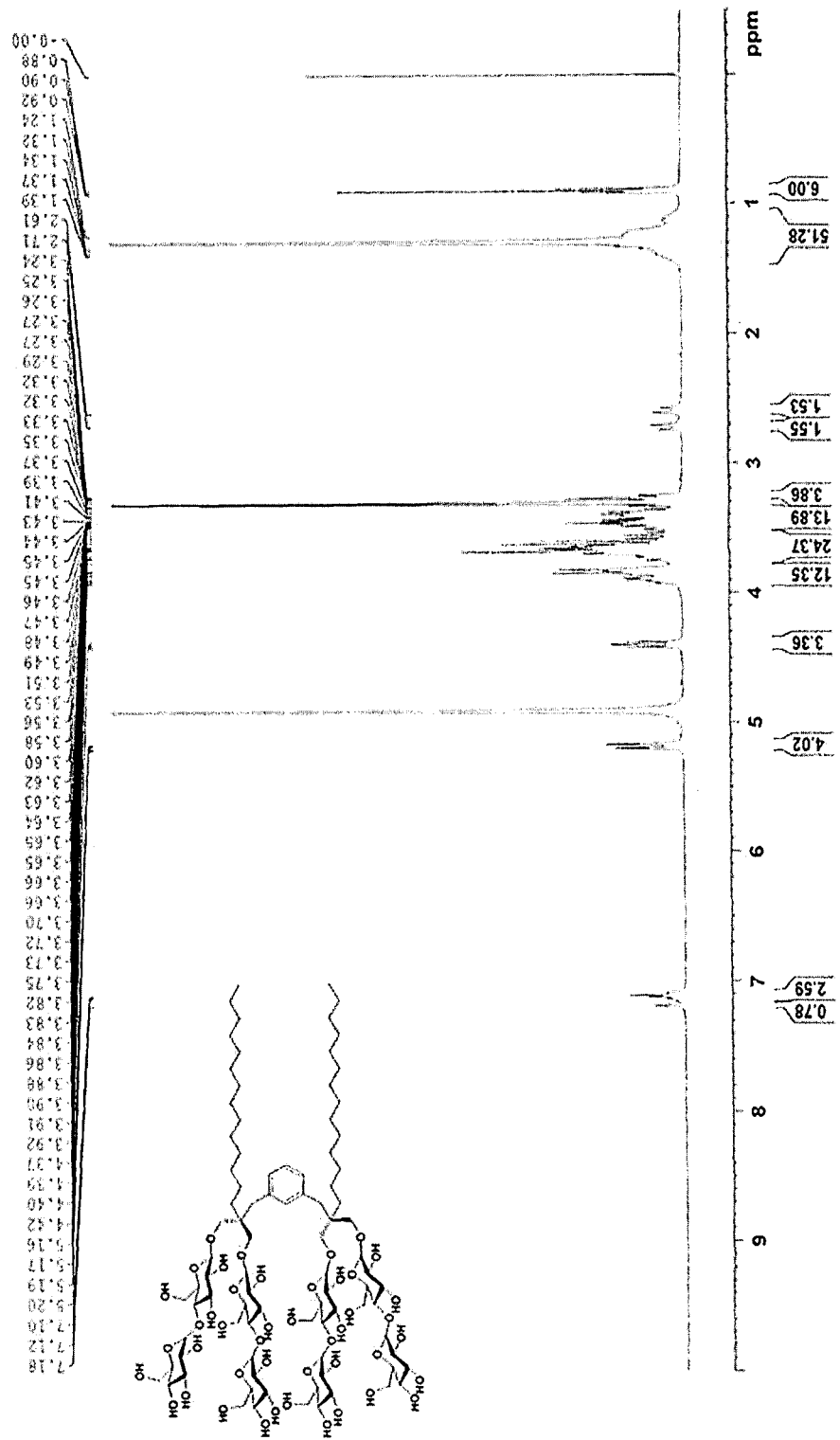

[Fig. 21]
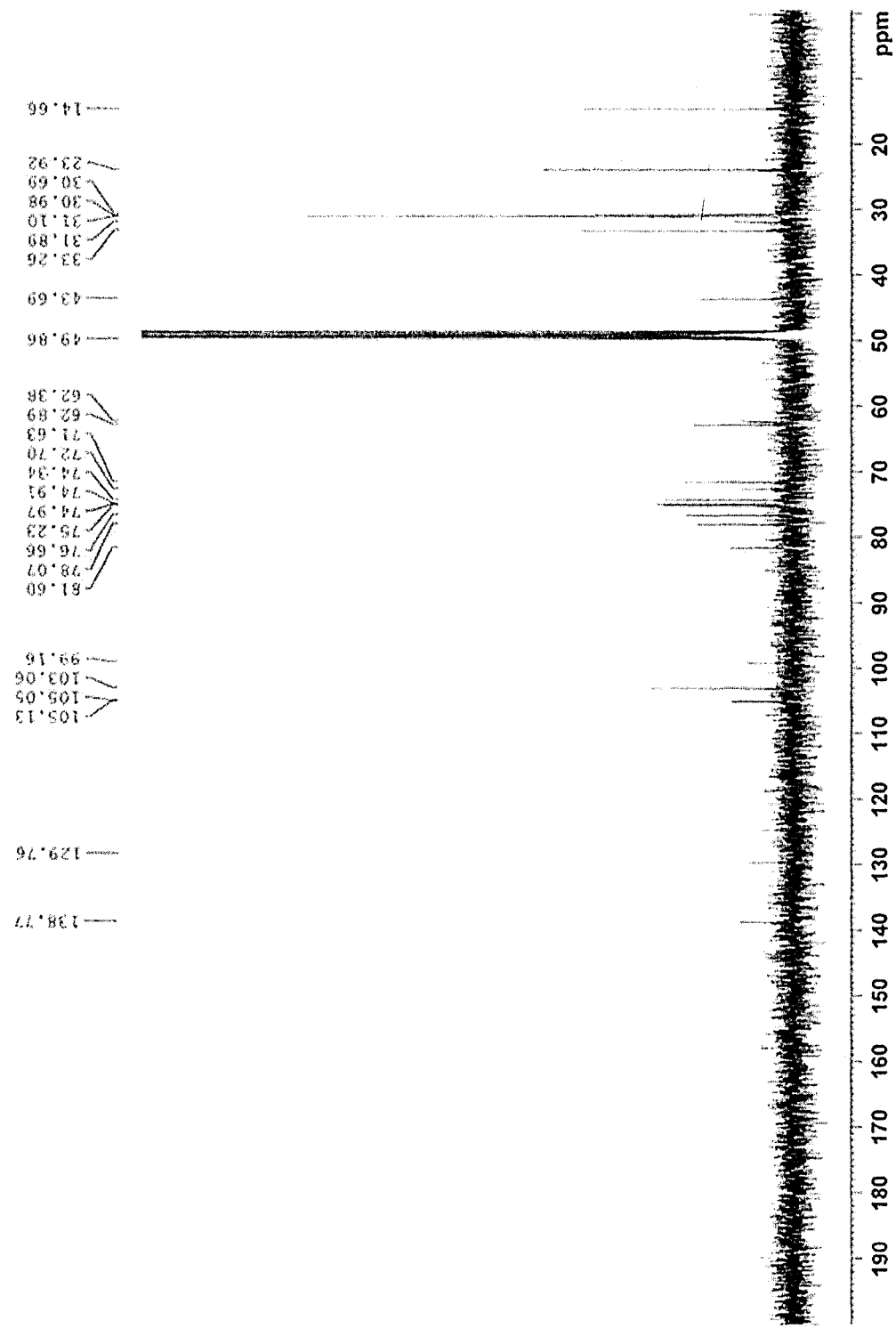

[Fig. 22]
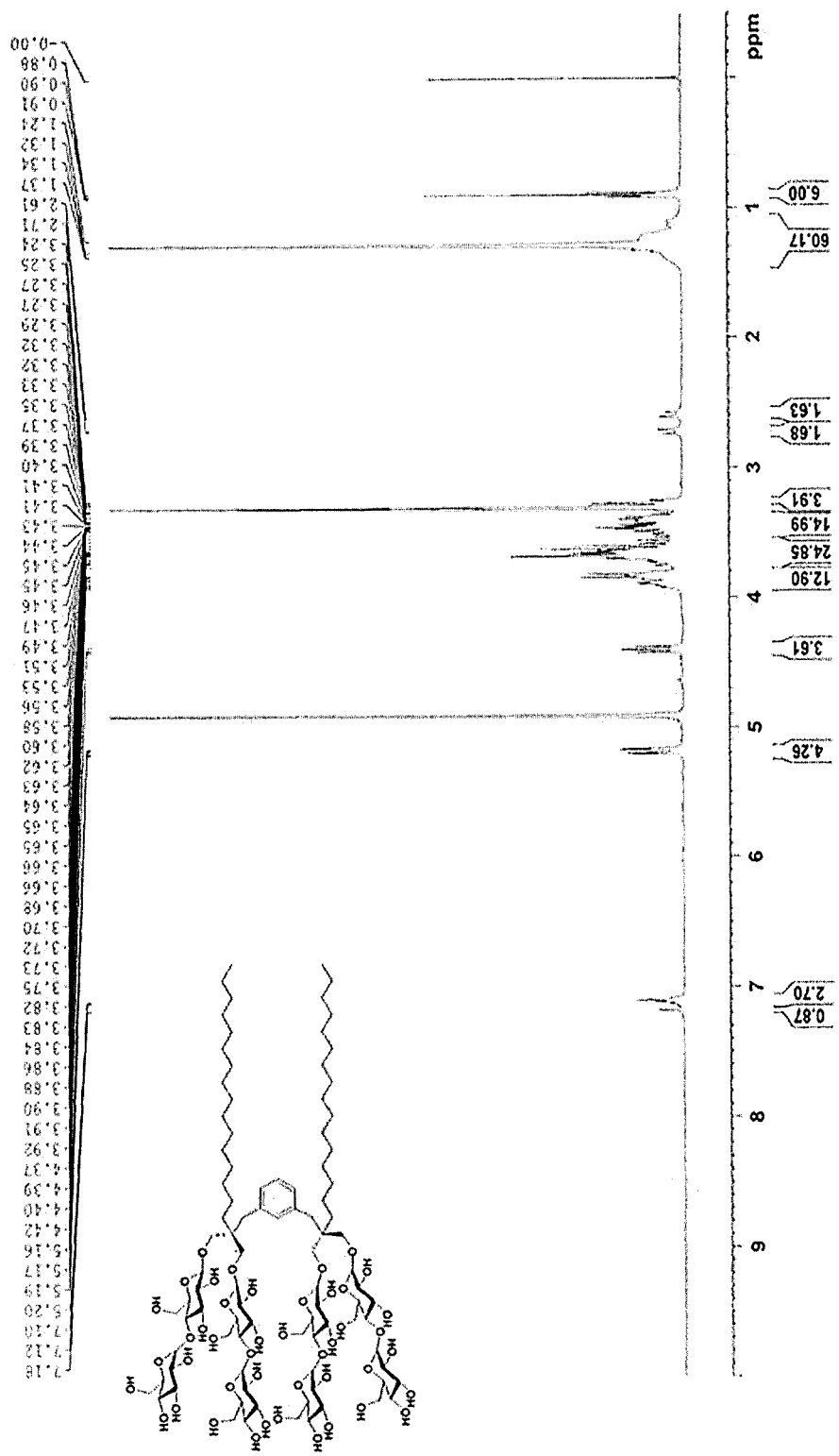

[Fig. 23]
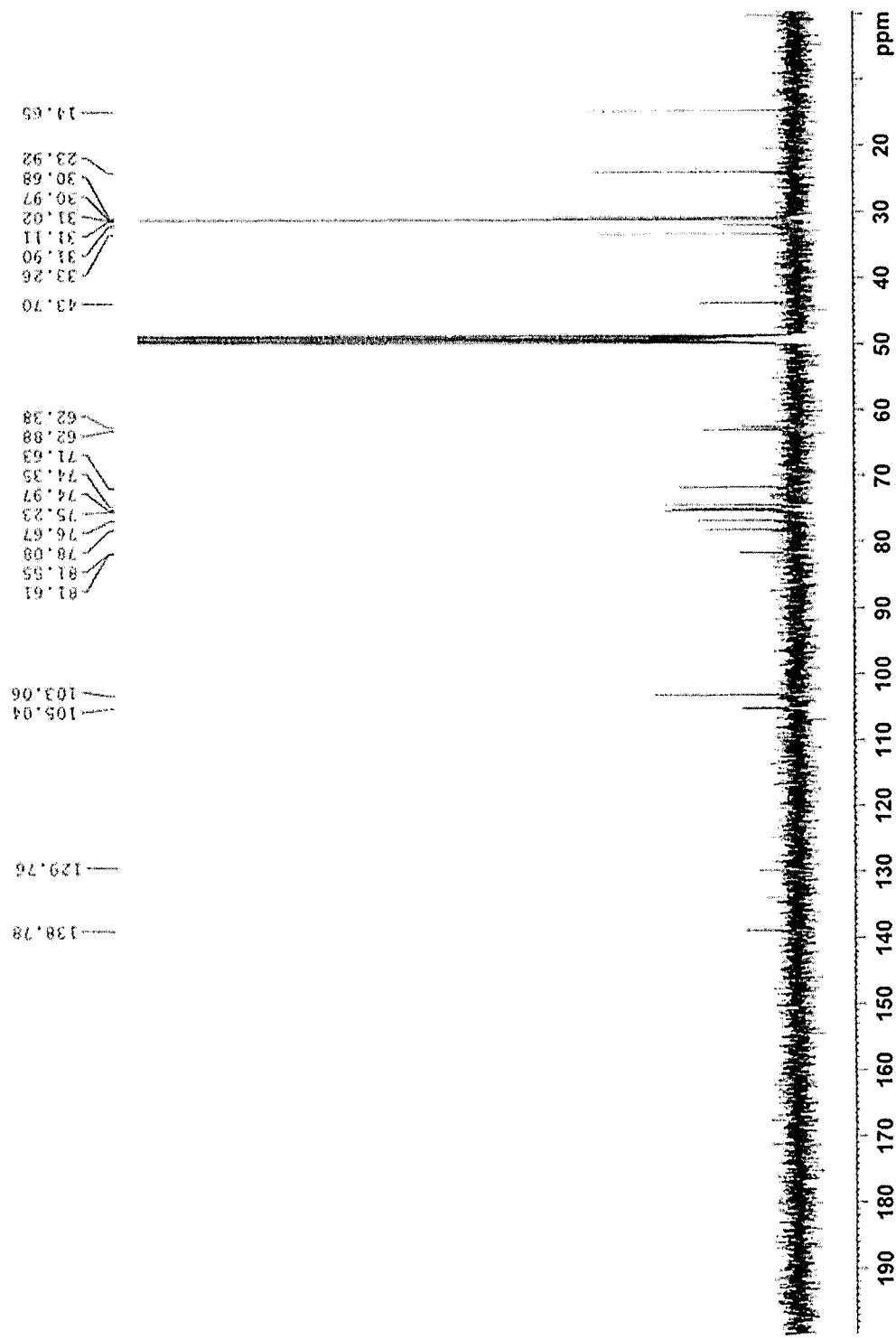

[Fig. 24]
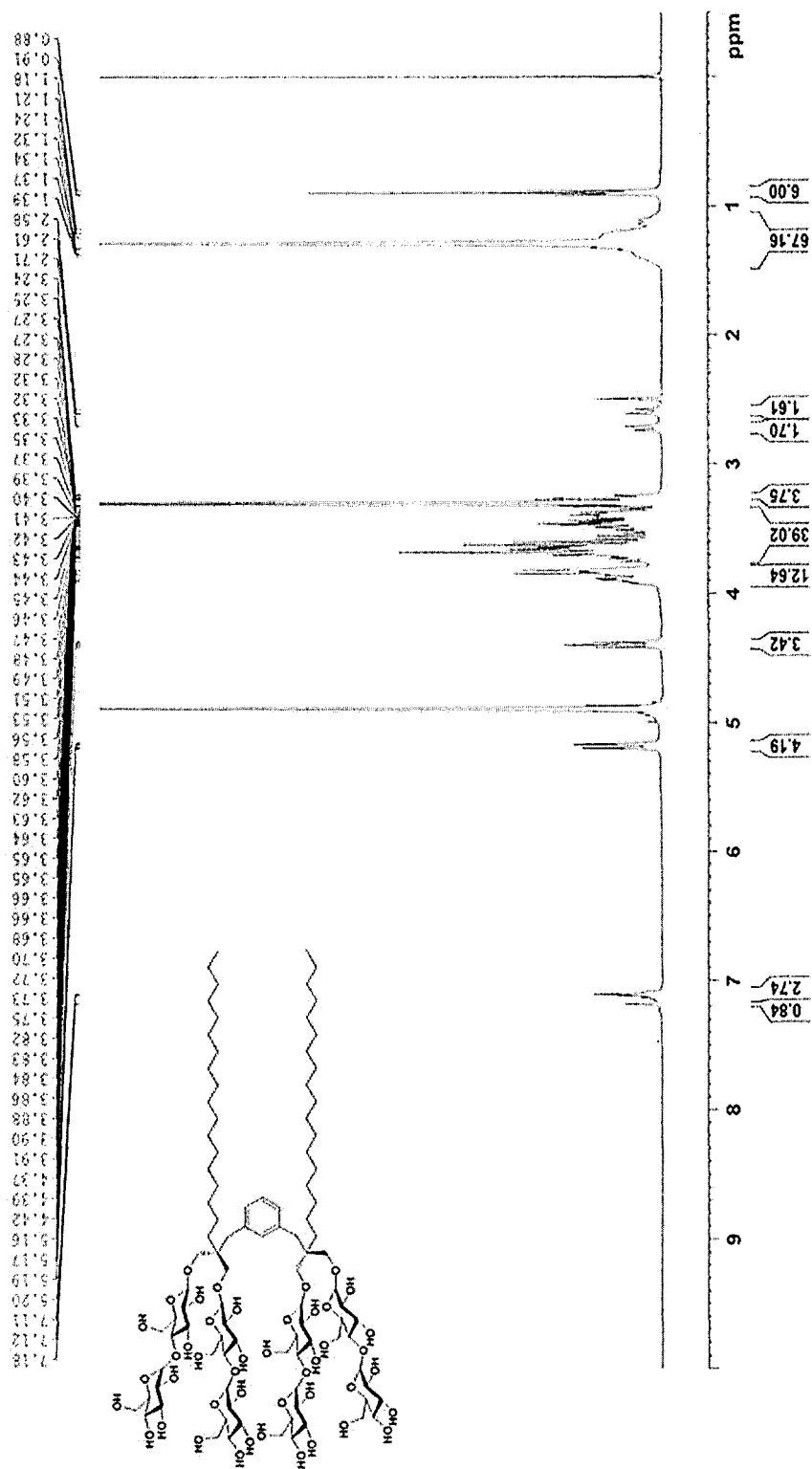

[Fig. 25]
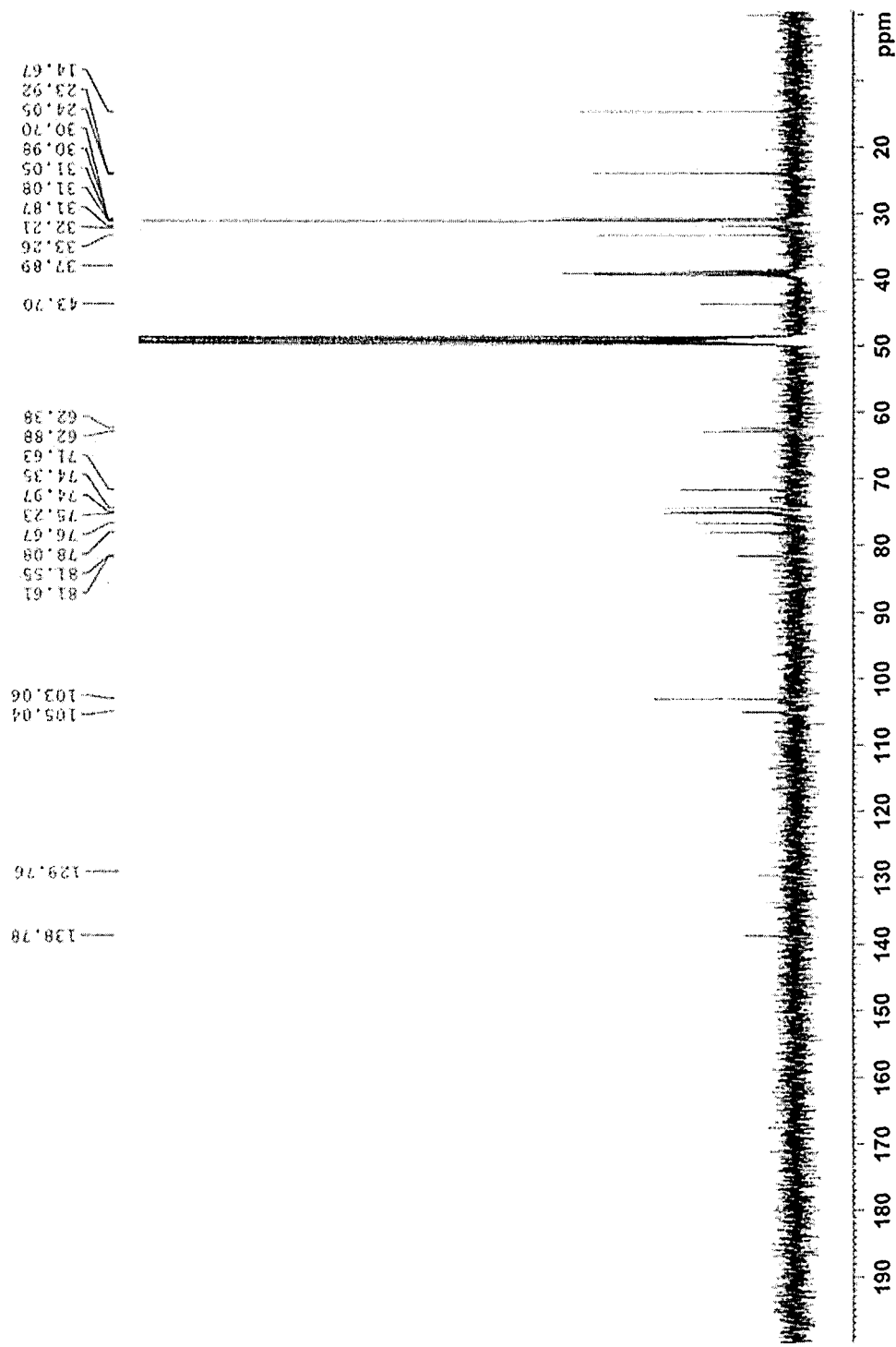

[Fig. 26]
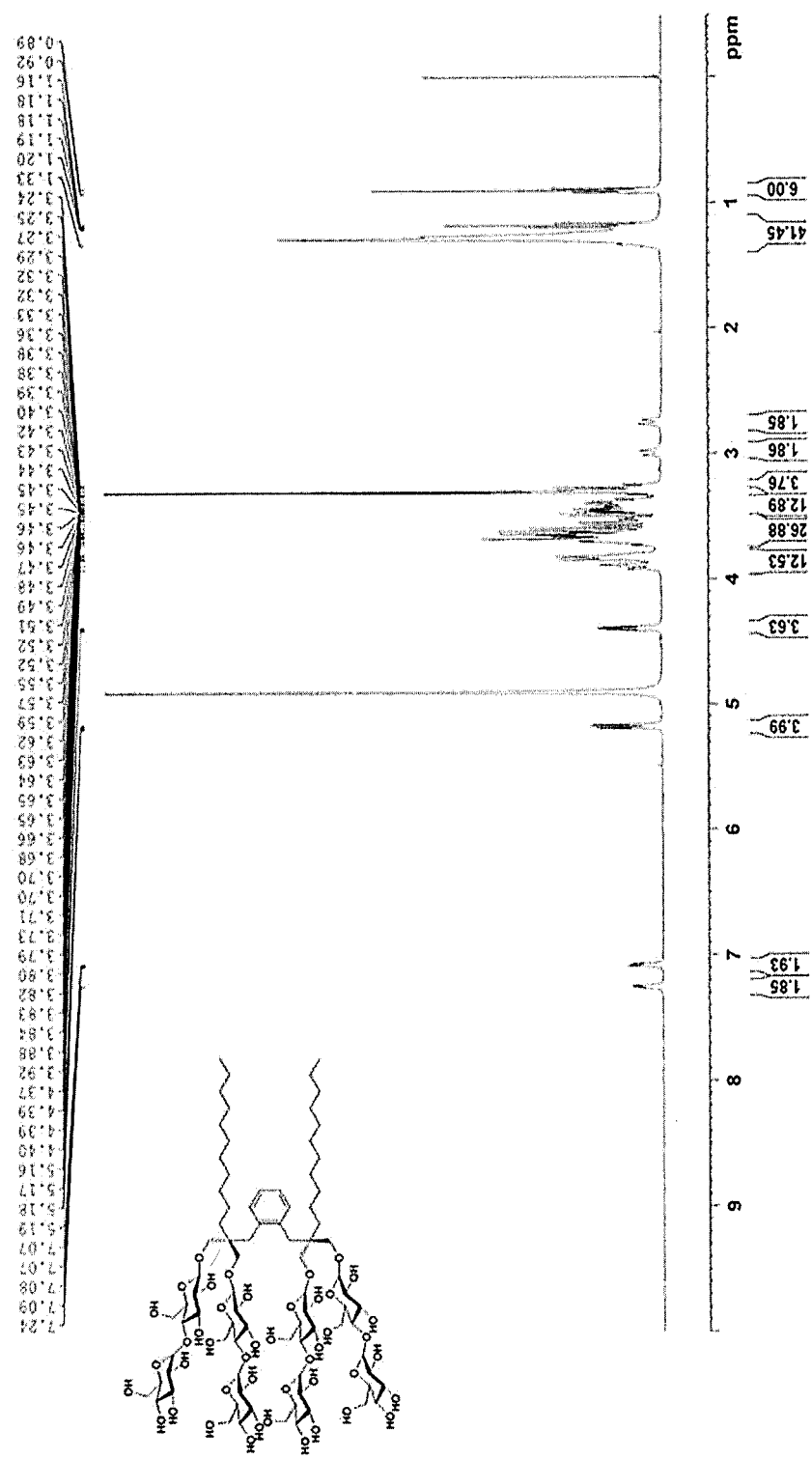

[Fig. 27]
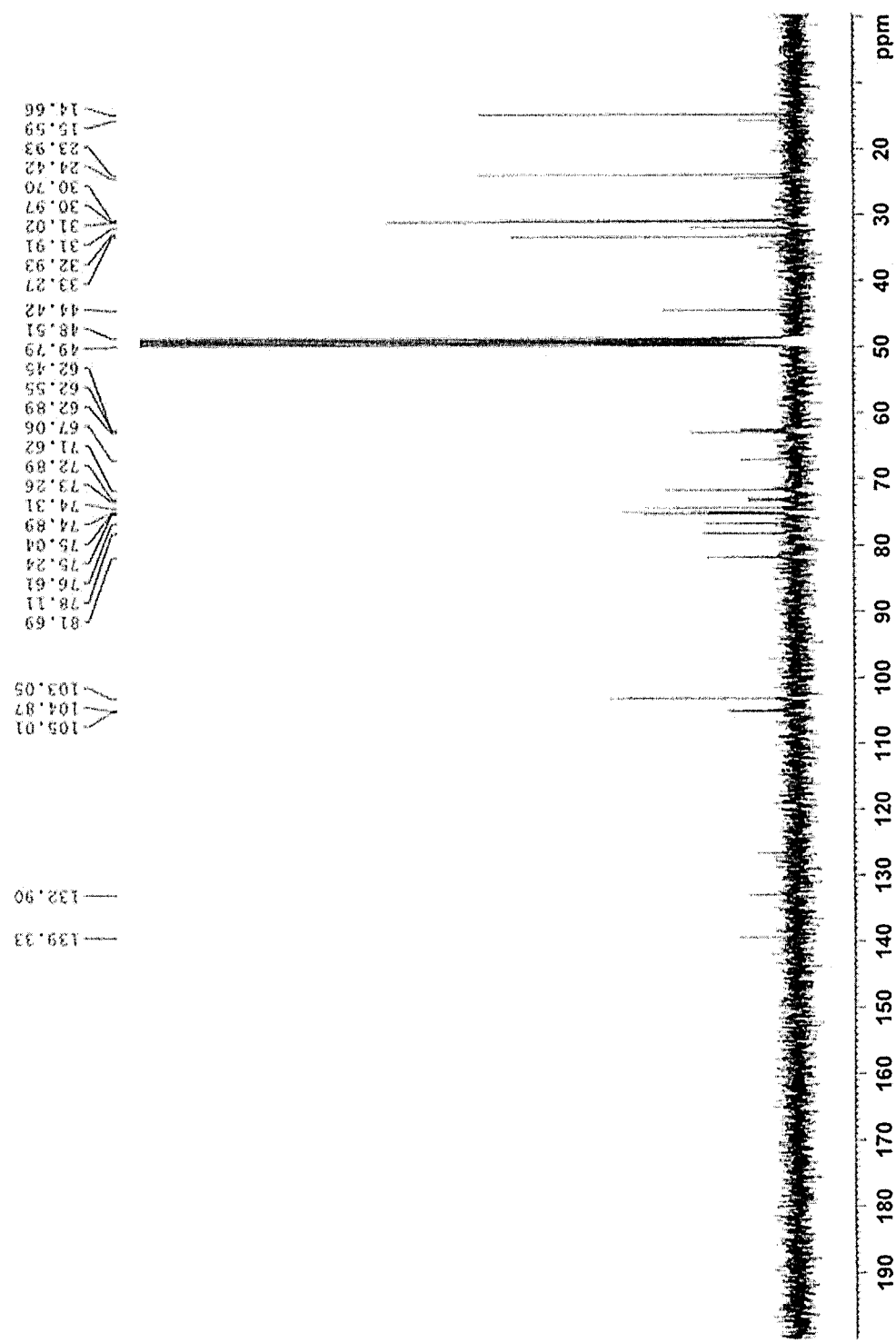

[Fig. 28]
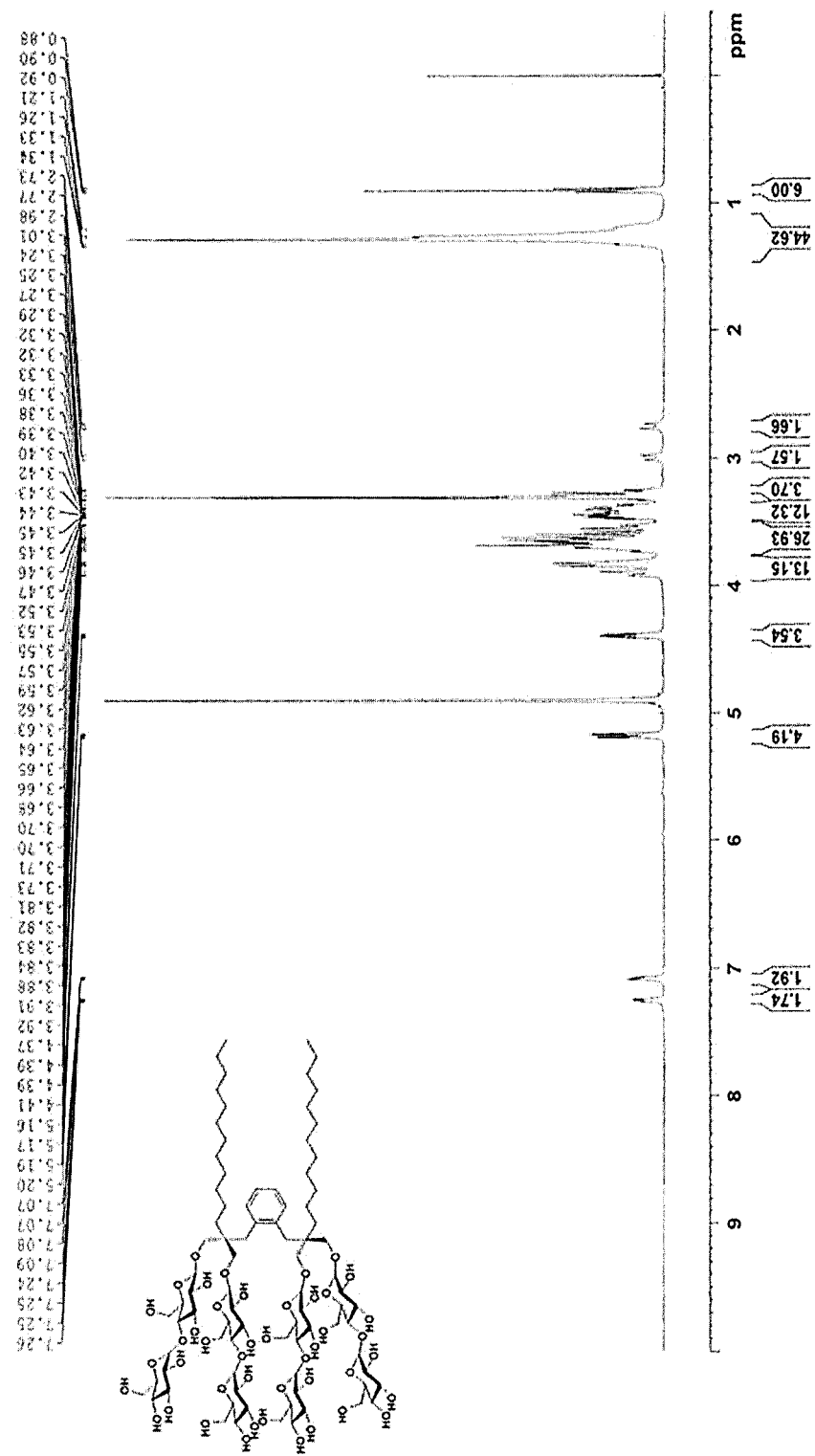

[Fig. 29]
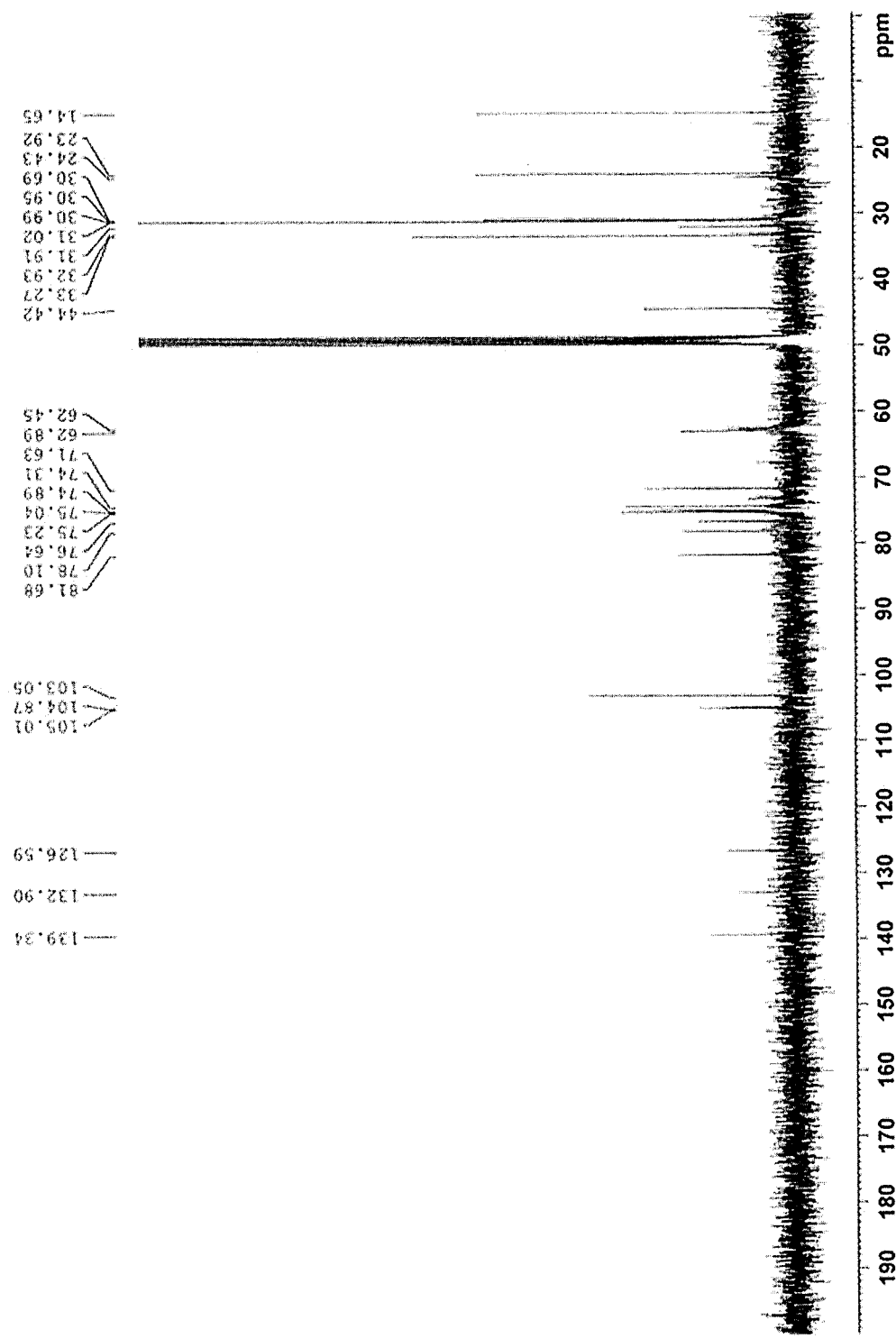

[Fig. 30]
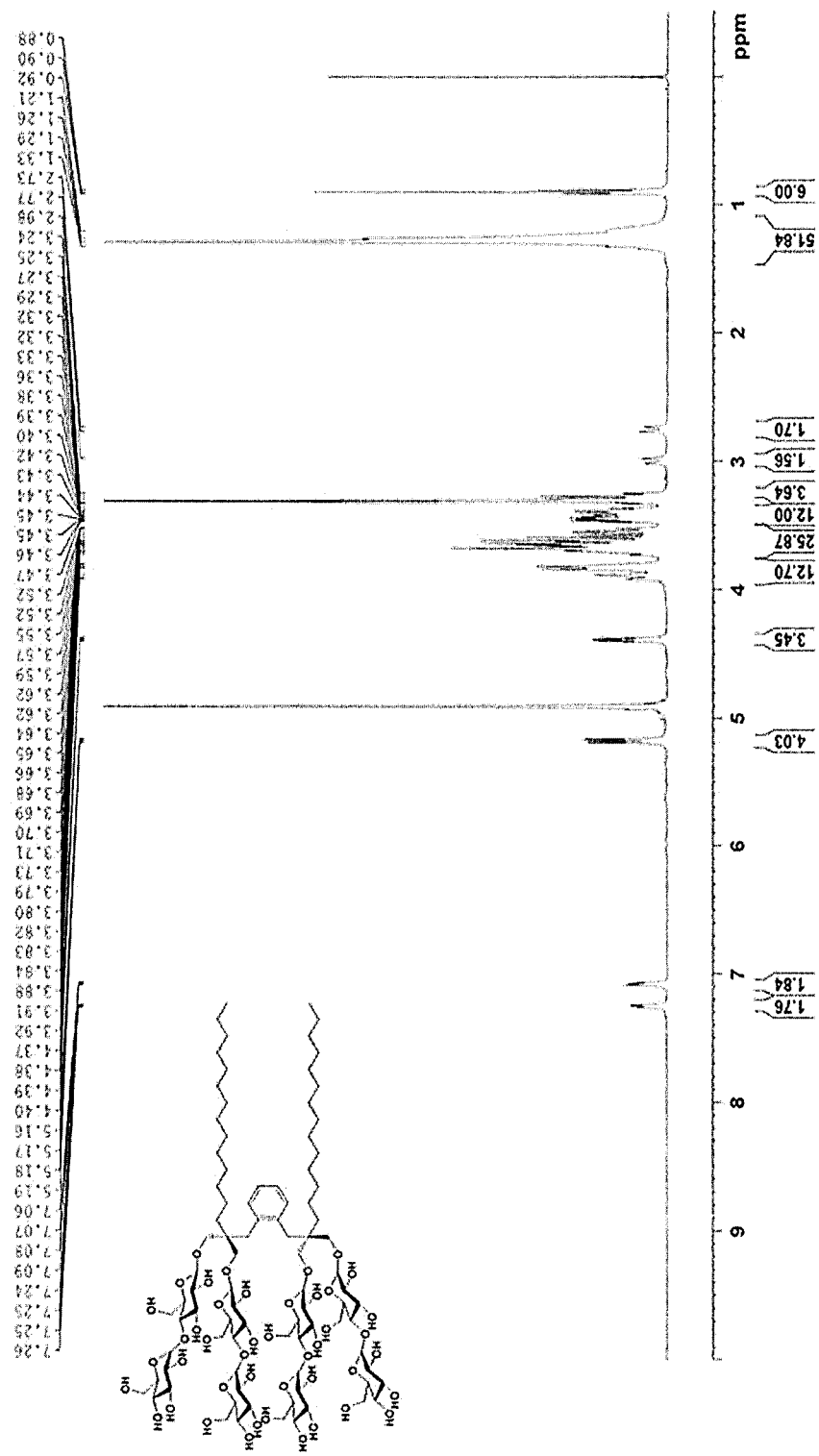

[Fig. 31]
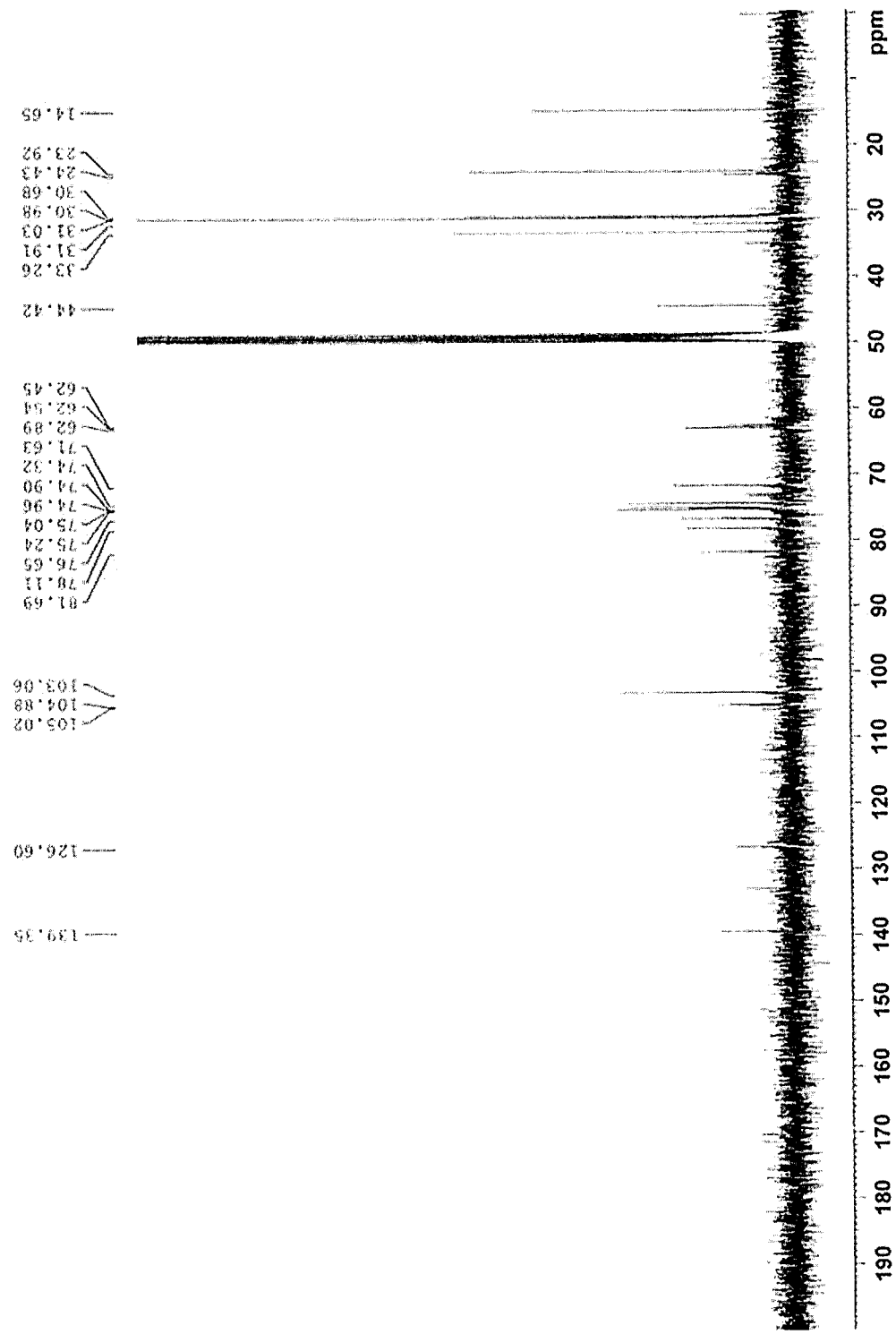

[Fig. 32]
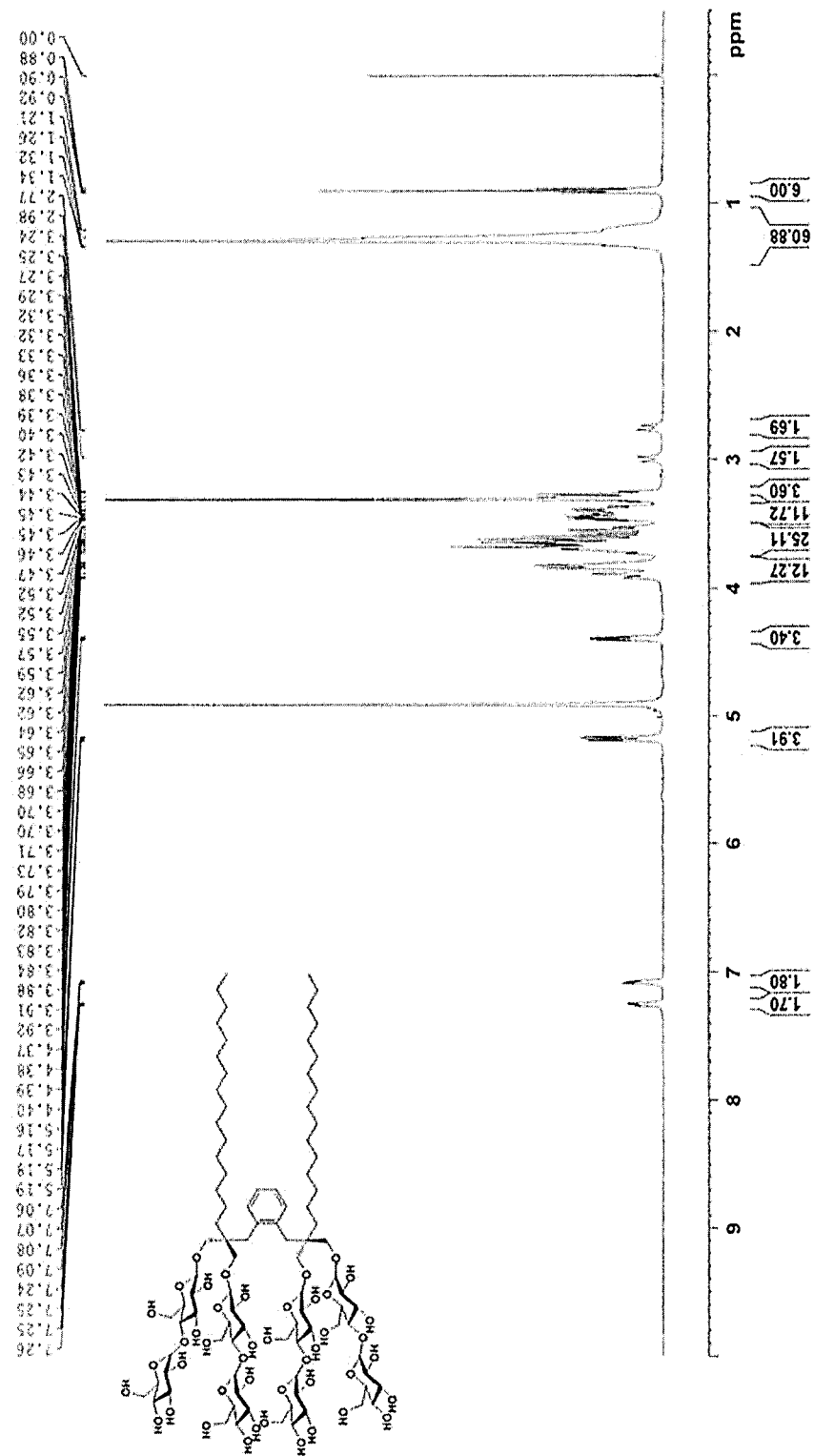

[Fig. 33]
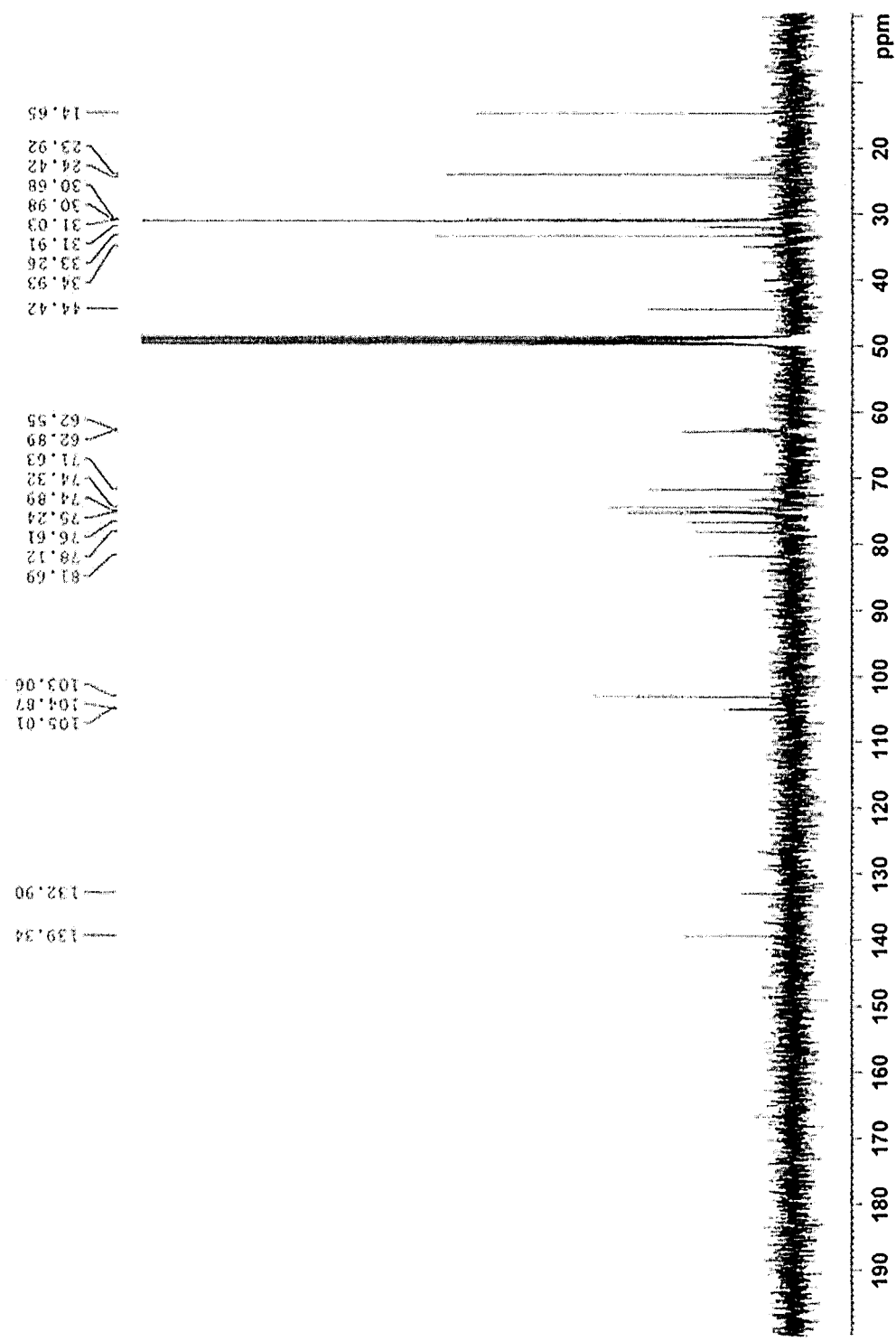

[Fig. 34]
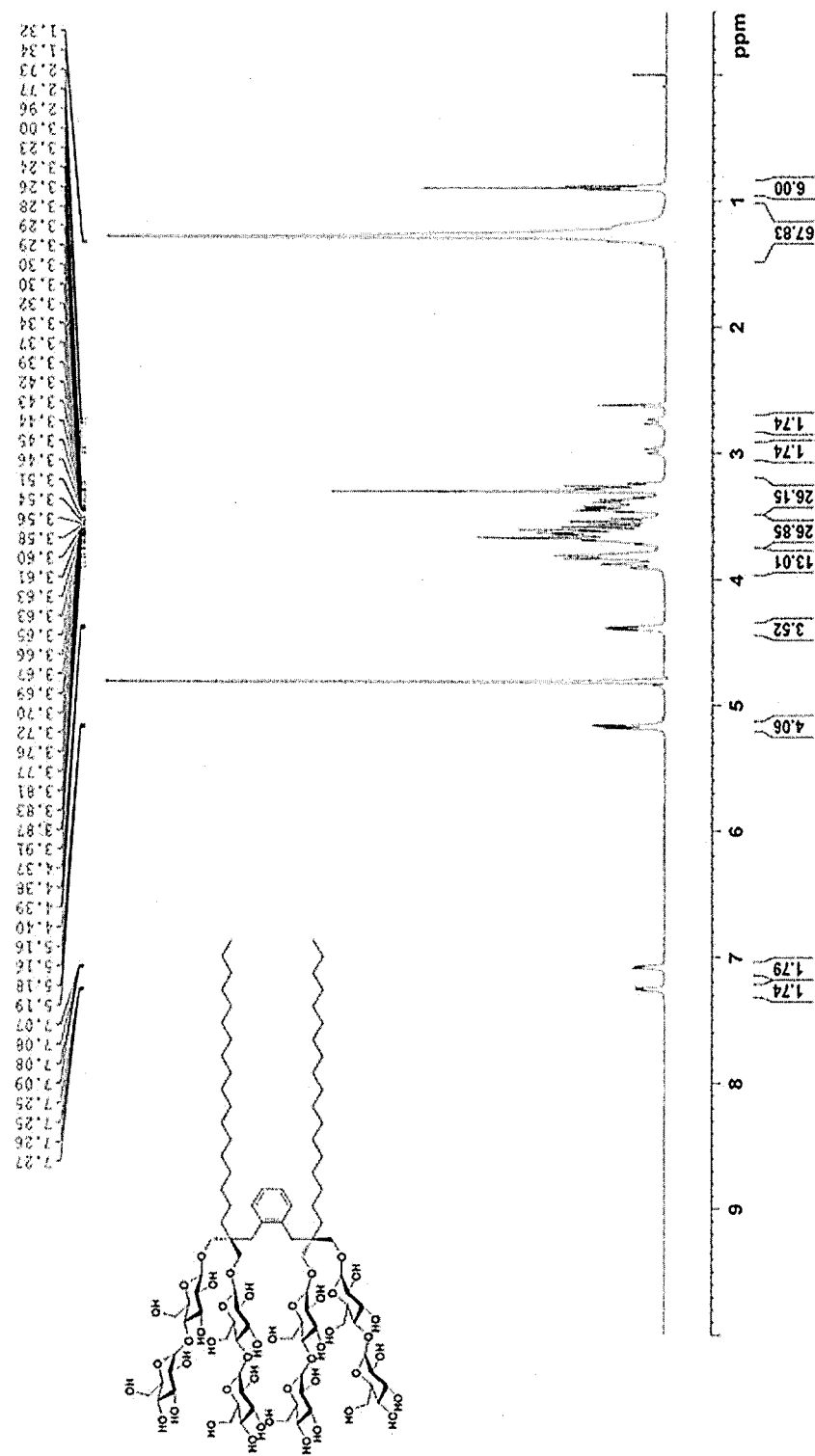

[Fig. 35]
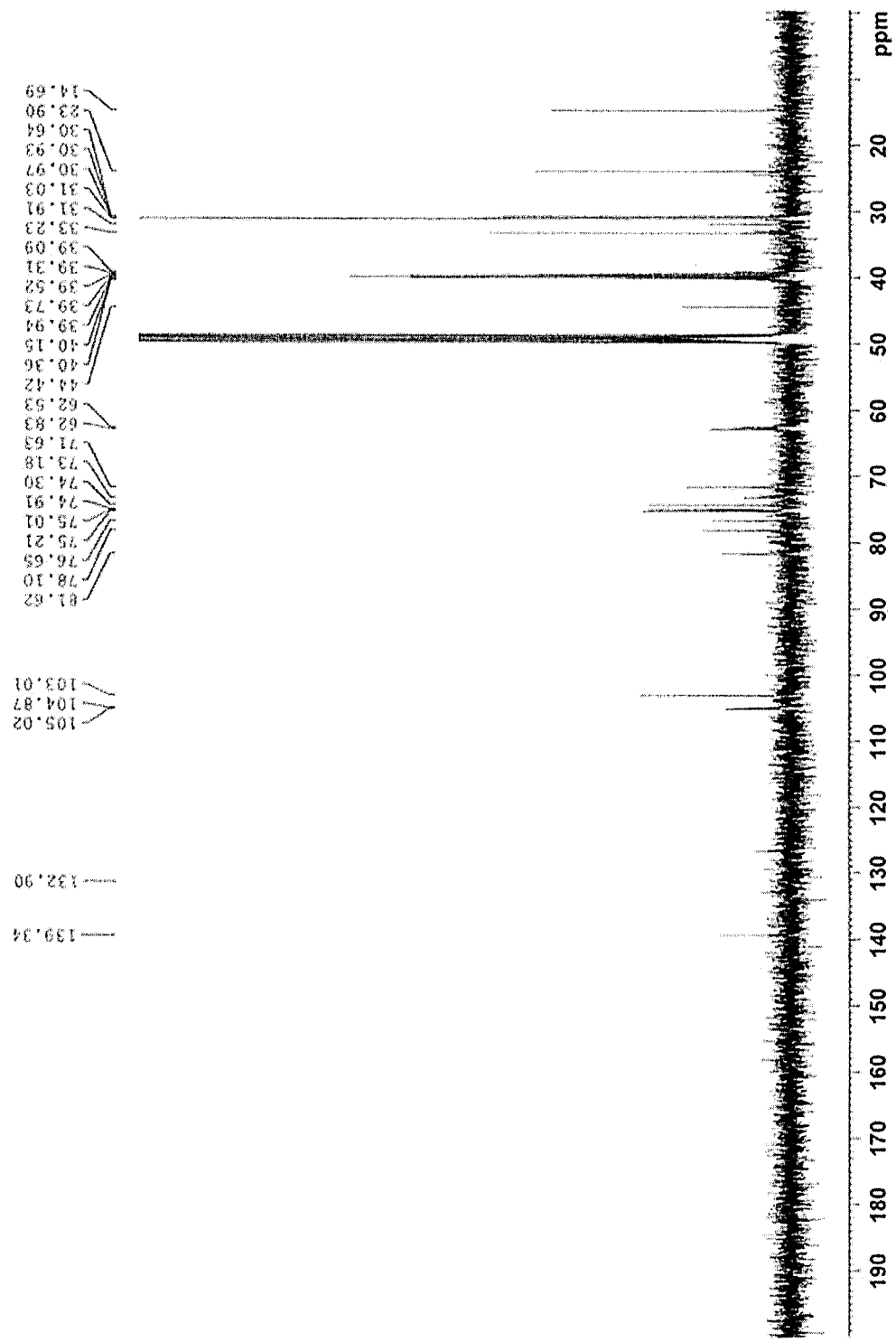

【Fig. 36a】
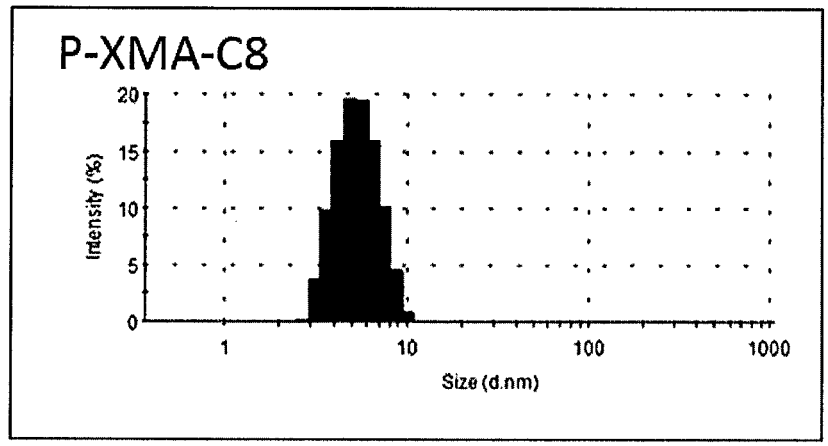
【Fig. 36b】
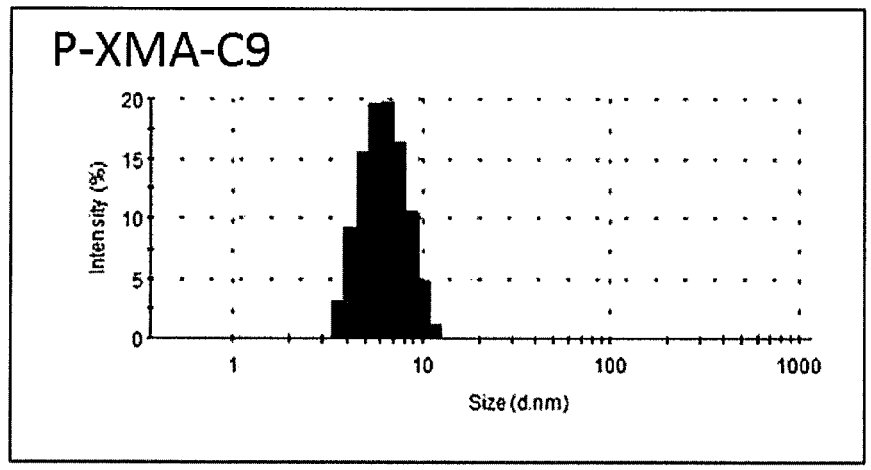

【Fig. 36c】
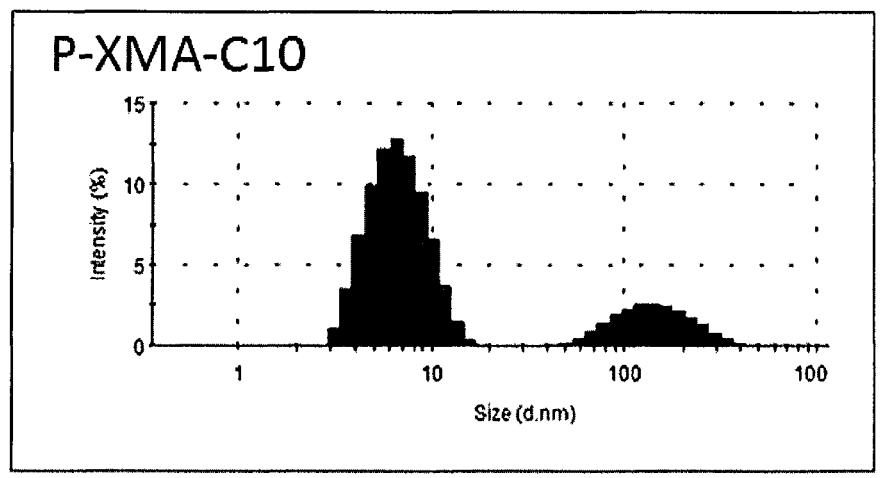
【Fig. 36d】
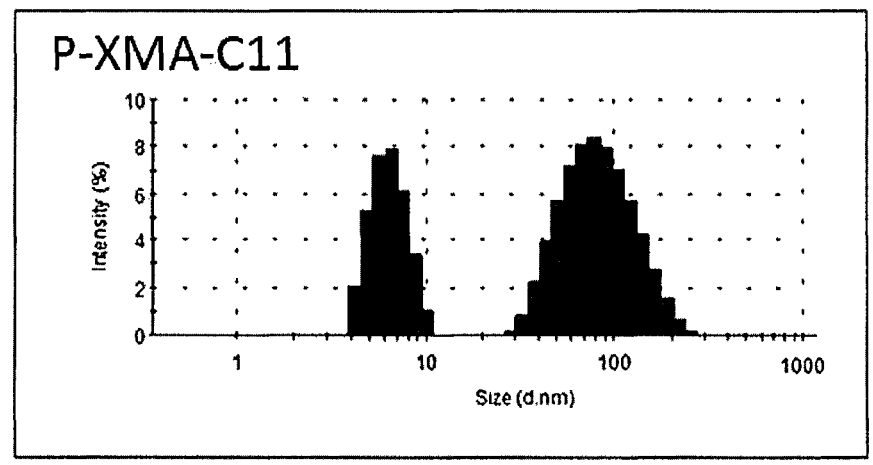

[Fig. 36e]
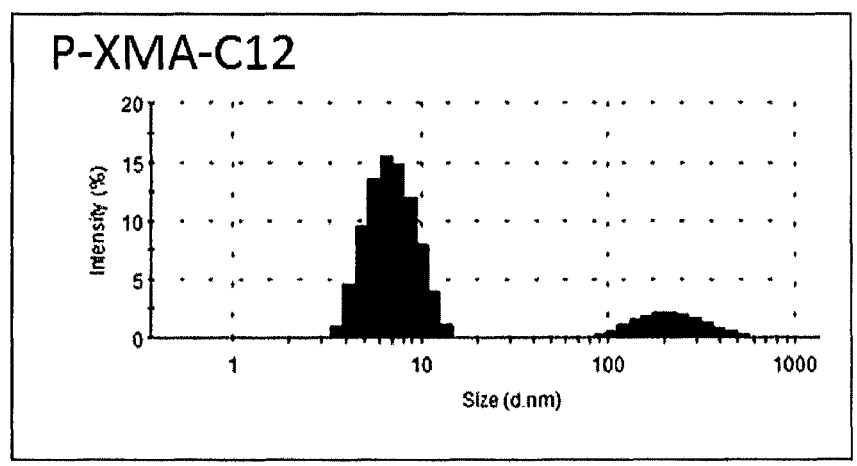
[Fig. 36f]
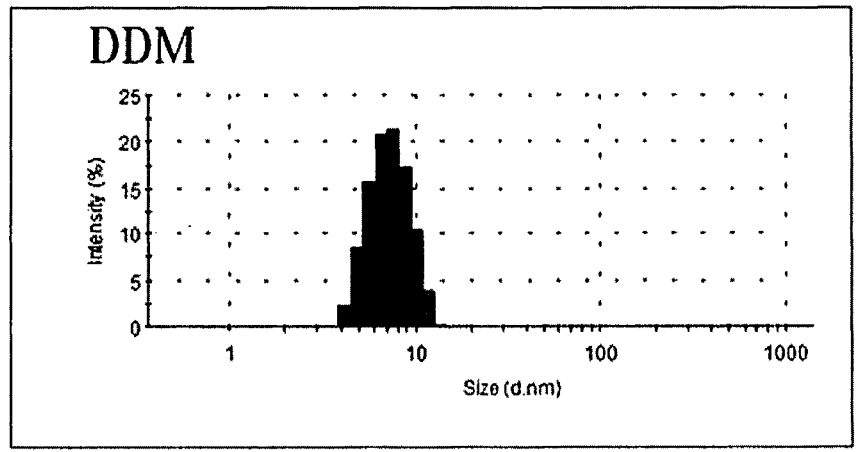

[Fig. 37]
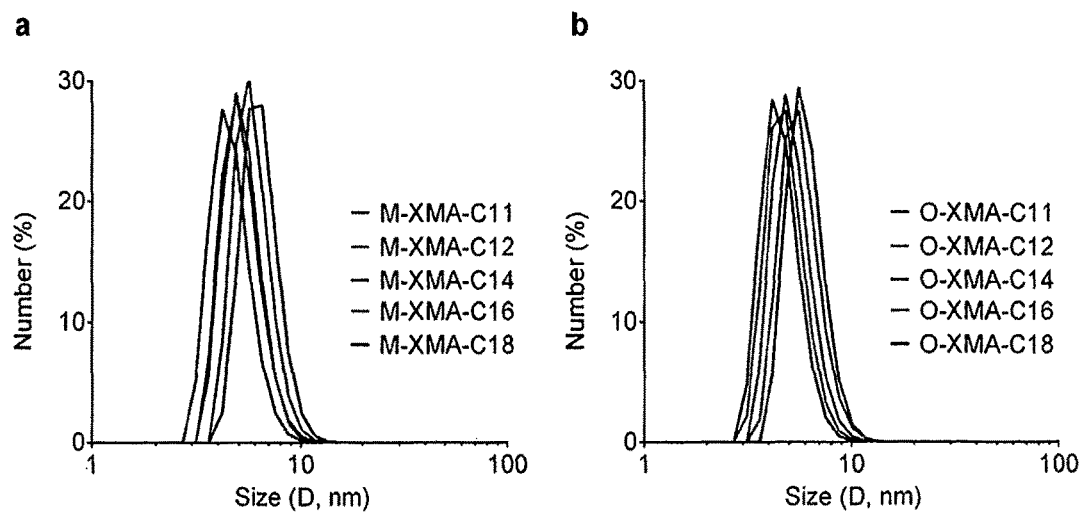
[Fig. 38]
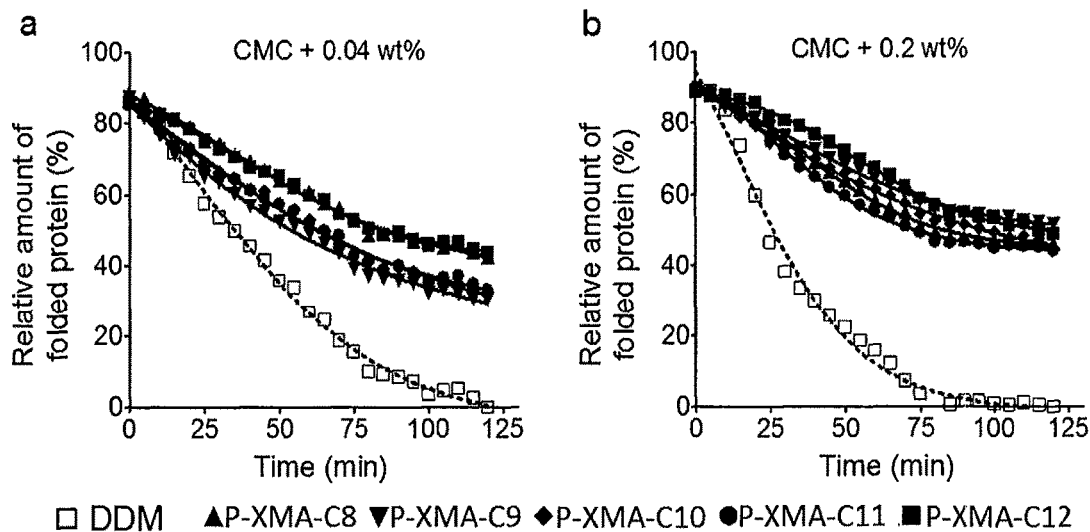

[Fig. 39]
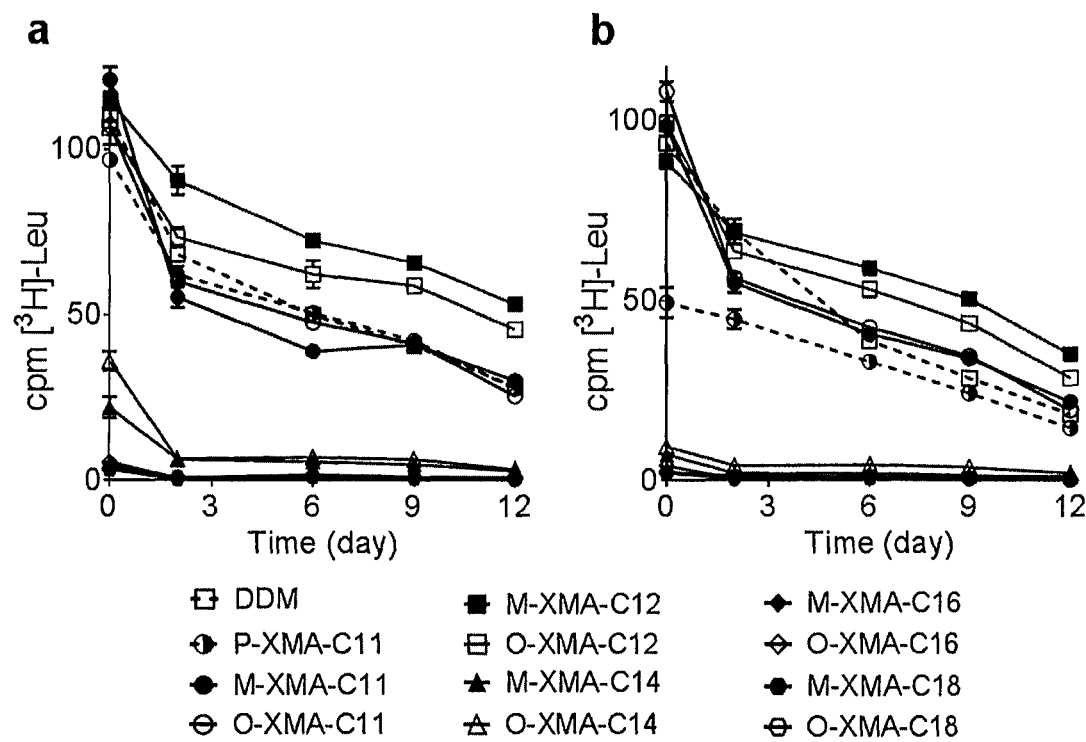

[Fig. 40]
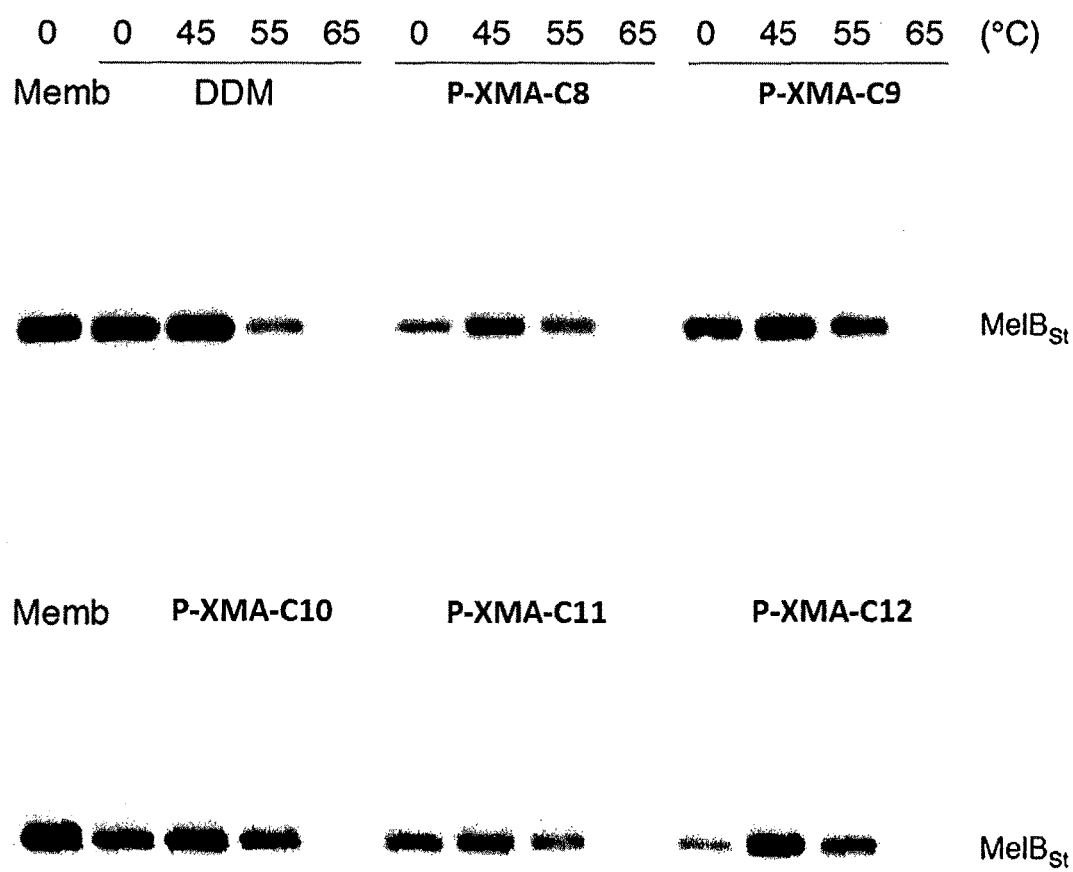

[Fig. 41]
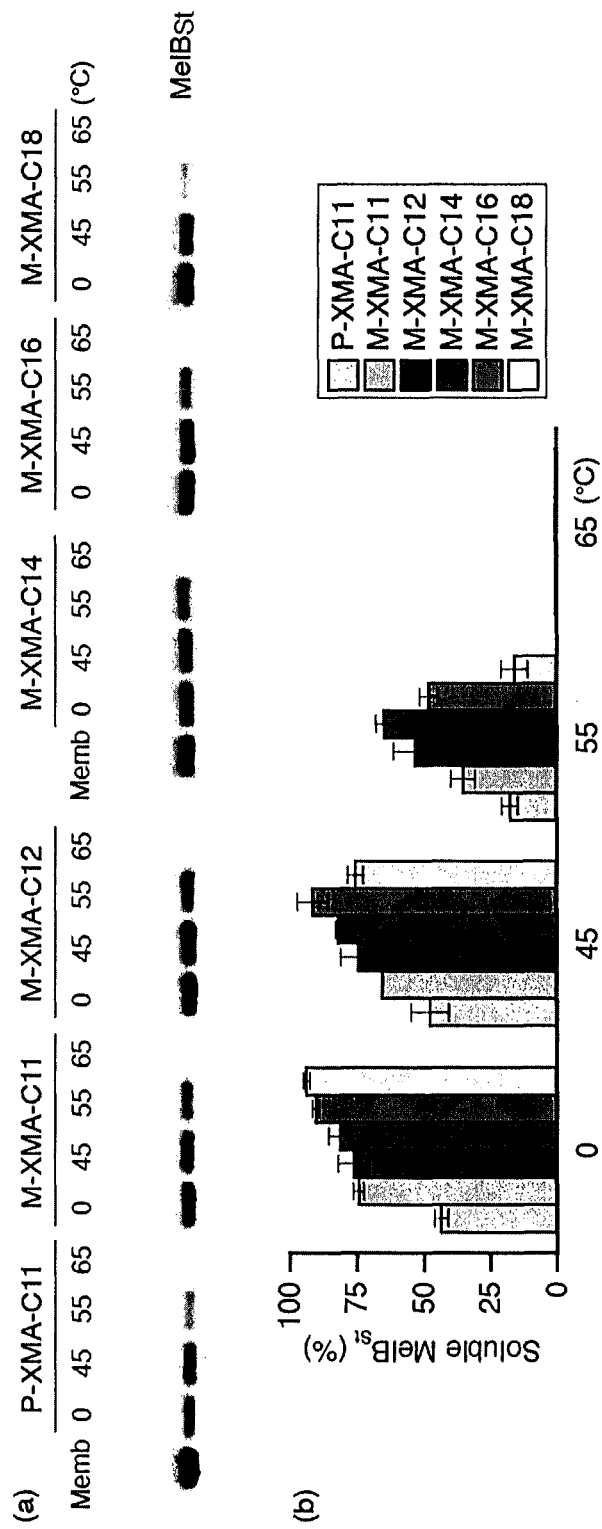

[Fig. 42]
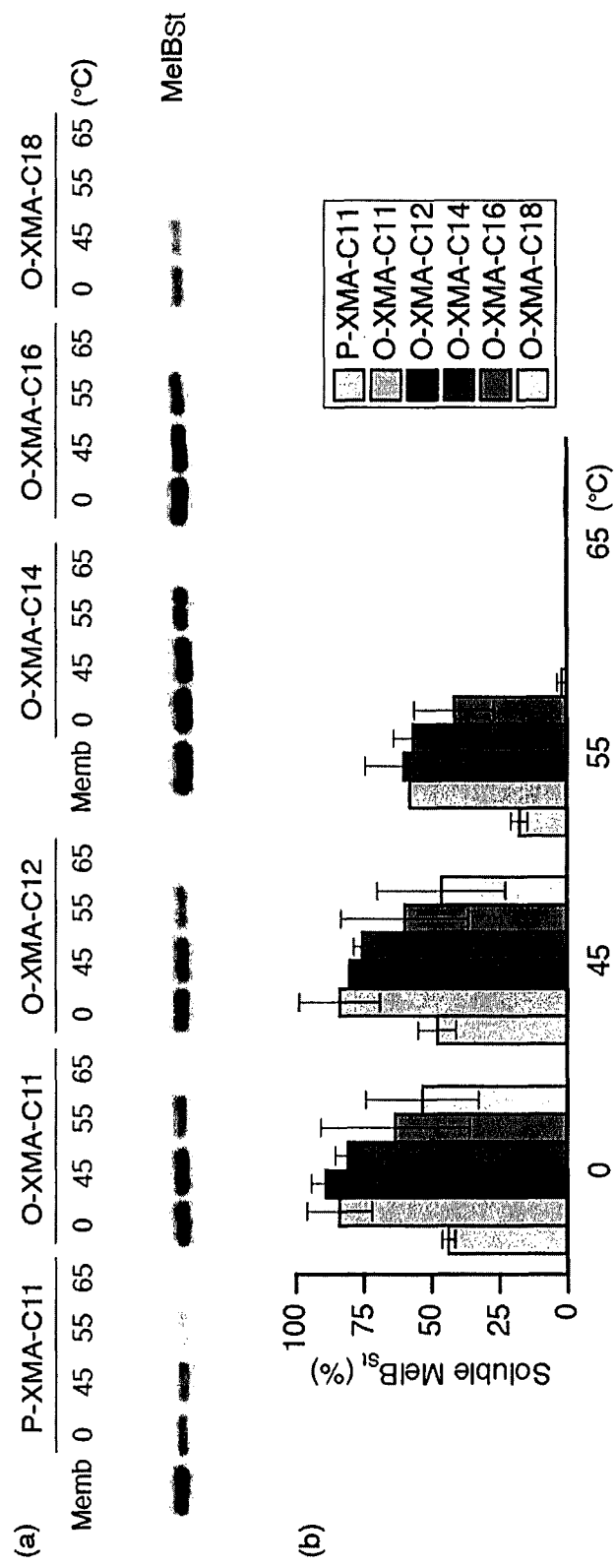

[Fig. 43a]
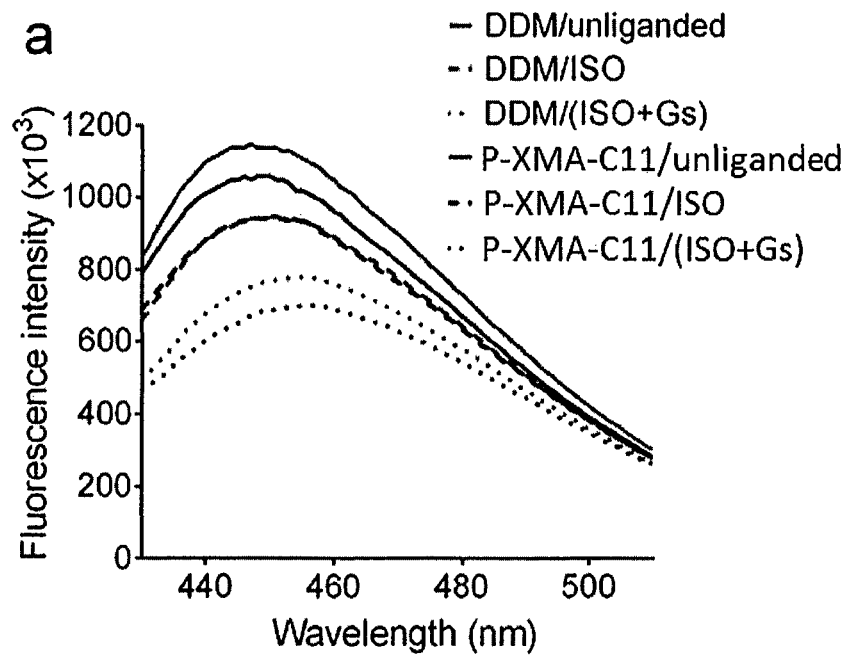
[Fig. 43b]
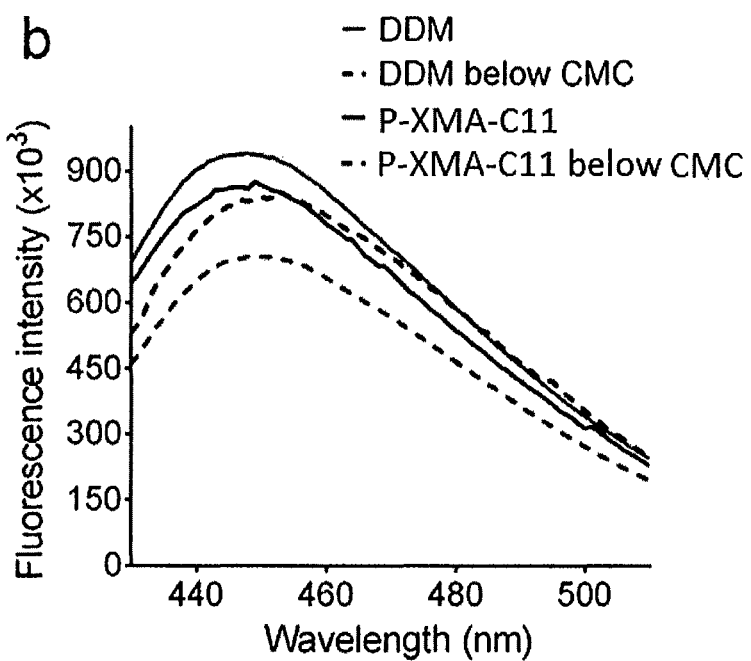

[Fig. 43c]
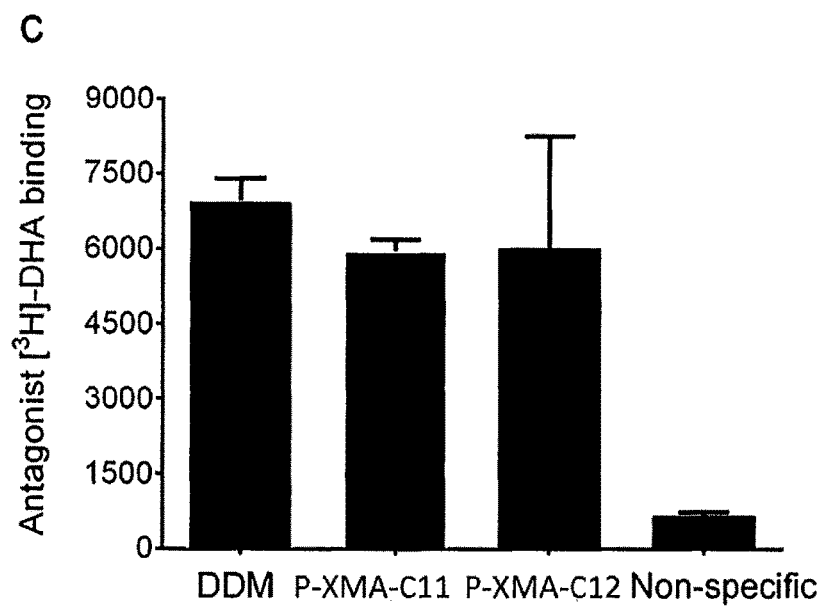
[Fig. 44]
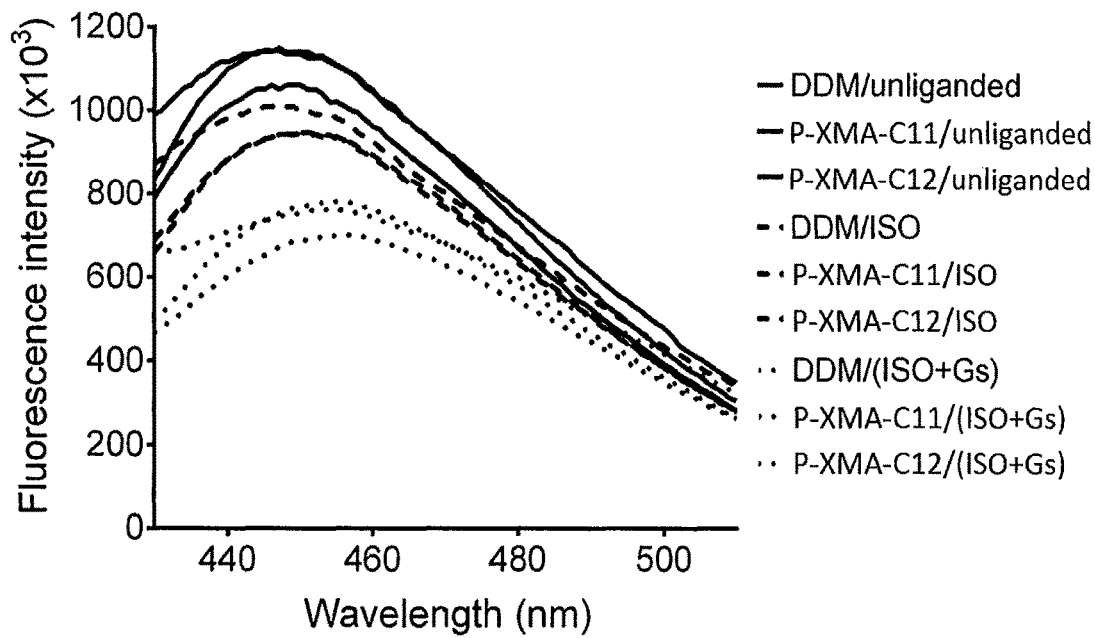

[Fig. 45]
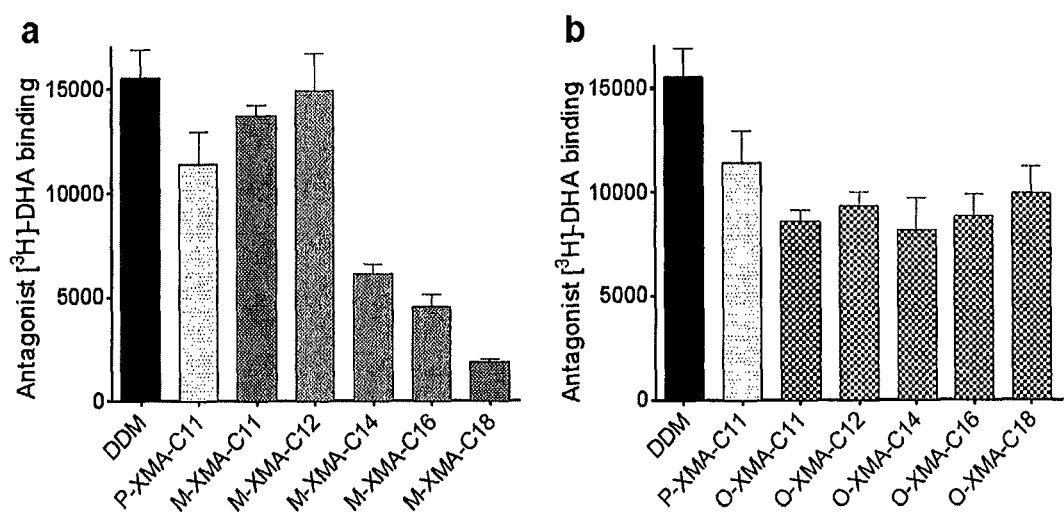

XYLENE-BASED AMPHIPHILIC COMPOUND AND USE THEREOF

CROSS-REFERENCE TO RELATED APPLICATION

This application claims priority to and the benefit of Korean Patent Application Nos. 10-2015-0124705 filed Sep. 3, 2015 and 10-2016-0045394 filed Apr. 14, 2016, both are incorporated herein by reference in their entirety.

BACKGROUND

1. Field of the Invention

The present invention relates to a newly-developed xylene-based amphiphilic compound, and a method for extracting, solubilizing, stabilizing, crystallizing or analyzing a membrane protein using the same.

2. Discussion of Related Art

Membrane proteins are essential for biological systems. Since such bio-macromolecules include hydrophilic and hydrophobic domains, an amphipathic molecule is necessary to extract membrane proteins from a cell membrane, and solubilize and stabilize the proteins in an aqueous solution. For structural analysis of a membrane protein, good-quality membrane protein crystals should be obtained, and to this end, structural stability of a membrane protein in an aqueous solution is required. While there are over a hundred amphiphilic molecules that have been conventionally used in research on membrane proteins, only five of them have been widely used in research on the structure of membrane proteins. These five amphiphilic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Document 1 and Non-Patent Document 2). However, since many membrane proteins enclosed by these molecules tend to be easily denatured and aggregated, thereby rapidly losing their function, there are considerable limitations to research on the function and structure of membrane proteins using such molecules. It is because conventional molecules have a simple chemical structure and thus do not exhibit various characteristics. Therefore, it is necessary to develop a novel amphiphile having novel and excellent characteristics due to a new structure.

Therefore, the inventors developed an amphiphilic compound which can be used in research on membrane proteins, and thus completed the present invention.

(Non-Patent Document 1) S. Newstead et al., *Protein Sci.* 17 (2008) 466-472.

(Non-Patent Document 2) S. Newstead et al., *Mol. Membr. Biol.* 25 (2008) 631-638.

SUMMARY OF THE INVENTION

The present invention is directed to providing a compound represented by Formula 1.

The present invention is also directed to providing a composition for extracting, solubilizing, stabilizing, crystallizing or analyzing a membrane protein, which includes the above-mentioned compound.

The present invention is also directed to providing a method for preparing the above-mentioned compound.

The present invention is also directed to providing a method for extracting, solubilizing, stabilizing, crystallizing or analyzing a membrane protein using the above-mentioned compound.

In one aspect, the present invention provides a compound represented by Formula 1:

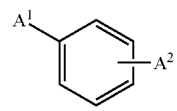

[Formula 1]

In Formula 1, the position of $A^2$, relative to $A^1$, may be ortho, meta or para;

$A^1$ and $A^2$ may be the same or different, and may be each independently represented by Formula 2 below;

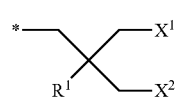

[Formula 2]

$R^1$ may be a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;

$X^1$ and $X^2$ may be each independently a saccharide linked by an oxygen atom; and the symbol * in Formula 2 may represent a part linked to the core structure of Formula 1.

The term "saccharide" used herein refers to a carbohydrate compound which is a relatively small molecule with a sweet taste when solubilized in water. The saccharide is classified into a monosaccharide, a disaccharide or a polysaccharide according to the number of molecules constituting a sugar.

The saccharide used in the embodiment may be a monosaccharide or a disaccharide, and specifically, glucose or maltose, but the present invention is not limited thereto.

The saccharide may act as a hydrophilic group. The compound according to one embodiment of the present invention has a smaller size when forming a complex with a membrane protein by increasing a size of a hydrophilic group and minimizing an increase in length due to parallel linkage of four saccharides, which are hydrophilic groups. When the size of the complex of the compound and the membrane protein is small, good-quality membrane protein crystals may be obtained (G. G. Prive, *Methods* 2007, 41, 388-397).

In addition, $R^1$ may act as a hydrophobic group. In the compound according to one embodiment of the present invention, two alkyl groups may be introduced as hydrophobic groups to optimize hydrophile-lipophile balance.

The compound according to an embodiment of the present invention may have structurally rigid xylene, specifically, a p-xylene (p-dimethylbenzene), m-xylene (m-dimethylbenzene) or o-xylene (o-dimethylbenzene) linker. That is, as two quaternary carbons are introduced into xylene terminals, flowability of the entire molecules may be highly limited, resulting in the promotion of the crystallization of the membrane protein.

Specifically, $A^1$ and $A^2$ may be the same as each other; $R^1$ may be a substituted or unsubstituted $C_3$-$C_{26}$ alkyl group; and $X^1$ and $X^2$ may be oxygen-linked maltoses. In one embodiment of the present invention, such compounds are named "xylene-linked maltoside amphiphiles (XMAs)."

More specifically, the position of $A^2$, relative to $A^1$, may be para; $A^1$ and $A^2$ may be the same as each other; $R^1$ may be a substituted or unsubstituted $C_3$-$C_{26}$ alkyl group; and $X^1$ and $X^2$ may be oxygen-linked maltoses. In one embodiment of the present invention, such compounds are named "para-xylene-linked maltoside amphiphiles (P-XMAs)."

In addition, the position of $A^2$, relative to $A^1$, may be meta; $A^1$ and $A^2$ may be the same as each other; $R^1$ may be a substituted or unsubstituted $C_3$-$C_{26}$ alkyl group; and $X^1$ and $X^2$ may be oxygen-linked maltoses. In one embodiment of the present invention, such compounds were named "meta-xylene-linked maltoside amphiphiles (M-XMAs)."

In addition, the position of $A^2$, relative to $A^1$, may be ortho; $A^1$ and $A^2$ may be the same as each other; $R^1$ may be a substituted or unsubstituted $C_3$-$C_{26}$ alkyl group; and $X^1$ and $X^2$ may be oxygen-linked maltoses. In one embodiment of the present invention, such compounds are named "ortho-xylene-linked maltoside amphiphiles (O-XMAs)."

In one embodiment of the present invention, a compound in which the position of $A^2$, relative to $A^1$, may be para; $A^1$ and $A^2$ may be the same as each other; $R^1$ may be a $C_8$ alkyl group; and $X^1$ and $X^2$ may be oxygen-linked maltoses is named "P-XMA-C8." Therefore, the compound may be a compound represented by Formula 3 below:

[Formula 3]

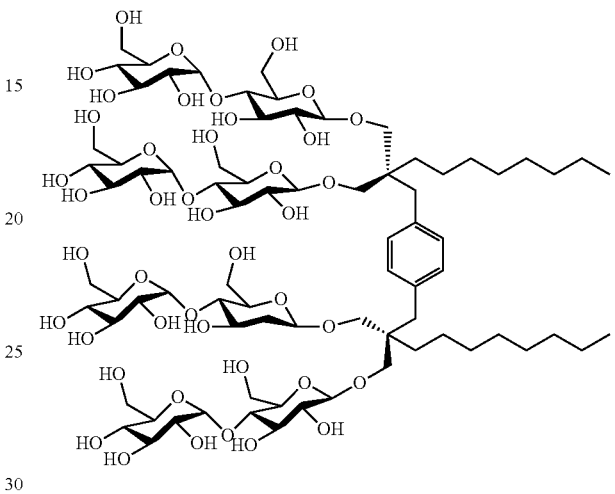

In another embodiment of the present invention, a compound in which the position of $A^2$, relative to $A^1$, may be para; $A^1$ and $A^2$ may be the same as each other; $R^1$ may be a $C_9$ alkyl group; and $X^1$ and $X^2$ may be oxygen-linked maltoses is named "P-XMA-C9." Therefore, the compound may be a compound represented by Formula 4 below:

[Formula 4]

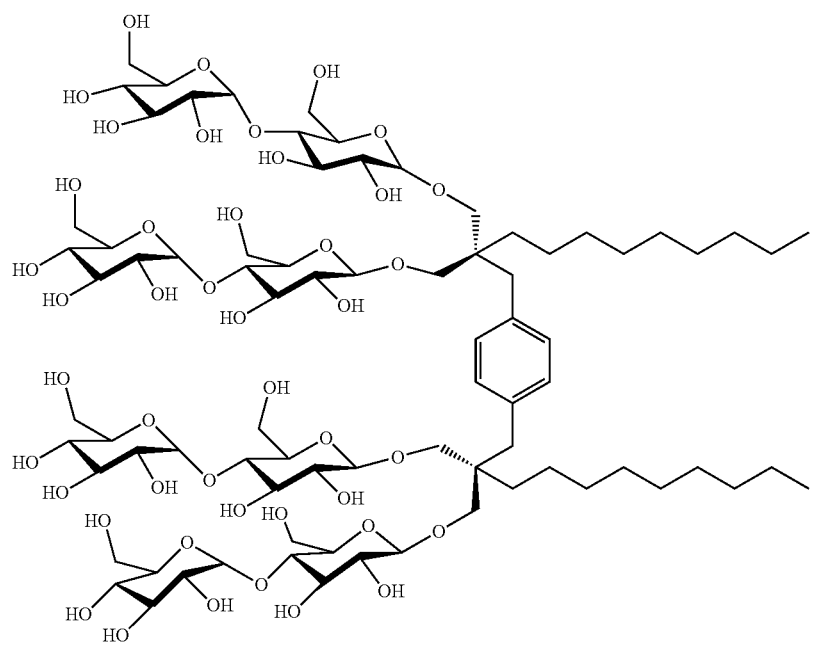

In still another embodiment of the present invention, a compound in which the position of $A^2$, relative to $A^1$, may be para; $A^1$ and $A^2$ may be the same as each other; $R^1$ may be a $C_{10}$ alkyl group; and $X^1$ and $X^2$ may be oxygen-linked maltoses is named "P-XMA-C10." Therefore, the compound may be a compound represented by Formula 5 below:

[Formula 5]

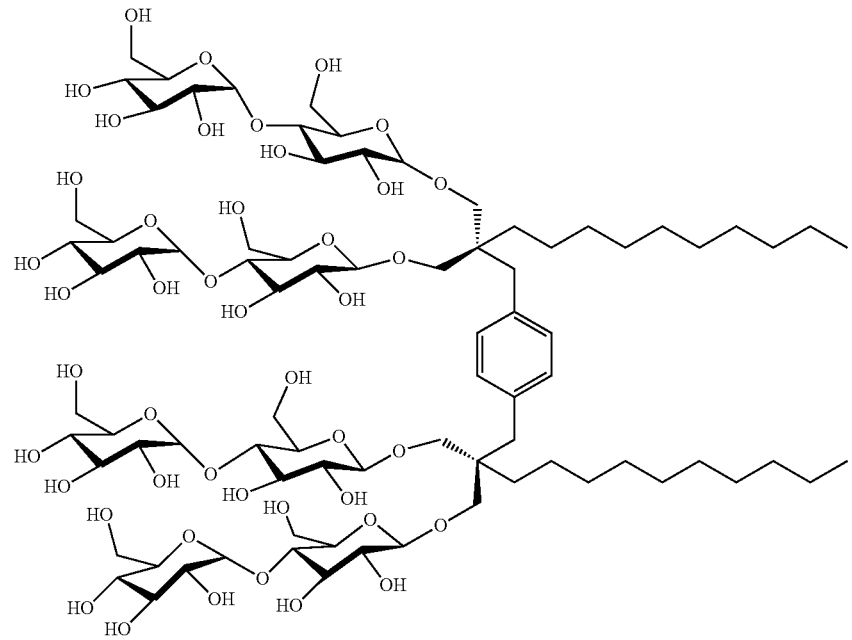

In yet another embodiment of the present invention, a compound in which the position of $A^2$, relative to $A^1$, may be para; $A^1$ and $A^2$ may be the same as each other; $R^1$ may be a $C_{11}$ alkyl group; and $X^1$ and $X^2$ may be oxygen-linked maltoses is named "P-XMA-C11." Therefore, the compound may be a compound represented by Formula 6 below:

[Formula 6]

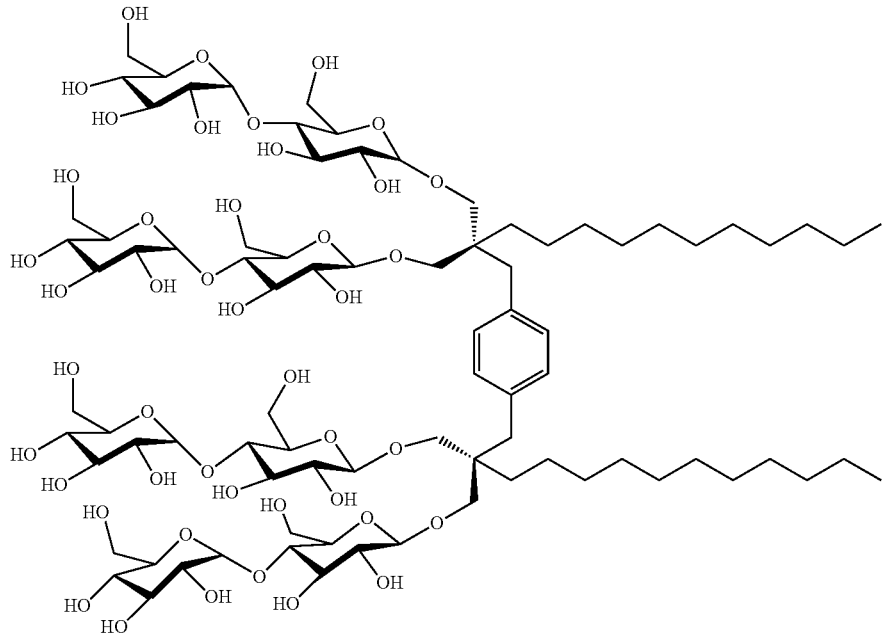

In yet another embodiment of the present invention, a compound in which the position of $A^2$, relative to $A^1$, may be para; $A^1$ and $A^2$ may be the same as each other; $R^1$ may be a $C_{12}$ alkyl group; and $X^1$ and $X^2$ may be oxygen-linked maltoses is named "P-XMA-C12." Therefore, the compound may be a compound represented by Formula 7 below:

[Formula 7]

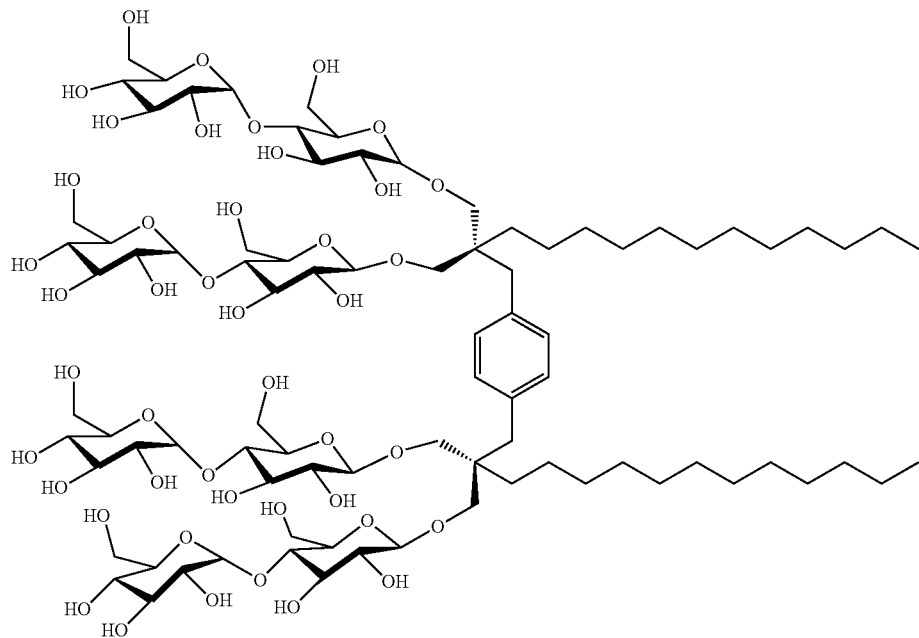

In yet another embodiment of the present invention, a compound in which the position of $A^2$, relative to $A^1$, may be meta; $A^1$ and $A^2$ may be the same as each other; $R^1$ may be a $C_{11}$ alkyl group; and $X^1$ and $X^2$ may be oxygen-linked maltoses is named "M-XMA-C11." Therefore, the compound may be a compound represented by Formula 8 below:

[Formula 8]

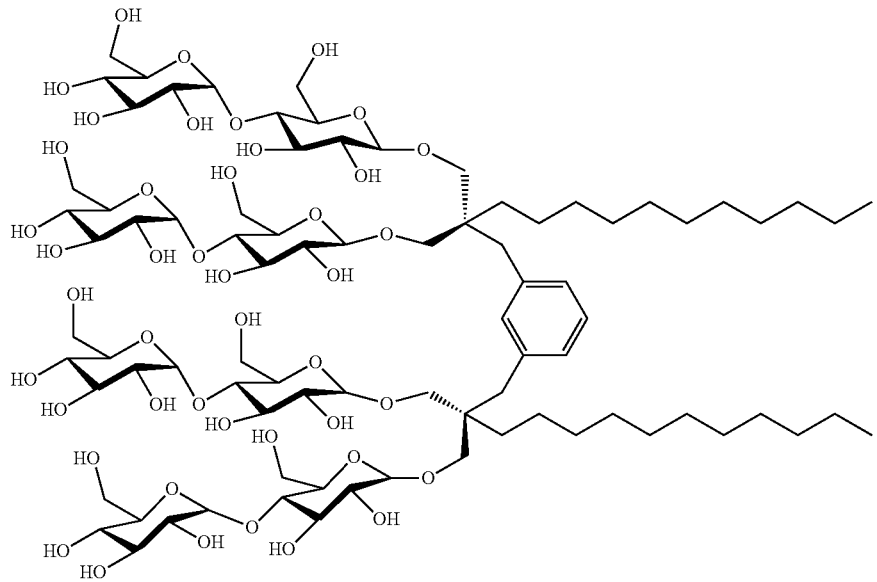

In yet another embodiment of the present invention, a compound in which the position of $A^2$, relative to $A^1$, may be meta; $A^1$ and $A^2$ may be the same as each other; $R^1$ may be a $C_{12}$ alkyl group; and $X^1$ and $X^2$ may be oxygen-linked maltoses is named "M-XMA-C12." Therefore, the compound may be a compound represented by Formula 9 below:

[Formula 9]

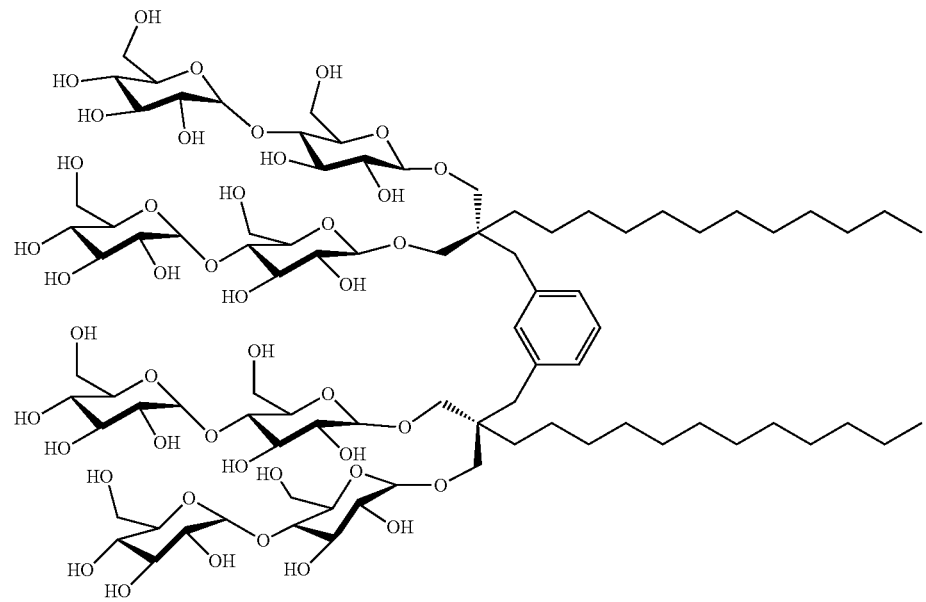

In yet another embodiment of the present invention, a compound in which the position of $A^2$, relative to $A^1$, may be meta; $A^1$ and $A^2$ may be the same as each other; $R^1$ may be a $C_{14}$ alkyl group; and $X^1$ and $X^2$ may be oxygen-linked maltoses is named "M-XMA-C14." Therefore, the compound may be a compound represented by Formula 10 below:

[Formula 10]

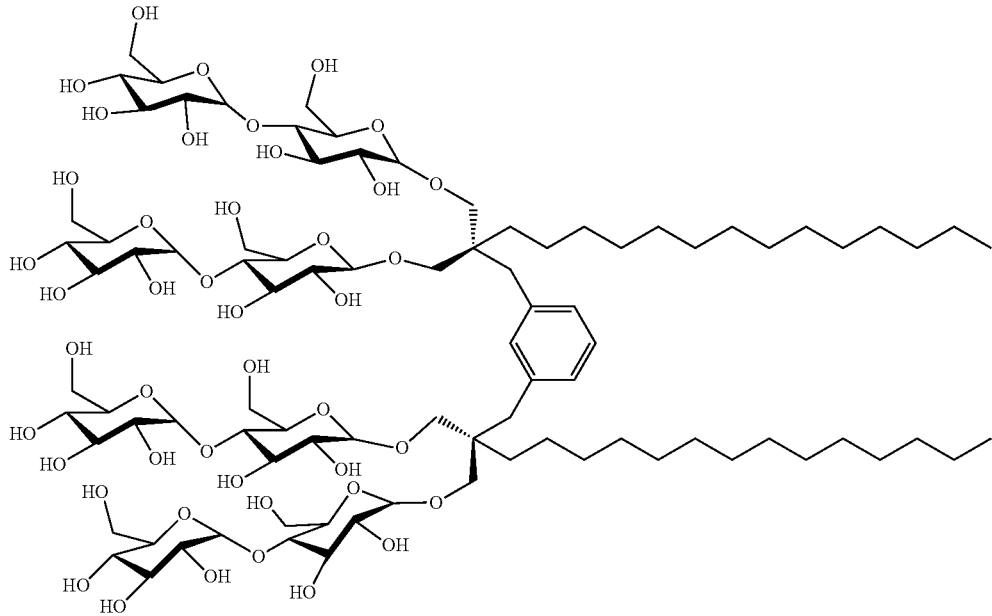

In yet another embodiment of the present invention, a compound in which the position of $A^2$, relative to $A^1$, may be meta; $A^1$ and $A^2$ may be the same as each other; $R^1$ may be a $C_{16}$ alkyl group; and $X^1$ and $X^2$ may be oxygen-linked maltoses is named "M-XMA-C16." Therefore, the compound may be a compound represented by Formula 11 below:

[Formula 11]

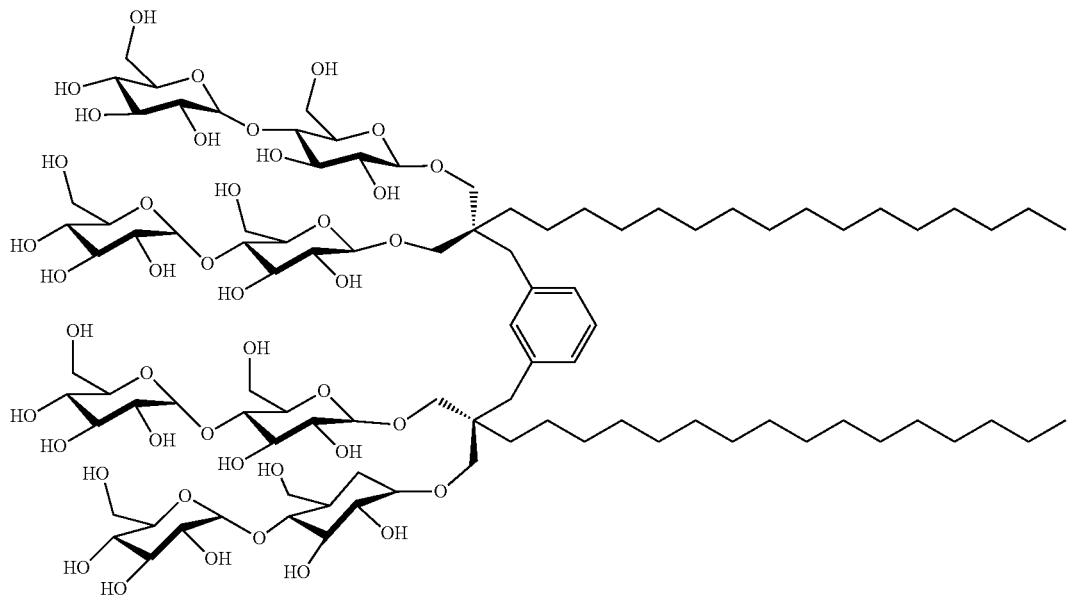

In yet another embodiment of the present invention, a compound in which the position of $A^2$, relative to $A^1$, may be meta; $A^1$ and $A^2$ may be the same as each other; $R^1$ may be a $C_{18}$ alkyl group; and $X^1$ and $X^2$ may be oxygen-linked maltoses is named "M-XMA-C18." Therefore, the compound may be a compound represented by Formula 12 below:

[Formula 12]

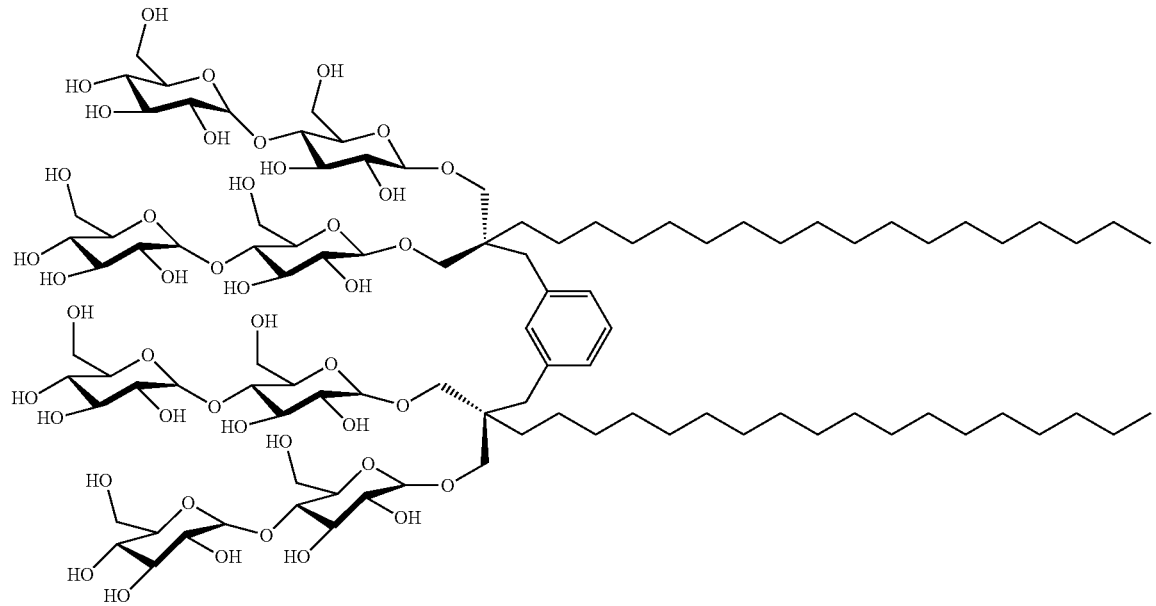

In yet another embodiment of the present invention, a compound in which the position of $A^2$, relative to $A^1$, may be ortho; $A^1$ and $A^2$ may be the same as each other; $R^1$ may be a $C_{11}$ alkyl group; and $X^1$ and $X^2$ may be oxygen-linked maltoses is named "O-XMA-C11." Therefore, the compound may be a compound represented by Formula 13 below:

[Formula 13]

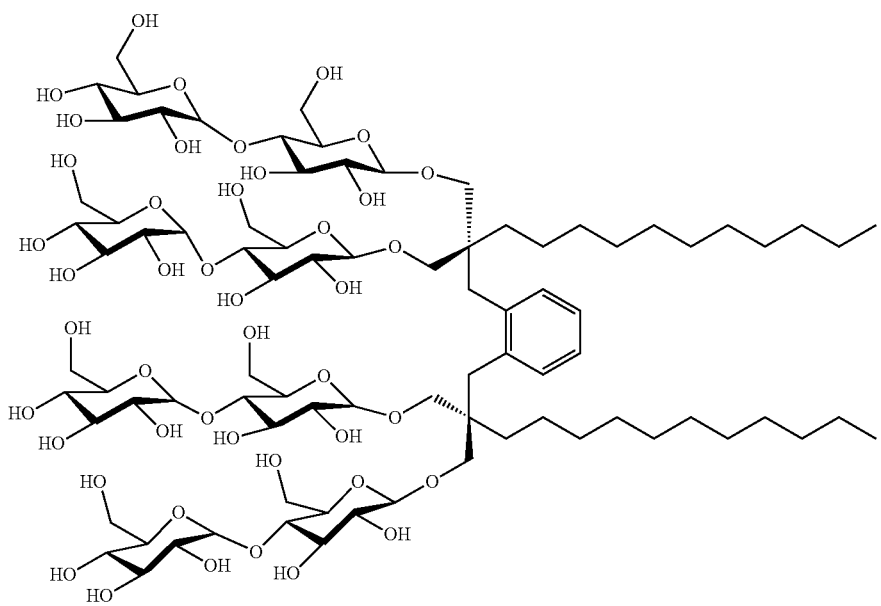

In yet another embodiment of the present invention, a compound in which the position of $A^2$, relative to $A^1$, may be ortho; $A^1$ and $A^2$ may be the same as each other; $R^1$ may be a $C_{12}$ alkyl group; and $X^1$ and $X^2$ may be oxygen-linked maltoses is named "O-XMA-C12." Therefore, the compound may be a compound represented by Formula 14 below:

[Formula 14]

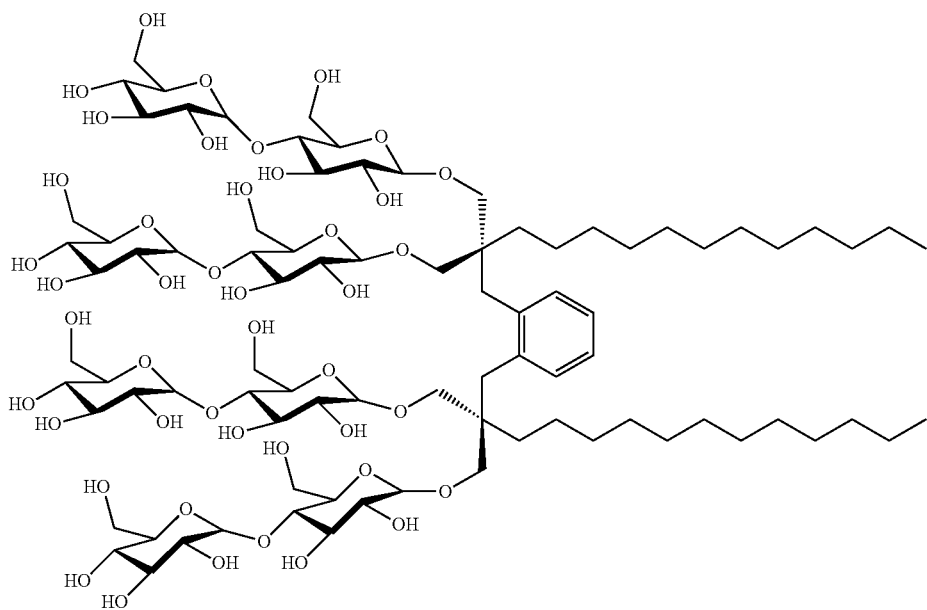

In yet another embodiment of the present invention, a compound in which the position of $A^2$, relative to $A^1$, may be ortho; $A^1$ and $A^2$ may be the same as each other; $R^1$ may be a $C_{14}$ alkyl group; and $X^1$ and $X^2$ may be oxygen-linked maltoses is named "O-XMA-C14." Therefore, the compound may be a compound represented by Formula 15 below:

[Formula 15]

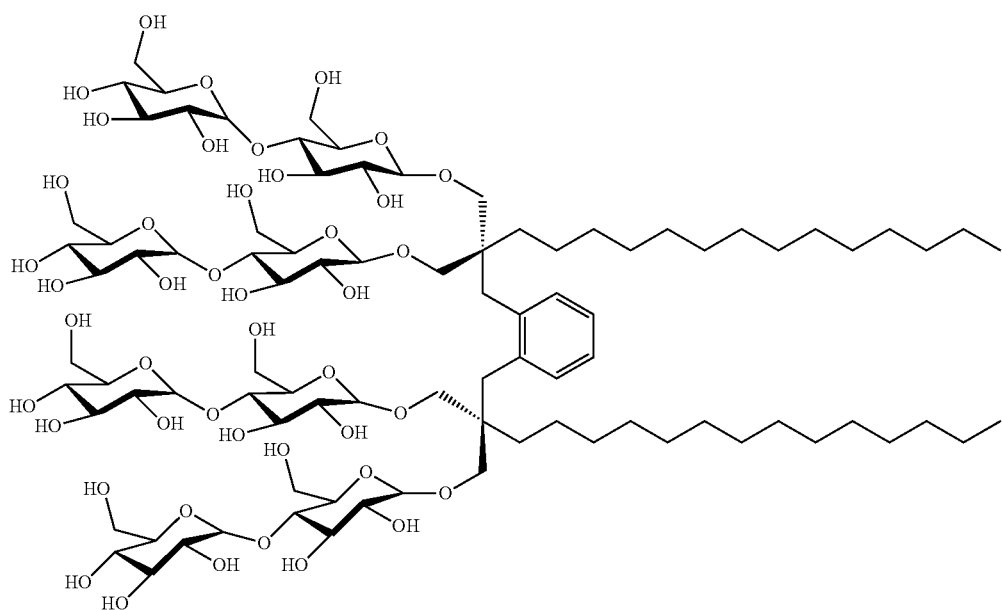

In yet another embodiment of the present invention, a compound in which the position of $A^2$, relative to $A^1$, may be ortho; $A^1$ and $A^2$ may be the same as each other; $R^1$ may be a $C_{16}$ alkyl group; and $X^1$ and $X^2$ may be oxygen-linked maltoses is named "O-XMA-C16." Therefore, the compound may be a compound represented by Formula 16 below:

[Formula 16]

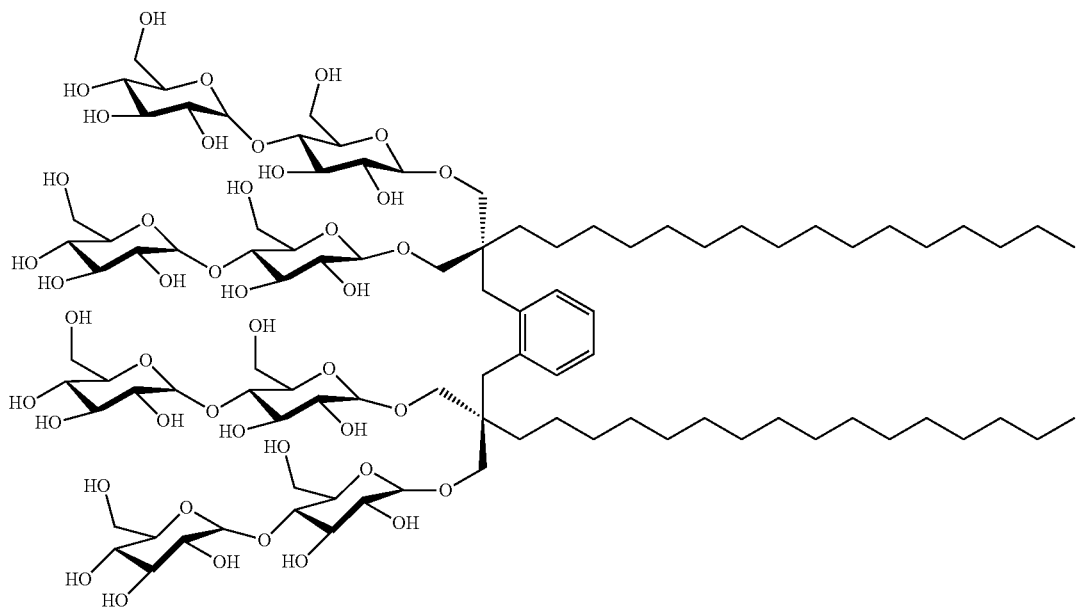

In yet another embodiment of the present invention, a compound in which the position of $A^2$, relative to $A^1$, may be ortho; $A^1$ and $A^2$ may be the same as each other; $R^1$ may be a $C_{18}$ alkyl group; and $X^1$ and $X^2$ may be oxygen-linked maltoses is named "O-XMA-C18." Therefore, the compound may be a compound represented by Formula 17 below:

[Formula 17]

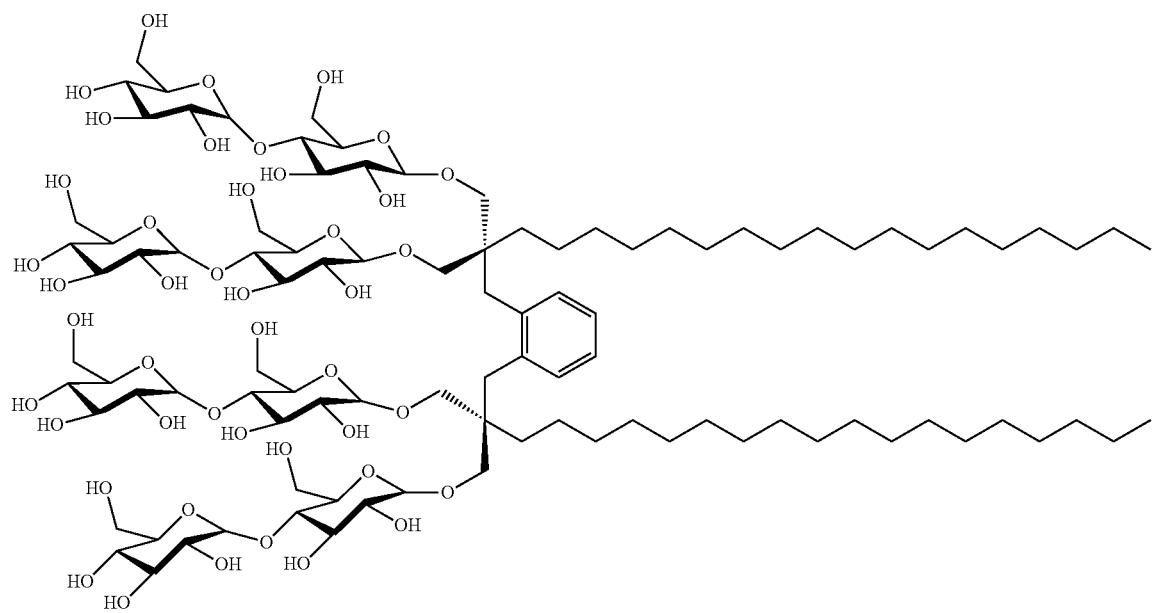

In addition, $A^1$ and $A^2$ may be the same as each other; $R^1$ may be a substituted or unsubstituted $C_3$-$C_{26}$ alkyl group; and $X^1$ and $X^2$ may be oxygen-linked glucoses. In an embodiment of the present invention, such compounds are named "xylene-linked glucoside amphiphiles (XGAs)." More specifically, here, when the position of $A^2$, relative to $A^1$, is para, the compounds are named "para-xylene-linked glucoside amphiphiles (P-XGAs)," when the position of $A^2$, relative to $A^1$, is meta, the compounds are named "meta-xylene-linked glucoside amphiphiles (M-XGAs)," and when the position of $A^2$, relative to $A^1$, is ortho, the compounds are named "ortho-xylene-linked glucoside amphiphiles (O-XGAs)."

In one embodiment of the present invention, a compound in which the position of $A^2$, relative to $A^1$, may be para; $A^1$ and $A^2$ may be the same as each other; $R^1$ may be a $C_4$ alkyl group; and $X^1$ and $X^2$ are oxygen-linked glucoses is named "P-XGA-C4." Therefore, the compound may be a compound represented by Formula 18 below:

[Formula 18]

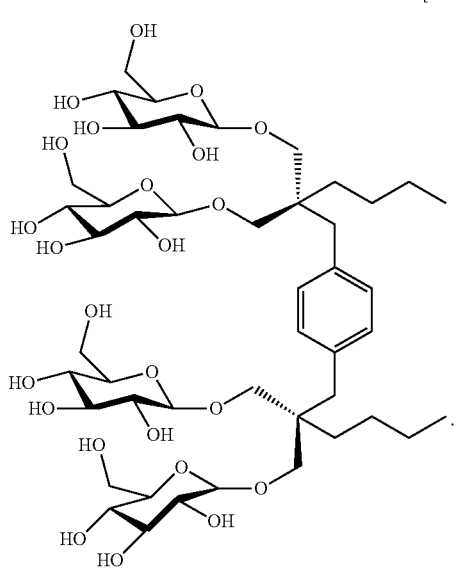

In another embodiment of the present invention, a compound in which the position of $A^2$, relative to $A^1$, may be para; $A^1$ and $A^2$ may be the same as each other; $R^1$ may be a $C_5$ alkyl group; and $X^1$ and $X^2$ are oxygen-linked glucoses is named "P-XGA-C5." Therefore, the compound may be a compound represented by Formula 19 below:

[Formula 19]

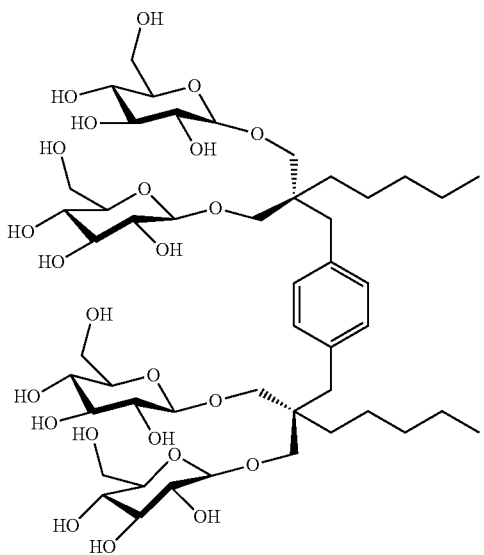

In still another embodiment of the present invention, a compound in which the position of $A^2$, relative to $A^1$, may be para; $A^1$ and $A^2$ may be the same as each other; $R^1$ may be a $C_6$ alkyl group; and $X^1$ and $X^2$ are oxygen-linked glucoses is named "P-XGA-C6." Therefore, the compound may be a compound represented by Formula 20 below:

[Formula 20]

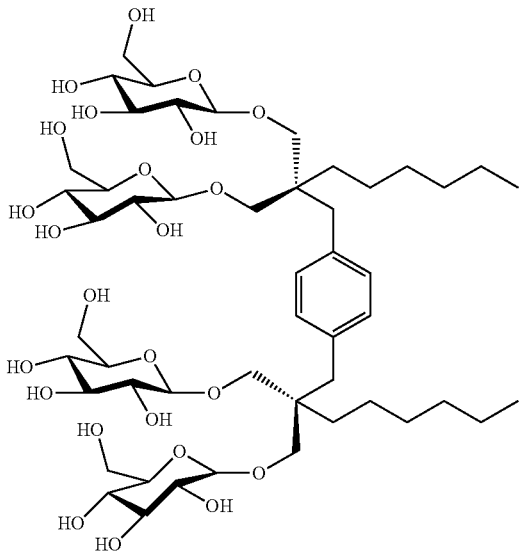

The compound according to another embodiment of the present invention may be an amphiphilic molecule for extracting, solubilizing, stabilizing, crystallizing or analyzing a membrane protein, but the present invention is not limited thereto.

The term "amphiphilic molecule" used herein refers to a molecule having both a hydrophobic group and a hydrophilic group in one molecule, and having affinity for polar and non-polar solvents. Phospholipid molecules present in a surfactant or a cell membrane have a hydrophilic group at one end and a hydrophobic group at the other end, have amphiphilicity and form micelles or liposomes in an aqueous solution. Since the amphiphilic molecules have a hydrophilic group, which is polar, but a non-polar group is present, they tend to be poorly soluble in water. However, when a concentration exceeds a limit concentration (critical micelle concentration, CMC), hydrophobic groups are collected inside due to a hydrophobic interaction, a micelle in which hydrophilic groups are directed to the surface is produced, resulting in an increase in solubility in water.

While a method for measuring CMC is not particularly limited, a method widely known in the art may be used, and the measurement may be performed by, for example, a fluorescence staining method using diphenylhexatriene (DPH).

A compound according to an exemplary embodiment of the present invention may have a CMC in an aqueous solution of 0.1 μM to 1000 μM, and specifically, 0.1 μM to 100 μM, more specifically, 0.1 μM to 50 μM, further more specifically, 0.1 μM to 30 further more specifically, 0.5 μM to 30 μM, and for example, 0.1 μM to 25 μM or 0.5 μM to 25 μM, but the present invention is not limited thereto.

As compared with DDM, which has been generally used in conventional research on a membrane protein, having a CMC of 170 μM, the XMAs of the embodiment have very small CMC values. Therefore, since a micelle is easily formed with a small amount of XMAs, the membrane protein may be effectively studied and analyzed using a small amount of XMAs, confirming that XMAs are superior to DDM.

Another aspect of the present invention provides a composition for extracting, solubilizing, stabilizing, crystallizing or analyzing a membrane protein including the above-described compound.

The composition may be prepared in the form of a micelle, a liposome, an emulsion or a nanoparticle, but the present invention is not limited thereto.

The micelle may have a radius of 2.0 nm to 4.5 nm, specifically, 2.0 nm to 4.4 nm, more specifically, 2.1 to 4.3 nm, and for example, 2.2 nm to 4.2 nm, but the present invention is not limited thereto.

A method for measuring the radius of a micelle is not particularly limited, but a method well known in the art may be used, and for example, the measurement may be performed using a dynamic light scattering (DLS) experiment.

As compared with DDM having a radius of 3.4 nm, XMAs also have a micelle with a similar size to that of DDM, and it can be confirmed that a novel molecule has a geometrical shape in an aqueous solution, which is similar to that of DDM.

The micelle, liposome, emulsion or nanoparticle may include a membrane protein therein. That is, the membrane protein present inside the cell membrane may be extracted by being enclosed by the micelle, liposome, emulsion or nanoparticle. Therefore, it is possible to extract, solubilize, stabilize, crystallize or analyze the membrane protein by the micelle.

The composition may further include a buffer that is helpful in extracting, solubilizing, stabilizing, crystallizing or analyzing the membrane protein.

Still another aspect of the present invention provides a method for preparing a compound represented by Formula 1 below, the method including steps 1) to 5) as follows:

1) introducing an alkyl group by performing monoalkylation on diethyl malonate;

2) introducing a xylene linker by coupling the product of step 1) with bis(bromomethyl)benzene;

3) reducing an ester functional group of the product of step 2) into an alcohol functional group;
4) introducing a protective group-attached saccharide by performing glycosylation on the product of step 3); and
5) performing deprotection on the product of step 4).

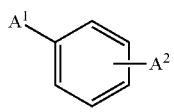

[Formula 1]

In Formula 1,
the position of $A^2$, relative to $A^1$, may be ortho, meta or para; $A^1$ and $A^2$ may be the same or different, and may be each independently represented by Formula 2 below;

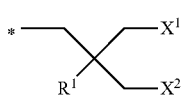

[Formula 2]

$R^1$ may be a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;
$X^1$ and $X^2$ may be each independently saccharides linked by an oxygen atom; and
the symbol * in Formula 2 may represent a part linked to the core structure of Formula 1.

The bis(bromomethyl)benzene in Step 2) may be p-bis(bromomethyl)benzene, m-bis(bromomethyl)benzene or o-bis(bromomethyl)benzene.

Specifically, $A^1$ and $A^2$ may be the same as each other; $R^1$ may be a substituted or unsubstituted $C_3$-$C_{26}$ alkyl group; and $X^1$ and $X^2$ may be oxygen-linked maltoses.

In addition, $A^1$ and $A^2$ may be the same as each other; $R^1$ may be a substituted or unsubstituted $C_3$-$C_{26}$ alkyl group; and $X^1$ and $X^2$ may be oxygen-linked glucoses.

The compound may be a compound represented by any one of Formulas 3 to 20 according to an exemplary embodiment of the present invention, but the present invention is not limited thereto.

In this embodiment, the compound may be synthesized from diethyl malonate, which can be easily obtained, by a simple method. Since the compound can be easily synthesized according to the preparation method of the present invention, it is possible to produce a large amount of the compound to study a membrane protein.

In one embodiment of the present invention, XMAs are prepared by performing the following steps according to a synthesis scheme illustrated in FIG. 1, 3 or 4:
1) Compound A is obtained by adding 1-bromoalkane, $K_2CO_3$, THF, and DMF to diethyl malonate and performing monoalkylation.
2) Product B into which a xylene linker is introduced is obtained by adding NaH, bis(bromomethyl)benzene [p-bis(bromomethyl)benzene, m-bis(bromomethyl)benzene or o-bis(bromomethyl)benzene], THF and DMF to Compound A.
3) Compound C is obtained by adding $LiAlH_4$ and THF to Product B to reduce an ester functional group into an alcohol functional group.
4) Product D into which a protection group-attached saccharide is introduced is obtained by adding perbenzoylated maltosylbromide, AgOTf and $CH_2Cl_2$ to Product C and performing glycosylation.

5) Product E (XMAs) is obtained by adding NaOMe and MeOH to Product D and performing deprotection.

In one embodiment of the present invention, P-XGA-C4 to P-XGA-C6 are prepared by performing the following steps according to the synthesis scheme illustrated in FIG. 1:
1) Compound A is obtained by adding 1-bromoalkane, $K_2CO_3$, THF and DMF to diethyl malonate and performing monoalkylation.
2) Product B into which a xylene linker is introduced is obtained by adding NaH, bis(bromomethyl)benzene [p-bis(bromomethyl)benzene], THF and DMF to Compound A.
3) Compound C is obtained by adding $LiAlH_4$ and THF to Product B to reduce an ester functional group into an alcohol functional group.
4) Product D into which a protection group-attached saccharide is introduced is obtained by adding perbenzoylated glucosylbromide, AgOTf, $CH_2Cl_2$ and 2,4,6-collidine to Product C and performing glycosylation.
5) Product E (XMAs) is obtained by adding NaOMe and MeOH to Product D and performing deprotection.

A yet another aspect of the present invention provides a method for extracting, solubilizing, stabilizing, crystallizing or analyzing a membrane protein. Specifically, the present invention provides a method for extracting, solubilizing, stabilizing, crystallizing or analyzing a membrane protein, the method including treating a membrane protein with a compound represented by Formula 1 in an aqueous solution:

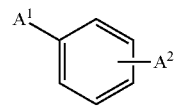

[Formula 1]

In Formula 1,
the position of $A^2$, relative to $A^1$, may be ortho, meta or para;
$A^1$ and $A^2$ may be the same or different, and may be each independently represented by Formula 2 below;

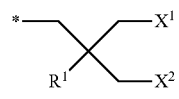

[Formula 2]

$R^1$ may be a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;
$X^1$ and $X^2$ may be each independently saccharides linked by an oxygen atom; and
the symbol * in Formula 2 may represent a part linked to the core structure of Formula 1.

Specifically, $A^1$ and $A^2$ may be the same as each other; $R^1$ may be a substituted or unsubstituted $C_3$-$C_{26}$ alkyl group; and $X^1$ and $X^2$ may be oxygen-linked maltoses.

In addition, $A^1$ and $A^2$ may be the same as each other; $R^1$ may be a substituted or unsubstituted $C_3$-$C_{26}$ alkyl group; and $X^1$ and $X^2$ may be oxygen-linked glucoses.

The compound may be a compound represented by any one of Formulas 3 to 20 according to an exemplary embodiment of the present invention, but the present invention is not limited thereto.

The term "membrane protein" used herein refers to the generic term for proteins or glycoproteins introduced into a cell membrane lipid bilayer. It is present in various states, for example, passing through the entire layer of the cell membrane, on the surface of the cell membrane, or attached to the cell membrane. Examples of the membrane protein include a receptor such as an enzyme, a peptide hormone or a local hormone, a receptor carrier such as a sugar, an ion channel, and an antigen for a cell membrane, but the present invention is not limited thereto.

The membrane protein includes any protein or glycoprotein introduced into the lipid bilayer of a cell membrane, and specifically, a boron transporter (Bor1), a leucine transporter (LeuT), melibiose permease (MelB), a human $\beta_2$ adrenergic receptor ($\beta_2$AR) or a combination of two or more thereof, but the present invention is not limited thereto.

The term "extraction of a membrane protein" used herein refers to separation of a membrane protein from a cell membrane.

The term "solubilization of a membrane protein" used herein refers to the solubilization of a water-insoluble membrane protein in an aqueous solution to be solubilized in a micelle.

The term "stabilization of a membrane protein" used herein refers to the stable conservation of a tertiary or quaternary structure without a change in structure and function of a membrane protein.

The term "crystallization of a membrane protein" refers to the formation of crystals of a membrane protein in a solution.

The term "analyzation of a membrane protein" used herein refers to analysis of the structure or function of a membrane protein. In the embodiment, the analysis of a membrane protein may be carried out by a known method, but the present invention is not limited thereto. For example, the structure of a membrane protein may be analyzed by electron microscopy.

By using xylene-based compounds according to exemplary embodiments of the present invention, compared to a conventional compound, a membrane protein can be stably stored in an aqueous solution for a long time, and can be subjected to functional analysis and structural analysis.

Since the structural and functional analysis of a membrane protein is one of the fields of highest interest in biology and chemistry, the compounds according to exemplary embodiments of the present invention can be applied in research on protein structure that is closely related to development of a new drug.

Specifically, the compounds according to exemplary embodiments of the present invention can form a high quality membrane protein crystal due to a small size when a complex with the membrane protein is formed, and have a xylene linker which is structurally rigid and two quaternary carbon atoms introduced at a xylene terminal, thereby greatly limiting the flowability of the total molecule, and therefore the crystallization of the membrane protein can be promoted.

In addition, since the compounds of the present invention can be synthesized from a starting material that can be easily obtained by a simple method, the compounds can be mass-produced for research on a membrane protein.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a diagram illustrating a synthesis scheme of P-XMAs and P-XGAs according to Example 1 of the present invention;

FIG. 2 is a diagram illustrating chemical structures of P-XMAs and P-XGAs according to examples of the present invention;

FIG. 3 is a diagram illustrating a synthesis scheme of M-XMAs according to Example 2 of the present invention;

FIG. 4 is a diagram illustrating a synthesis scheme of O-XMAs according to Example 2 of the present invention;

FIG. 5 is a diagram illustrating chemical structures of M-XMAs and 0-XMAs according to examples of the present invention;

FIG. 6 shows the $^1$H NMR spectrum of P-XMA-C8;
FIG. 7 shows the $^{13}$C NMR spectrum of P-XMA-C8;
FIG. 8 shows the $^1$H NMR spectrum of P-XMA-C9;
FIG. 9 shows the $^{13}$C NMR spectrum of P-XMA-C9;
FIG. 10 shows the $^1$H NMR spectrum of P-XMA-C10;
FIG. 11 shows the $^{13}$C NMR spectrum of P-XMA-C10;
FIG. 12 shows the $^1$H NMR spectrum of P-XMA-C11;
FIG. 13 shows the $^{13}$C NMR spectrum of P-XMA-C11;
FIG. 14 shows the $^1$H NMR spectrum of P-XMA-C12;
FIG. 15 shows the $^{13}$C NMR spectrum of P-XMA-C12;
FIG. 16 shows the $^1$H NMR spectrum of M-XMA-C11;
FIG. 17 shows the $^{13}$C NMR spectrum of M-XMA-C11;
FIG. 18 shows the $^1$H NMR spectrum of M-XMA-C12;
FIG. 19 shows the $^{13}$C NMR spectrum of M-XMA-C12;
FIG. 20 shows the $^1$H NMR spectrum of M-XMA-C14;
FIG. 21 shows the $^{13}$C NMR spectrum of M-XMA-C14;
FIG. 22 shows the $^1$H NMR spectrum of M-XMA-C16;
FIG. 23 shows the $^{13}$C NMR spectrum of M-XMA-C16;
FIG. 24 shows the $^1$H NMR spectrum of M-XMA-C18;
FIG. 25 shows the $^{13}$C NMR spectrum of M-XMA-C18;
FIG. 26 shows the $^1$H NMR spectrum of O-XMA-C11;
FIG. 27 shows the $^{13}$C NMR spectrum of O-XMA-C11;
FIG. 28 shows the $^1$H NMR spectrum of O-XMA-C12;
FIG. 29 shows the $^{13}$C NMR spectrum of O-XMA-C12;
FIG. 30 shows the $^1$H NMR spectrum of O-XMA-C14;
FIG. 31 shows the $^{13}$C NMR spectrum of O-XMA-C14;
FIG. 32 shows the $^1$H NMR spectrum of O-XMA-C16;
FIG. 33 shows the $^{13}$C NMR spectrum of O-XMA-C16;
FIG. 34 shows the $^1$H NMR spectrum of O-XMA-C18;
FIG. 35 shows the $^{13}$C NMR spectrum of O-XMA-C18;

FIG. 36 is a set of graphs illustrating the size distribution of micelles formed by P-XMA-C8 (a), P-XMA-C9 (b), P-XMA-C10 (c), P-XMA-C11 (d), P-XMA-C12 (e), and DDM (f);

FIG. 37 is a set of graphs illustrating the size distribution of micelles formed by M-XMAs (a) and O-XMAs (b). All amphiphilic compounds were used at a concentration of 1.0 wt %;

FIG. 38 is a set of graphs illustrating the structural stability of a boron transporter (Bor1) in an aqueous solution by P-XMAs, measured using a CPM assay:

(a) P-XMAs or DDM concentration: CMC+0.04 wt %; and
(b) P-XMAs or DDM concentration: CMC+0.2 wt %;

FIG. 39 is a set of graphs illustrating the structural stability of a leucine transporter (LeuT) in an aqueous solution by XMAs (P-XMA-C11, M-XMAs, and O-XMAs) or DDM. Protein stability is confirmed by measuring the ligand-binding activity of a receptor through a scintillation proximity assay (SPA). In each amphiphilic compound, LeuT is incubated for 12 days at room temperature, and measured at regular intervals:

(a) XMAs or DDM concentration: CMC+0.04 wt %; and
(b) XMAs or DDM concentration: CMC+0.2 wt %;

FIG. 40 shows results of SDS-PAGE and western blotting, which show the amount and structure of MelB protein extracted at four different temperatures (0, 45, 55 and 65° C.) using 1.5 wt % of P-XMAs or DDM;

FIG. 41 shows results of measuring the amount of MelB protein extracted at four different temperatures (0, 45, 55 and 65° C.) using 1.5 wt % of XMAs (P-XMA-C11 and M-XMAs) or DDM:

(a) Results of SDS-PAGE and western blotting showing the amount and structure of MelB protein; and (b) Histogram of the total amount of proteins present in a membrane sample (Memb) that is not treated with an amphiphilic compound by percentage;

FIG. 42 shows results of measuring the amount of MelB protein extracted at four different temperatures (0, 45, 55 and 65° C.) using 1.5 wt % of XMAs (P-XMA-C11 and O-XMAs) or DDM:

(a) Results of SDS-PAGE and western blotting showing the amount and structure of MelB protein; and (b) Histogram of the total amount of proteins present in a membrane sample (Memb) that is not treated with an amphiphilic compound by percentage;

FIG. 43 shows results of measuring $\beta_2 AR$ structural stability by P-XMAs:

(a) Fluorescence spectrum of mBBr-$\beta_2 AR$ solubilized in P-XMA-C11 and DDM micelles according to the absence or presence of a full agonist (isopreoterenol, ISO), or a combination of ISO and G-protein;

(b) Fluorescence spectrum of mBBr-$\beta_2 AR$ using P-XMA-C11, P-XMA-C12 or DDM at a concentration of CMC or less; and (c) Result of measuring the ligand ([$^3$H]-DHA)-binding activity of $\beta_2 AR$ solubilized in DDM, P-XMA-C11 or P-XMA-C12;

FIG. 44 is a graph illustrating a result of measuring $\beta_2 AR$ structural stability by DDM, P-XMA-C11 or P-XMA-C12 in an unliganded form, an ISO-present state, and ISO and G-protein-present state; and FIG. 45 is a graph illustrating a result of measuring $\beta_2 AR$ structural stability by XMAs, that is, the ligand ([$^3$H]-DHA)-binding activity of $\beta_2 AR$ solubilized in DDM, P-XMA-C11, M-XMAs (a) or O-XMAs (b).

DETAILED DESCRIPTION OF EXEMPLARY EMBODIMENTS

Hereinafter, the present invention will be described in further detail with reference to examples below. However, the following examples are merely provided to illustrate the present invention, and the scope of the present invention is not limited thereto. It should be construed that the details which can be easily deduced from the detailed description and examples of the present invention by those of ordinary skill in the art belong to the scope of the present invention.

<Example 1> Methods for Synthesizing P-XMAs and P-XGAs

The synthesis schemes for P-XMAs and P-XGAs are shown in FIG. 1. Five types of para-xylene-linked maltoside amphiphiles (P-XMAs) and three types of para-xylene-linked glucoside amphiphiles (P-XGAs) were synthesized according to synthesis methods <1-1> to <1-5> below, and are shown in FIG. 2.

<1-1> Synthesis of Compound A

Diethyl malonate (5.0 equiv.) was solubilized in a solvent mixture of THF (20 mL) and DMF (20 mL) at 1:1, and $K_2CO_3$ (5.0 equiv.) was slowly added in an ice bath at 0° C. The mixture was agitated until a sufficient amount of gas was produced, 1-bromoalkane (1.0 equiv.) was added, and a reaction was performed for 6 hours at 90° C. After the reaction, the product was extracted into an organic layer using diethyl ether, a 1M HCl aqueous solution (20 mL) and brine (100 mL). The organic layer was collected, water was removed using anhydrous $Na_2SO_4$, and the solvent was evaporated using a rotary evaporator. Liquid Product A was obtained using silica gel chromatography (EtOAc/hexane).

<1-2> General Synthesis Procedure for Introduction of Xylene Linker (Step a; A→B)

Compound A (2.4 equiv.) and NaH (3.0 equiv.) were solubilized in a solvent mixture of THF (20 mL) and DMF (20 mL) at 1:1 in an ice bath at 0° C., and then α, α'-dibromo-p-xylene (1.0 equiv.) was added. The reaction was performed for 6 hours at room temperature. After the reaction, the product was extracted using an organic layer using diethyl ether (50 mL), a 1M HCl aqueous solution (20 mL) and brine (100 mL). The extracted organic layer was dehydrated using anhydrous $Na_2SO_4$, and the solvent was removed using a rotary evaporator. Liquid Product B was obtained using silica gel chromatography (EtOAc/hexane).

<1-3> General Synthesis Procedure for Reduction of Ester Using Lithium Aluminum Hydride (LAH) (Step b; B→C)

Compound B was solubilized in THF (20 mL), and $LiAlH_4$ (5.0 equiv.) was slowly added in an ice bath at 0° C. The reaction mixture was reacted at room temperature for one day. After the reaction, following slowly quenching with MeOH, the resulting product was extracted into an organic layer using diethyl ether (2×30 mL), a 1M HCl aqueous solution and brine. Water and a solvent were removed from the extracted organic layer using anhydrous $Na_2SO_4$ and a rotary evaporator, respectively. Solid Product C was obtained using silica gel chromatography (EtOAc/hexane).

<1-4> General Synthesis Procedure for Glycosylation Reaction (Step c; C→D)

This procedure was carried out by a synthesis method proposed by P. R. Ashton et al. (*Chem. Eur. J.* 1996, 2, 1115-1128.). An alcohol derivative, Compound C, and AgOTf (5.0 equiv.) and 2,4,6-collidine (2.0 equiv.) were solubilized in anhydrous $CH_2Cl_2$ (40 mL), and agitated at −45° C. Perbenzoylated maltosylbromide (5.0 equiv.) solubilized in anhydrous $CH_2Cl_2$ (40 mL) was added to the solution for 30 minutes. The reaction was performed at −45° C. for 30 minutes, and further performed for 90 minutes while a temperature was slowly increased to 0° C. After the reaction, pyridine was added to the mixture, and filtered through Celite. The filtered liquid was washed using a 1M $Na_2S_2O_3$ aqueous solution (40 mL) and an 0.1M HCl aqueous solution (40 mL) and brine (2×40 mL). The organic layer was dehydrated using anhydrous $Na_2SO_4$, and the solvent was distilled using a rotary evaporator. Solid Product D was obtained by purifying a residue using silica gel chromatography (EtOAc/hexane).

<1-5> General Synthesis Procedure for Deprotection Reaction (Step d; D→E)

This procedure was carried out by a synthesis method proposed by P. R. Ashton et al. (*Chem. Eur. J.* 1996, 2, 1115-1128.). 0-protected Compound D was solubilized in MeOH, and then added until the final concentration of a 0.5M methanolic solution (NaOMe) became 0.05M. The reaction mixture was reacted at room temperature for 6 hours, and neutralized using an Amberlite IR-120 ($H^+$ form) resin. The resin was removed from the reaction mixture using a glass filter, and a residue was purified using silica gel chromatography (MeOH/$CH_2Cl_2$). The residue was recrystallized using $CH_2Cl_2$/MeOH/diethyl ether, thereby obtaining purer white solid Product E. Product E obtained thereby is a compound of the present invention, P-XMAs.

<Example 2> Synthesis of M-XMAs and O-XMAs

The synthesis scheme of M-XMAs is shown in FIG. 3, and the synthesis scheme of O-XMAs is shown in FIG. 4. Five types of meta-xylene-linked maltoside amphiphiles (M-XMAS) and five types of ortho-xylene-linked maltoside amphiphiles (O-XMAS) were synthesized by synthesis methods <2-1> to <2-5> below, and are shown in FIG. 5.

<2-1> Synthesis of Compound A

Diethyl malonate (5.0 equiv.) was solubilized in a solvent mixture of THF (15 mL) and DMF (30 mL) at 1:2, and $K_2CO_3$ (5.0 equiv.) was slowly added in an ice bath at 0° C. The mixture was agitated until a sufficient amount of gas was produced, 1-bromoalkane (1.0 equiv.) was added, and a reaction was performed for 6 hours at 60° C. After the reaction, the product was extracted into an organic layer using diethyl ether, a 0.1M HCl aqueous solution (70 mL) and brine (100 mL). The organic layer was collected, water was removed using anhydrous $Na_2SO_4$, and the solvent was evaporated using a rotary evaporator. Oily liquid Product A was obtained using silica gel chromatography (EtOAc/hexane).

<2-2> General Synthesis Procedure for Introduction of Xylene Linker (Step a; A→B)

Compound A (2.4 equiv.) and NaH (3.0 equiv.) were solubilized in a solvent mixture of THF (10 mL) and DMF (20 mL) at 1:2 in an ice bath at 0° C., and then m-xylene dibromide or o-xylylene dibromide (1.0 equiv.) was added. The reaction was performed for 6 hours at room temperature. After the reaction, the product was extracted into an organic layer using diethyl ether (50 mL), a 0.1M HCl aqueous solution (20 mL) and brine (100 mL). The extracted organic layer was dehydrated using anhydrous $Na_2SO_4$, and the solvent was removed using a rotary evaporator. Oily liquid Product B was obtained using silica gel chromatography (EtOAc/hexane).

<2-3> General Synthesis Procedure for Reduction of Ester Using Lithium Aluminum Hydride (LAH) (Step b; B→C)

Compound B (1.0 equiv.) was solubilized in THF (30 mL), and $LiAlH_4$ (5.0 equiv.) was slowly added in an ice bath at 0° C. The reaction mixture was reacted at room temperature for one day. After the reaction, following slowly quenching with MeOH, the resulting product was extracted into an organic layer using diethyl ether (2×30 mL), a 1M HCl aqueous solution and brine. Water and a solvent were removed from the extracted organic layer using anhydrous $Na_2SO_4$ and a rotary evaporator, respectively. White solid Product C was obtained using silica gel chromatography (EtOAc/hexane).

<2-4> General Synthesis Procedure for Glycosylation Reaction (Step c; C→D)

This procedure was carried out by a synthesis method proposed by P. R. Ashton et al. (*Chem. Eur. J.* 1996, 2, 1115-1128.). An alcohol derivative, Compound C, and AgOTf (5.0 equiv.) and 2,4,6-collidine (2.0 equiv.) were solubilized in anhydrous $CH_2Cl_2$ (40 mL), and agitated at −45° C. Perbenzoylated maltosylbromide (5.0 equiv.) solubilized in anhydrous $CH_2Cl_2$ (40 mL) was added to the solution for 30 minutes. The reaction was performed at −45° C. for 30 minutes, and further performed for 90 minutes while a temperature was slowly increased to 0° C. After the reaction, pyridine was added to the mixture, and filtered through Celite. The filtered liquid was washed using a 1M $Na_2S_2O_3$ aqueous solution (40 mL) and a 0.1M HCl aqueous solution (40 mL) and brine (2×40 mL). The organic layer was dehydrated using anhydrous $Na_2SO_4$, and the solvent was distilled using a rotary evaporator. White solid Product D was obtained by purifying a residue using silica gel chromatography (EtOAc/hexane).

<2-5> General Synthesis Procedure for Deprotection Reaction (Step d; D→E)

This procedure was carried out by a synthesis method proposed by P. R. Ashton et al. (*Chem. Eur. J* 1996, 2, 1115-1128.). 0-protected Compound D was solubilized in MeOH, and then added until the final concentration of a 0.5M methanolic solution (NaOMe) became 0.05M. The reaction mixture was reacted at room temperature for 6 hours, and neutralized using an Amberlite IR-120 ($H^+$ form) resin. The resin was removed from the reaction mixture using a glass filter, and a residue was purified using silica gel chromatography (MeOH/$CH_2Cl_2$). The residue was recrystallized using $CH_2Cl_2$/MeOH/diethyl ether, thereby obtaining purer white solid Product E. Product E obtained thereby is a compound of the present invention, M-XMAs or O-XMAs.

<Preparation Example 1> Synthesis of P-XMA-C8

<1-1> Synthesis of diethyl 2-octylmalonate (1)

Diethyl 2-octylmalonate (1) was synthesized with a yield of 88% according to the general procedure for the synthesis of Compound A of Example 1-1. $^1H$ NMR (400 MHz, $CDCl_3$): δ 4.24-4.15 (m, 4H), 3.31 (t, J=7.6 Hz, 1H), 1.89-1.87 (m, 2H), 1.30-1.24 (m, 18H), 0.87 (t, J=7.2 Hz, 3H); $^{13}C$ NMR (100 MHz, $CDCl_3$): δ 169.9, 61.4, 52.3, 33.1, 29.8, 29.7, 29.4, 28.9, 27.5, 22.9, 14.3.

<1-2> Synthesis of tetraethyl 2,2'-(1,4-phenylenebis (methylene))bis(2-octylmalonate) (6)

Tetraethyl 2,2'-(1,4-phenylenebis(methylene))bis(2-octylmalonate) (6) was synthesized with a yield of 84% according to the general procedure for the introduction of a xylene linker of Example 1-2. $^1H$ NMR (400 MHz, $CDCl_3$): δ 6.95 (s, 4H), 4.22-4.09 (m, 8H), 3.17 (s, 4H), 1.75-1.73 (m, 4H), 1.26-1.20 (m, 36H), 0.88 (t, J=7.2 Hz, 6H); $^{13}C$ NMR (100 MHz, CDCl$_3$): δ 171.6, 135.1, 129.9, 61.3, 58.9, 37.8, 32.0, 31.9, 29.9, 29.5, 29.4, 24.2, 22.9, 14.3.

<1-3> Synthesis of 2,2'-(1,4-phenylenebis(methylene))bis(2-octylpropane-1,3-diol) (11)

2,2'-(1,4-phenylenebis(methylene))bis(2-octylpropane-1,3-diol) (11) was synthesized with a yield of 90% according to the general procedure for reduction of an ester using LAH of Example 1-3. $^1$H NMR (400 MHz, CD$_3$OD): δ 7.10 (s, 4H), 3.41-3.53 (m, 8H), 2.56 (s, 4H), 1.34-1.21 (m, 24H), 1.12-1.08 (m, 4H), 0.88 (t, J=7.2 Hz, 6H); $^{13}$C NMR (100 MHz, CD$_3$OD): δ 137.1, 131.3, 65.9, 44.1, 37.5, 33.3, 32.1, 31.9, 31.0, 30.9, 30.7, 24.1, 23.9, 14.7.

<1-4> Synthesis of P-XMA-C8a

P-XMA-C8a was synthesized with a yield of 80% according to the general procedure for the glycosylation of Example 1-4. $^1$H NMR (400 MHz, CDCl$_3$): δ 8.10-8.05 (m, 8H), 8.02-7.96 (m, 8H), 7.91-7.84 (m, 16H), 7.82-7.79 (m, 16H), 7.74-7.71 (m, 8H), 7.64-7.19 (m, 84H), 6.71 (s, 4H), 6.14-6.09 (m, 4H), 5.80-5.71 (m, 10H), 5.68-5.63 (m, 4H), 5.29-5.15 (m, 9H), 4.65-4.56 (m, 9H), 4.53-4.26 (m, 20H), 3.33 (d, J=7.2 Hz, 2H), 3.23 (d, J=8.8 Hz, 2H), 2.80 (d, J=8.8 Hz, 2H), 2.69 (d, J=8.8 Hz, 2H), 2.27 (d, J=13.2 Hz, 2H), 1.97 (d, J=13.2 Hz, 2H), 1.25-1.11 (m, 28H), 0.92 (t, J=6.8 Hz, 6H); $^{13}$C NMR (100 MHz, CDCl$_3$): δ 166.2, 166.1, 165.9, 165.9, 165.6, 165.2, 164.9, 164.9, 134.7, 133.9, 133.6, 133.3, 133.2, 130.1, 130.0, 129.8, 129.7, 129.6, 129.4, 129.3, 129.1, 128.9, 128.8, 128.5, 128.4, 100.8, 95.9, 74.8, 72.6, 72.3, 72.1, 71.4, 71.1, 70.5, 69.9, 69.1, 63.3, 62.6, 60.5, 41.6, 35.9, 32.1, 30.3, 30.0, 29.9, 29.8, 29.6, 22.8, 22.4, 21.2, 14.3.

<1-5> Synthesis of P-XMA-C8

P-XMA-C8 was synthesized with a yield of 95% according to the general procedure for the deprotection of Example 1-5. The $^1$H NMR spectrum is shown in FIG. 6, and the $^{13}$C NMR spectrum is shown in FIG. 7. $^1$H NMR (400 MHz, CD$_3$OD): δ 7.17 (s, 4H), 5.19-5.16 (m, 4H), 4.40-4.37 (m, 4H), 3.92-3.80 (m, 14H), 3.76-3.52 (m, 28H), 3.48-3.33 (m, 16H), 3.29-3.24 (m, 6H), 2.69 (d, J=13.2 Hz, 2H), 2.54 (d, J=13.2 Hz, 2H), 1.34-1.20 (m, 28H), 0.90 (t, J=6.8 Hz, 6H); $^{13}$C NMR (100 MHz, CD$_3$OD): δ 131.5, 103.1, 78.1, 76.7, 75.2, 74.9, 74.3, 71.7, 62.9, 33.3, 30.9, 30.7, 23.9, 14.7; HRMS (EI): calcd. for C$_{78}$H$_{134}$O$_{44}$[M+Na]$^+$ 1797.8146, found 1797.8130.

<Preparation Example 2> Synthesis of P-XMA-C9

<2-1> Synthesis of diethyl 2-nonylmalonate (2)

Diethyl 2-nonylmalonate (2) was synthesized with a yield of 89% according to the general procedure for the synthesis of Compound A of Example 1-1. $^1$H NMR (400 MHz, CDCl$_3$): δ 4.22-4.16 (m, 4H), 3.31 (t, J=7.6 Hz, 1H), 1.90-1.86 (m, 2H), 1.34-1.25 (m, 20H), 0.87 (t, J=7.2 Hz, 3H); $^{13}$C NMR (100 MHz, CDCl$_3$): δ 169.8, 61.5, 52.3, 33.1, 29.8, 29.7, 29.5, 29.4, 28.9, 27.5, 22.9, 14.3.

<2-2> Synthesis of tetraethyl 2,2'-(1,4-phenylenebis(methylene))bis(2-nonylmalonate) (7)

Tetraethyl 2,2'-(1,4-phenylenebis(methylene))bis(2-nonylmalonate) (7) was synthesized with a yield of 81% according to the general procedure for the introduction of a xylene linker of Example 1-2. $^1$H NMR (400 MHz, CDCl$_3$): δ 6.95 (s, 4H), 4.20-4.11 (m, 8H), 3.17 (s, 4H), 1.75-1.73 (m, 4H), 1.25-1.20 (m, 40H), 0.88 (t, J=7.2 Hz, 6H); $^{13}$C NMR (100 MHz, CDCl$_3$): δ 171.6, 135.1, 129.9, 61.3, 58.9, 37.8, 32.0, 31.9, 29.9, 29.5, 29.4, 24.2, 22.9, 14.3.

<2-3> Synthesis of 2,2'-(1,4-phenylenebis(methylene))bis(2-nonylpropane-1,3-diol) (12)

2,2'-(1,4-phenylenebis(methylene))bis(2-nonylpropane-1,3-diol) (12) was synthesized with a yield of 90% according to the general procedure for the reduction of an ester using LAH of Example 1-3. $^1$H NMR (400 MHz, CD$_3$OD): δ 7.10 (s, 4H), 3.41-3.53 (m, 8H), 2.56 (s, 4H), 1.34-1.21 (m, 28H), 1.12-1.08 (m, 4H), 0.88 (t, J=7.2 Hz, 6H); $^{13}$C NMR (100 MHz, CD$_3$OD): δ 137.1, 131.3, 65.9, 44.1, 37.5, 33.3, 32.1, 31.9, 31.0, 30.9, 30.7, 24.1, 23.9, 14.7.

<2-4> Synthesis of P-XMA-C9a

P-XMA-C9a was synthesized with a yield of 82% according to the general procedure for the glycosylation of Example 1-4. $^1$H NMR (400 MHz, CDCl$_3$): δ 8.10-8.05 (m, 8H), 8.02-7.96 (m, 8H), 7.91-7.84 (m, 16H), 7.82-7.79 (m, 16H), 7.74-7.71 (m, 8H), 7.64-7.19 (m, 84H), 6.76 (s, 4H), 6.20-6.15 (m, 4H), 5.84-5.76 (m, 10H), 5.72-5.68 (m, 4H), 5.35-5.20 (m, 9H), 4.67-4.62 (m, 9H), 4.58-4.36 (m, 20H), 3.38 (d, J=7.2 Hz, 2H) 3.26 (d, J=8.8 Hz, 2H), 2.89 (d, J=8.8 Hz, 2H), 2.72 (d, J=8.8 Hz, 2H), 2.30 (d, J=13.2 Hz, 2H), 2.01 (d, J=13.2 Hz, 2H), 1.32-1.24 (m, 32H), 0.92 (t, J=6.8 Hz, 6H); $^{13}$C NMR (100 MHz, CDCl$_3$): δ 166.2, 166.1, 165.9, 165.6, 165.2, 164.9, 134.7, 133.9, 133.6, 133.3, 133.2, 130.1, 129.8, 129.7, 129.6, 129.5, 129.3, 129.1, 128.9, 128.8, 128.5, 128.4, 100.8, 95.9, 74.8, 72.6, 72.3, 72.1, 71.4, 71.1, 70.5, 69.9, 69.1, 63.3, 62.6, 60.5, 41.6, 35.9, 32.1, 30.3, 30.0, 29.9, 29.8, 29.6, 22.9, 22.4, 21.2, 14.3.

<2-5> Synthesis of P-XMA-C9

P-XMA-C9 was synthesized with a yield of 94% according to the general procedure for the deprotection of Example 1-5. FIG. 8 shows the $^1$H NMR spectrum, and FIG. 9 shows the $^{13}$C NMR spectrum. $^1$H NMR (400 MHz, CD$_3$OD): δ 7.18 (s, 4H), 5.19-5.16 (m, 4H), 4.40-4.37 (m, 4H), 3.92-3.80 (m, 14H), 3.76-3.52 (m, 28H), 3.48-3.33 (m, 16H), 3.29-3.24 (m, 6H), 2.68 (d, J=13.2 Hz, 2H), 2.54 (d, J=13.2 Hz, 2H), 1.37-1.16 (m, 32H), 0.92-0.88 (t, J=6.8 Hz, 6H); $^{13}$C NMR (100 MHz, CD$_3$OD): δ 136.8, 131.5, 105.1, 103.0, 81.6, 81.5, 78.1, 76.7, 75.2, 75.0, 74.9, 74.3, 71.7, 62.9, 62.5, 43.6, 33.3, 31.9, 31.8, 31.0, 30.9, 30.7, 23.9, 14.7; HRMS (EI): calcd. for C$_{80}$H$_{138}$O$_{44}$[M+Na]$^+$ 1825.8459, found 1825.8451.

<Preparation Example 3> Synthesis of P-XMA-C10

<3-1> Synthesis of diethyl 2-decylmalonate (3)

Diethyl 2-decylmalonate (3) was synthesized with a yield of 89% according to the general procedure for the synthesis of Compound A of Example 1-1. $^1$H NMR (400 MHz, CDCl$_3$): δ 4.22-4.17 (m, 4H), 3.31 (t, J=7.6 Hz, 1H), 1.91-1.87 (m, 2H), 1.34-1.25 (m, 22H), 0.87 (t, J=7.2 Hz, 3H); $^{13}$C NMR (100 MHz, CDCl$_3$): δ 169.8, 61.5, 52.3, 32.1, 29.8, 29.7, 29.5, 29.4, 28.9, 27.5, 22.9, 14.3.

<3-2> Synthesis of tetraethyl 2,2'-(1,4-phenylenebis(methylene))bis(2-decylmalonate) (8)

Tetraethyl 2,2'-(1,4-phenylenebis(methylene))bis(2-decylmalonate)) (8) was synthesized with a yield of 82% according to the general procedure for the introduction of a xylene linker of Example 1-2. $^1$H NMR (400 MHz, CDCl$_3$): δ 6.95 (s, 4H), 4.17-4.13 (m, 8H), 3.17 (s, 4H), 1.75-1.73 (m, 4H), 1.25-1.22 (m, 44H), 0.88 (t, J=7.2 Hz, 6H); $^{13}$C NMR (100 MHz, CDCl$_3$): δ 171.6, 135.1, 129.7, 61.3, 58.8, 37.7, 32.1, 31.9, 29.9, 29.7, 29.6, 29.6, 22.2, 14.3.

<3-3> Synthesis of 2,2'-(1,4-phenylenebis(methylene))bis(2-decylpropane-1,3-diol) (13)

2,2'-(1,4-phenylenebis(methyl ene))bis(2-decylpropane-1,3-diol) (13) was synthesized with a yield of 89% according to the general procedure for reduction of an ester using LAH of Example 1-3. $^1$H NMR (400 MHz, CD$_3$OD): δ 7.10 (s, 4H), 3.41-3.35 (m, 8H), 2.56 (s, 4H), 1.34-1.21 (m, 32H), 1.12-1.08 (m, 4H), 0.88 (t, J=7.2 Hz, 6H); $^{13}$C NMR (100 MHz, CD$_3$OD): δ 137.1, 131.3, 65.9, 44.1, 37.5, 33.3, 32.1, 31.9, 31.0, 30.9, 30.7, 24.1, 23.9, 14.7.

<3-4> Synthesis of P-XMA-C10a

P-XMA-C10a was synthesized with a yield of 82% according to the general procedure for the glycosylation of Example 1-4. $^1$H NMR (400 MHz, CDCl$_3$): 8.10-8.05 (m, 8H), 8.02-7.96 (m, 8H), 7.91-7.84 (m, 16H), 7.82-7.79 (m, 16H), 7.74-7.71 (m, 8H), 7.64-7.19 (m, 84H), 6.71 (s, 4H), 6.15-6.10 (m, 4H), 5.81-5.72 (m, 10H), 5.69-5.64 (m, 4H), 5.30-5.15 (m, 9H), 4.65-4.57 (m, 9H), 4.53-4.26 (m, 20H), 3.35 (d, J=7.2 Hz, 2H), 3.22 (d, J=8.8 Hz, 2H), 2.81 (d, J=8.8 Hz, 2H), 2.69 (d, J=8.8 Hz, 2H), 2.25 (d, J=13.2 Hz, 2H), 2.04 (d, J=13.2 Hz, 2H), 1.27-1.21 (m, 36H), 0.92 (t, J=6.8 Hz, 6H); $^{13}$C NMR (100 MHz, CDCl$_3$): δ 166.2, 166.1, 165.9, 165.6, 165.2, 164.9, 134.7, 133.9, 133.6, 133.3, 133.2, 130.1, 130.0, 129.8, 129.7, 129.6, 129.5, 129.4, 129.3, 129.1, 128.9, 128.8, 128.5, 128.4, 100.8, 95.9, 95.8, 74.8, 72.6, 72.3, 72.1, 71.4, 71.1, 70.5, 69.9, 69.1, 63.3, 62.6, 60.5, 41.6, 35.9, 32.1, 30.3, 30.0, 29.9, 29.8, 29.6, 22.8, 22.4, 21.2, 14.3.

<3-5> Synthesis of P-XMA-C10

P-XMA-C10 was synthesized with a yield of 95% according to the general procedure for the deprotection of Example 1-5. FIG. 10 shows the $^1$H NMR spectrum, and FIG. 11 shows the $^{13}$C NMR spectrum. $^1$H NMR (400 MHz, CD$_3$OD): δ 7.17 (s, 4H), 5.19-5.16 (m, 4H), 4.40-4.37 (m, 4H), 3.90-3.81 (m, 14H), 3.73-3.55 (m, 28H), 3.49-3.24 (m, 16H), 3.29-3.24 (m, 6H), 2.68 (d, J=13.2 Hz, 2H), 2.54 (d, J=13.2 Hz, 2H), 1.37-1.16 (m, 28H), 0.90 (t, J=6.8 Hz, 6H); $^{13}$C NMR (100 MHz, CD$_3$OD): δ 136.8, 131.5, 105.1, 105.0, 103.0, 81.6, 81.5, 78.1, 76.6, 75.2, 75.0, 74.9, 74.3, 71.6, 62.9, 62.4, 43.6, 33.3, 31.8, 31.1, 30.9, 30.9, 30.7, 23.9, 14.7; HRMS (EI): calcd. for C$_{82}$H$_{142}$O$_{44}$[M+Na]$^+$ 1853.8772, found 1853.8759.

<Preparation Example 4> Synthesis of P-XMA-C11

<4-1> Synthesis of diethyl 2-undecylmalonate (4)

Diethyl 2-undecylmalonate (4) was synthesized with a yield of 89% according to the general procedure for the synthesis of Compound A of Example 1-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.24 (m, 24H), 0.87 (t, J=7.2 Hz, 3H); $^{13}$C NMR (100 MHz, CDCl$_3$): δ 169.8, 61.5, 52.3, 33.1, 29.8, 29.7, 29.6, 29.4, 28.9, 27.5, 22.9, 14.3.

<4-2> Synthesis of tetraethyl 2,2'-(1,4-phenylenebis(methylene))bis(2-undecylmalonate) (9)

Tetraethyl 2,2'-(1,4-phenylenebis(methylene))bis(2-undecylmalonate) (9) was synthesized with a yield of 82% according to the general procedure for the introduction of a xylene linker of Example 1-2. $^1$H NMR (400 MHz, CDCl$_3$): δ 6.96 (s, 4H), 4.21-4.0 (m, 8H), 3.18 (s, 4H), 1.76-1.74 (m, 4H), 1.27-1.20 (m, 48H), 0.88 (t, J=7.2 Hz, 6H); $^{13}$C NMR (100 MHz, CDCl$_3$): δ 171.6, 135.0, 129.9, 61.3, 58.9, 37.8, 32.1, 31.9, 29.9, 29.8, 29.6, 29.5, 22.3, 22.9, 14.3.

<4-3> Synthesis of 2,2'-(1,4-phenylenebis(methylene))bis(2-undecylpropane-1,3-diol) (14)

2,2'-(1,4-phenylenebis(methylene))bis(2-undecylpropane-1,3-diol) (14) was synthesized with a yield of 87% according to the general procedure for the reduction of an ester using LAH of Example 1-3. $^1$H NMR (400 MHz, CD$_3$OD): δ 7.10 (s, 4H), 3.41-3.35 (m, 8H), 2.56 (s, 4H), 1.34-1.21 (m, 36H), 1.21-1.08 (m, 4H), 0.88 (t, J=7.2 Hz, 6H); $^{13}$C NMR (100 MHz, CD$_3$OD): δ 137.1, 131.3, 65.9, 44.1, 37.5, 33.3, 32.1, 31.9, 31.0, 30.9, 30.9, 24.1, 23.9, 14.7.

<4-4> Synthesis of P-XMA-C11a

P-XMA-C11a was synthesized with a yield of 80% according to the general procedure for the glycosylation of Example 1-4. $^1$H NMR (400 MHz, CDCl$_3$): δ 8.10-8.05 (m, 8H), 8.02-7.96 (m, 8H), 7.91-7.84 (m, 16H), 7.82-7.79 (m, 16H), 7.74-7.71 (m, 8H), 7.64-7.19 (m, 84H), 6.71 (s, 4H), 6.15-6.10 (m, 4H), 5.81-5.72 (m, 10H), 5.69-5.64 (m, 4H), 5.30-5.15 (m, 9H), 4.65-4.57 (m, 9H), 4.53-4.26 (m, 20H), 3.35 (d, J=7.2 Hz, 2H), 3.22 (d, J=8.8 Hz, 2H), 2.81 (d, J=8.8 Hz, 2H), 2.70 (d, J=8.8 Hz, 2H), 2.26 (d, J=13.2 Hz, 2H), 2.04 (d, J=13.2 Hz, 2H), 1.27-1.21 (m, 40H), 0.93 (t, J=6.8 Hz, 6H); $^{13}$C NMR (100 MHz, CDCl$_3$): δ 166.2, 166.1, 165.9, 165.9, 165.6, 165.2, 164.9, 134.7, 133.9, 133.6, 133.3, 133.2, 130.1, 130.0, 129.8, 129.7, 129.6, 129.5, 129.4, 129.3, 129.1, 128.9, 128.8, 128.5, 128.4, 100.8, 100.7, 95.9, 95.8, 74.8, 72.6, 72.3, 72.1, 71.4, 71.1, 70.5, 69.9, 69.1, 63.3, 62.6, 60.5, 41.6, 35.9, 32.1, 30.3, 30.0, 29.9, 29.8, 29.6, 22.8, 22.4, 21.2, 14.3.

<4-5> Synthesis of P-XMA-C11

P-XMA-C11 was synthesized with a yield of 95% according to the general procedure for the deprotection of Example 1-5. FIG. 12 shows the $^1$H NMR spectrum, and FIG. 13 shows the $^{13}$C NMR spectrum. $^1$H NMR (400 MHz, CD$_3$OD): δ 7.18 (s, 4H), 5.19-5.16 (m, 4H), 4.40-4.37 (m, 4H), 3.93-3.80 (m, 14H), 3.76-3.53 (m, 28H), 3.49-3.24 (m, 16H), 3.29-3.27 (m, 6H), 2.68 (d, J=13.2 Hz, 2H), 2.54 (d, J=13.2 Hz, 2H), 1.32-1.20 (m, 40H), 0.90 (t, J=6.8 Hz, 6H); $^{13}$C NMR (100 MHz, CD$_3$OD): δ 136.8, 131.5, 105.1, 105.0, 103.1, 81.6, 78.1, 76.7, 75.2, 75.0, 74.9, 74.3, 71.7, 62.9, 62.5, 43.6, 33.3, 31.8, 31.1, 31.0, 30.9, 30.9, 30.7, 23.9, 14.7; HRMS (EI): calcd. for C$_{84}$H$_{146}$O$_{44}$[M+Na]$^+$ 1881.9085, found 1881.9091.

<Preparation Example 5> Synthesis of P-XMA-C12

<5-1> Synthesis of diethyl 2-dodecylmalonate (5)

Diethyl 2-dodecylmalonate (5) was synthesized with a yield of 89% according to the general procedure for the synthesis of Compound A of Example 1-1. $^1$H NMR (400 MHz, CDCl$_3$): δ 4.22-4.16 (m, 4H), 3.31 (t, J=7.6 Hz, 1H), 1.90-1.87 (m, 2H), 1.30-1.25 (m, 26H), 0.87 (t, J=7.2 Hz, 3H); $^{13}$C NMR (100 MHz, CDCl$_3$): δ 169.9, 61.5, 52.3, 32.1, 29.9, 29.9, 29.7, 29.6, 29.5, 29.4, 28.9, 27.5, 22.9, 14.4.

<5-2> Synthesis of tetraethyl 2,2'-(1,4-phenylenebis (methylene))bis(2-dodecylmalonate) (10)

Tetraethyl 2,2'-(1,4-phenylenebis(methylene))bis(2-dodecylmalonate) (10) was synthesized with a yield of 82% according to the general procedure for the introduction of a xylene linker of Example 1-2. $^1$H NMR (400 MHz, CDCl$_3$): δ 6.95 (s, 4H), 4.20-4.11 (m, 8H), 3.17 (s, 4H), 1.75-1.73 (m, 4H), 1.25-1.20 (m, 52H), 0.88 (t, J=7.2 Hz, 6H); $^{13}$C NMR (100 MHz, CDCl$_3$): δ 171.6, 135.1, 129.7, 61.3, 58.8, 37.7, 32.1, 31.9, 29.9, 29.7, 29.6, 29.6, 22.2, 14.3.

<5-3> Synthesis of 2,2'-(1,4-phenylenebis(methylene))bis(2-dodecylpropane-1,3-diol) (15)

2,2'-(1,4-phenylenebis(methylene))bis(2-dodecylpropane-1,3-diol) (15) was synthesized with a yield of 89% according to the general procedure for the reduction of an ester using LAH of Example 1-3. $^1$H NMR (400 MHz, CD$_3$OD): δ 7.10 (s, 4H), 3.41-3.35 (m, 8H), 2.56 (s, 4H), 1.34-1.21 (m, 40H), 1.21-1.08 (m, 4H), 0.88 (t, J=7.2 Hz, 6H); $^{13}$C NMR (100 MHz, CD$_3$OD): δ 137.1, 131.3, 65.9, 44.2, 37.5, 33.3, 32.1, 31.9, 31.0, 30.9, 30.9, 24.1, 23.9, 14.7.

<5-4> Synthesis of P-XMA-C12a

P-XMA-C12a was synthesized with a yield of 81% according to the general procedure for the glycosylation of Example 1-4. $^1$H NMR (400 MHz, CDCl$_3$): δ 8.10-8.05 (m, 8H), 8.02-7.96 (m, 8H), 7.91-7.84 (m, 16H), 7.82-7.79 (m, 16H), 7.74-7.71 (m, 8H), 7.64-7.19 (m, 84H), 6.71 (s, 4H), 6.15-6.10 (m, 4H), 5.81-5.72 (m, 10H), 5.69-5.64 (m, 4H), 5.30-5.15 (m, 9H), 4.65-4.57 (m, 9H), 4.53-4.26 (m, 20H), 3.35 (d, J=7.2 Hz, 2H), 3.22 (d, J=8.8 Hz, 2H), 2.81 (d, J=8.8 Hz, 2H), 2.69 (d, J=8.8 Hz, 2H), 2.25 (d, J=13.2 Hz, 2H), 2.04 (d, J=13.2 Hz, 2H), 1.27-1.21 (m, 44H), 0.92 (t, J=6.8 Hz, 6H); $^{13}$C NMR (100 MHz, CDCl$_3$): δ 166.2, 166.1, 165.9, 165.6, 165.2, 164.9, 134.7, 133.9, 133.6, 133.6, 133.3, 133.2, 130.1, 130.0, 129.8, 129.7, 129.6, 129.5, 129.4, 129.3, 129.1, 128.9, 128.8, 128.5, 128.4, 100.8, 95.9, 74.8, 72.6, 72.3, 72.1, 71.4, 71.1, 70.5, 69.9, 69.1, 63.3, 62.6, 60.5, 41.6, 35.9, 32.1, 30.3, 30.0, 29.9, 29.8, 29.6, 22.8, 22.4, 21.2, 14.3.

<5-5> Synthesis of P-XMA-C12

P-XMA-C12 was synthesized with a yield of 95% according to the general procedure for the deprotection of Example 1-5. FIG. 14 shows the $^1$H NMR spectrum, and FIG. 15 shows the $^{13}$C NMR spectrum. $^1$H NMR (400 MHz, CD$_3$OD): δ 7.18 (s, 4H), 4.19-51.16 (m, 4H), 4.40-4.38 (m, 4H), 3.94-3.80 (m, 14H), 3.76-3.55 (m, 28H), 3.53-3.24 (m, 16H), 3.30-3.26 (m, 6H), 2.68 (d, J=13.2 Hz, 2H), 2.54 (d, J=13.2 Hz, 2H), 1.49-1.28 (m, 44H), 0.90 (t, J=6.8 Hz, 6H); $^{13}$C NMR (100 MHz, CD$_3$OD): δ 136.8, 131.5, 105.1, 103.1, 81.6, 78.1, 76.7, 75.3, 75.0, 74.9, 74.3, 71.7, 62.9, 62.4, 43.6, 33.3, 31.8, 31.0, 30.9, 30.7, 23.9, 14.7; HRMS (EI): calcd. for C$_{86}$H$_{150}$O$_{44}$[M+Na]$^+$ 1909.9398, found 1909.9387.

<Preparation Example 6> Synthesis of P-XGA-C4

Diethyl 2-butylmalonate was synthesized according to the general procedure for the synthesis of Compound A of Example 1-1. Tetraethyl 2,2'-(1,4-phenylenebis(methylene))bis(2-butylmalonate) was synthesized according to the general procedure for the introduction of a xylene linker of Example 1-2. 2,2'-(1,4-phenylenebis(methylene))bis(2-butylpropane-1,3-diol) was synthesized according to the general procedure for the reduction of an ester using LAH of Example 1-3. P-XGA-C4a was synthesized using perbenzoylated glucosylbromide instead of perbenzoylated maltosylbromide in the general procedure for the glycosylation of Example 1-4. P-XGA-C4 was synthesized according to the general procedure for the deprotection of Example 1-5.

<Preparation Example 7> Synthesis of P-XGA-C5

Diethyl 2-pentylmalonate was synthesized according to the general procedure for the synthesis of Compound A of Example 1-1. Tetraethyl 2,2'-(1,4-phenylenebis(methylene))bis(2-pentylmalonate) was synthesized according to the general procedure for the introduction of a xylene linker of Example 1-2. 2,2'-(1,4-phenylenebis(methylene))bis(2-pentylpropane-1,3-diol) was synthesized according to the general procedure for the reduction of an ester using LAH of Example 1-3. P-XGA-C5a was synthesized using perbenzoylated glucosylbromide instead of perbenzoylated maltosylbromide in the general procedure for a glycosylation of Example 1-4. P-XGA-C5 was synthesized according to the general procedure for the deprotection of Example 1-5.

<Preparation Example 8> Synthesis of P-XGA-C6

Diethyl 2-hexylmalonate was synthesized according to the general procedure for the synthesis of Compound A of Example 1-1. Tetraethyl 2,2'-(1,4-phenylenebis(methylene))bis(2-hexylmalonate) was synthesized according to the general procedure for the introduction of a xylene linker of Example 1-2. 2,2'-(1,4-phenylenebis(methylene))bis(2-hexylpropane-1,3-diol) was synthesized according to the general procedure for the reduction of an ester using LAH of Example 1-3. P-XGA-C6a was synthesized using perbenzoylated glucosylbromide instead of perbenzoylated maltosylbromide in the general procedure for the glycosylation of Example 1-4. P-XGA-C6 was synthesized according to the general procedure for the deprotection of Example 1-5.

<Preparation Example 9> Synthesis of M-XMA-C11

<9-1> Synthesis of diethyl 2-undecylmalonate (1)

Diethyl 2-undecylmalonate (1) was synthesized with a yield of 91% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.24 (m, 24H), 0.87 (t, J=7.2 Hz, 3H); $^{13}$C NMR (100 MHz, CDCl$_3$): δ 169.8, 61.5, 52.3, 33.1, 29.8, 29.7, 29.6, 29.4, 28.9, 27.5, 22.9, 14.3.

<9-2> Synthesis of tetraethyl 2,2'-(1,3-phenylenebis(methylene))bis(2-undecylmalonate) (6')

Tetraethyl 2,2'-(1,3-phenylenebis(methylene))bis(2-undecylmalonate) (6') was synthesized with a yield of 82% by introducing an m-xylene linker according to the general procedure for the introduction of a xylene linker of Example 2-2. $^1$H NMR (400 MHz, CDCl$_3$): δ 7.12 (t, J=7.6 Hz, 1H), 6.93-6.90 (m, 2H), 6.82 (s, 1H), 4.23-4.10 (m, 8H), 3.17 (s, 4H), 1.76-1.73 (m, 4H), 1.32-1.21 (m, 48H), 0.88 (t, J=6.8 Hz, 6H); $^{13}$C NMR (100 MHz, CDCl$_3$): δ 171.6, 136.4, 131.9, 128.6, 128.2, 61.3, 58.9, 38.2, 32.1, 31.9, 29.9, 29.6, 24.4, 22.9, 14.3.

<9-3> Synthesis of 2,2'-(1,3-phenylenebis(methylene))bis(2-undecylpropane-1,3-diol) (11')

2,2'-(1,3-phenylenebis(methylene))bis(2-undecylpropane-1,3-diol) (11') was synthesized with a yield of 87% according to the general procedure for the reduction of an ester using LAH of Example 2-3. $^1$H NMR (400 MHz, CDCl$_3$): δ 7.28 (s, 1H), 7.19 (t, J=6.8 Hz, 1H), 6.99 (d, J=7.2 Hz, 2H), 3.57 (d, J=7.2 Hz, 4H), 3.45 (d, J=7.2 Hz, 4H), 2.69 (s, 4H), 1.34-1.09 (m, 40H), 0.88 (t, J=6.8 Hz, 6H); $^{13}$C NMR (100 MHz, CDCl$_3$): δ 137.9, 133.5, 128.2, 127.8, 68.4, 43.0, 36.8, 32.2, 31.5, 30.8, 29.9, 29.6, 23.2, 22.9, 14.4.

<9-4> Synthesis of M-XMA-C11a

M-XMA-C11a was synthesized with a yield of 73% according to the general procedure for the glycosylation of Example 2-4. $^1$H NMR (400 MHz, CDCl$_3$): δ 8.17 (d, J=7.2 Hz, 4H), 8.09-7.96 (m, 24H), 7.89-7.82 (m, 20H), 7.75-7.72 (m, 8H), 7.57-7.19 (m, 84H), 6.87 (t, J=7.2 Hz, 1H), 6.72-6.70 (m, 2H), 6.65 (s, 1H), 6.17-6.09 (m, 4H), 5.76-5.57 (m, 10H), 5.33-5.24 (m, 4H), 5.20-5.09 (m, 4H), 4.74-4.65 (m, 10H), 4.54-4.11 (m, 20H), 3.20 (d, J=8.8 Hz, 2H), 3.11 (d, J=8.8 Hz, 2H), 3.01 (d, J=8.8 Hz, 2H), 2.81 (d, J=8.8 Hz, 2H), 2.47 (d, J=8.8 Hz, 2H), 2.30 (d, J=8.8 Hz, 2H), 1.29-1.13 (m, 40H), 0.87 (t, J=7.2 Hz, 6H); $^{13}$C NMR (100 MHz, CDCl$_3$): δ 166.7, 166.0, 165.8, 165.5, 165.4, 165.2, 165.0, 164.9, 164.7, 135.9, 134.0, 133.6, 133.5, 133.3, 133.2, 132.9, 130.2, 130.1, 130.0, 129.9, 129.8, 129.7, 129.6, 129.5, 129.3, 129.2, 129.1, 128.9, 128.8, 128.7, 128.5, 128.4, 128.3, 127.8, 100.9, 100.6, 96.4, 95.4, 74.7, 72.3, 72.1, 71.9, 71.8, 71.4, 71.0, 70.1, 69.2, 68.9, 62.8, 62.5, 41.6, 32.1, 30.4, 30.0, 29.9, 29.8, 29.5, 22.8, 22.3, 14.3.

<9-5> Synthesis of M-XMA-C11

M-XMA-C11 was synthesized with a yield of 95% according to the general procedure for the deprotection of Example 2-5. FIG. 16 shows the $^1$H NMR spectrum, and FIG. 17 shows the $^{13}$C NMR spectrum. $^1$H NMR (400 MHz, CD$_3$OD): δ 7.18 (s, 1H), 7.12-7.10 (m, 3H), 5.21-5.17 (m, 4H), 4.42-4.37 (m, 4H), 3.92-3.82 (m, 14H), 3.75-3.51 (m, 28H), 3.48-3.32 (m, 16H), 3.31-3.25 (m, 6H), 2.72 (d, J=13.2 Hz, 2H), 2.63 (d, J=13.2 Hz, 2H), 1.34-1.23 (m, 40H), 0.90 (t, J=6.8 Hz, 6H); $^{13}$C NMR (100 MHz, CD$_3$OD): δ 138.8, 129.7, 105.1, 105.0, 103.0, 81.6, 81.5, 78.1, 76.6, 75.2, 74.9, 74.3, 72.9, 72.7, 71.6, 62.9, 62.4, 49.8, 49.6, 49.4, 48.7, 48.5, 43.7, 37.9, 33.3, 32.2, 31.9, 31.1, 30.9, 30.7, 24.1, 23.9, 14.7; HRMS (EI): calcd. for C$_{84}$H$_{146}$O$_{44}$ [M+Na]$^+$ 1881.9085, found 1881.9080.

<Preparation Example 10> Synthesis of M-XMA-C12

<10-1> Synthesis of diethyl 2-dodecylmalonate (2)

Diethyl 2-dodecylmalonate (2) was synthesized with a yield of 89% according to the general procedure for the synthesis of Compound A of Example 2-1. $^1$H NMR (400 MHz, CDCl$_3$): δ 4.22-4.16 (m, 4H), 3.31 (t, J=7.6 Hz, 1H), 1.90-1.87 (m, 2H), 1.30-1.25 (m, 26H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 22.9, 14.4.

<10-2> Synthesis of tetraethyl 2,2'-(1,3-phenylenebis(methylene))bis(2-dodecylmalonate) (7')

Tetraethyl 2,2'-(1,3-phenylenebis(methylene))bis(2-dodecylmalonate) (7') was synthesized with a yield of 80% by introducing an m-xylene linker according to the general procedure for the introduction of a xylene linker of Example 2-2. $^1$H NMR (400 MHz, CDCl$_3$): δ 7.12 (t, J=7.6 Hz, 1H), 6.92-6.90 (m, 2H), 6.81 (s, 1H), 4.21-4.12 (m, 8H), 3.16 (s, 4H), 1.75-1.57 (m, 4H), 1.30-1.21 (m, 52H), 0.88 (t, J=6.8 Hz, 6H); $^{13}$C NMR (100 MHz, CDCl$_3$): δ 171.6, 136.4, 131.9, 128.6, 128.2, 61.3, 58.9, 32.1, 29.8, 29.6, 29.5, 22.9, 14.4, 14.3.

<10-3> Synthesis of 2,2'-(1,3-phenylenebis(methylene))bis(2-dodecylpropane-1,3-diol) (12')

2,2'-(1,3-phenylenebis(methylene))bis(2-dodecylpropane-1,3-diol) (12') was synthesized with a yield of 88% according to the general procedure for the reduction of an ester using LAH of Example 2-3. $^1$H NMR (400 MHz, CDCl$_3$): δ 7.28 (s, 1H), 7.19 (t, J=6.8 Hz, 1H), 6.99 (d, J=7.2 Hz, 2H), 3.57 (d, J=7.2 Hz, 4H), 3.45 (d, J=7.2 Hz, 4H), 2.70 (s, 4H), 1.33-1.09 (m, 44H), 0.88 (t, J=6.8 Hz, 6H); $^{13}$C NMR (100 MHz, CDCl$_3$): δ 137.9, 133.5, 128.2, 127.8, 68.4, 43.0, 36.8, 32.2, 31.5, 30.8, 29.9, 29.6, 23.2, 22.9, 14.4.

<10-4> Synthesis of M-XMA-C12a

M-XMA-C12a was synthesized with a yield of 70% according to the general procedure for the glycosylation of Example 2-4. $^1$H NMR (400 MHz, CDCl$_3$): δ 8.17 (d, J=7.2 Hz, 4H), 8.09-7.96 (m, 24H), 7.89-7.82 (m, 20H), 7.75-7.72 (m, 8H), 7.57-7.19 (m, 84H), 6.88 (t, J=7.2 Hz, 1H), 6.73-6.71 (m, 2H), 6.65 (s, 1H), 6.17-6.10 (m, 4H), 5.76-5.57 (m, 10H), 5.33-5.24 (m, 4H), 5.20-5.09 (m, 4H), 4.74-4.65 (m, 10H), 4.54-4.11 (m, 20H), 3.21 (d, J=8.8 Hz, 2H), 3.11 (d, J=8.8 Hz, 2H), 3.01 (d, J=8.8 Hz, 2H), 2.81 (d, J=8.8 Hz, 2H), 2.47 (d, J=8.8 Hz, 2H), 2.30 (d, J=8.8 Hz, 2H), 1.29-1.13 (m, 40H), 0.87 (t, J=7.2 Hz, 6H); $^{13}$C NMR (100 MHz, CDCl$_3$): δ 166.7, 166.0, 165.8, 165.5, 165.4, 165.2, 165.0, 164.9, 164.7, 135.9, 134.0, 133.6, 133.5, 133.3, 133.2, 132.9, 130.2, 130.1, 130.0, 129.9, 129.8, 129.7, 129.6, 129.5, 129.3, 129.2, 129.1, 128.9, 128.8, 128.7, 128.5, 128.4, 128.3, 127.8, 100.9, 100.6, 96.4, 95.4, 74.7, 72.3, 72.1, 71.9, 71.8, 71.4, 71.0, 70.1, 69.2, 68.9, 62.8, 62.5, 41.6, 32.1, 30.4, 30.0, 29.9, 29.8, 29.5, 22.8, 22.3, 14.3.

<10-5> Synthesis of M-XMA-C12

M-XMA-C12 was synthesized with a yield of 93% according to the general procedure for the deprotection of Example 2-5. FIG. 18 shows the $^1$H NMR spectrum, and FIG. 19 shows the $^{13}$C NMR spectrum. $^1$H NMR (400 MHz, CD$_3$OD): δ 7.19 (s, 1H), 7.12-7.10 (m, 3H), 5.21-5.17 (m, 4H), 4.42-4.37 (m, 4H), 3.92-3.82 (m, 14H), 3.75-3.51 (m, 28H), 3.48-3.32 (m, 16H), 3.31-3.25 (m, 6H), 2.71 (d, J=13.2 Hz, 2H), 2.62 (d, J=13.2 Hz, 2H), 1.37-1.23 (m, 44H), 0.90 (t, J=6.8 Hz, 6H); $^{13}$C NMR (100 MHz, CD$_3$OD): δ 138.8, 129.8, 105.1, 105.0, 103.1, 81.6, 81.5, 78.1, 76.7, 75.2, 74.9, 74.3, 71.6, 62.9, 62.4, 43.7, 33.3, 31.9, 31.1, 31.0, 30.7, 23.9, 14.7; HRMS (EI): calcd. for C$_{86}$H$_{150}$O$_{44}$ [M+Na]$^+$ 1909.9398, found 1909.9402.

<Preparation Example 11> Synthesis of M-XMA-C14

<11-1> Synthesis of diethyl 2-tetradecylmalonate (3)

Diethyl 2-tetradecylmalonate (3) was synthesized with a yield of 90% according to the general procedure for the synthesis of Compound A of Example 2-1. $^1$H NMR (400 MHz, CDCl$_3$): δ 4.22-4.16 (m, 4H), 3.31 (t, J=7.6 Hz, 1H), 1.90-1.87 (m, 2H), 1.30-1.25 (m, 30H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 22.9, 14.4.

<11-2> Synthesis of tetraethyl 2,2'-(1,3-phenylenebis(methylene))bis(2-tetradecylmalonate) (8')

Tetraethyl 2,2'-(1,3-phenylenebis(methylene))bis(2-tetradecylmalonate) (8') was synthesized with a yield of 83% by introducing an m-xylene linker according to the general procedure for the introduction of a xylene linker of Example 2-2. $^1$H NMR (400 MHz, CDCl$_3$): δ 7.12 (t, J=7.6 Hz, 1H), 6.92-6.90 (m, 2H), 6.81 (s, 1H), 4.21-4.12 (m, 8H), 3.16 (s, 4H), 1.75-1.57 (m, 4H), 1.30-1.21 (m, 60H), 0.88 (t, J=6.8 Hz, 6H); $^{13}$C NMR (100 MHz, CDCl$_3$): δ 171.6, 136.4, 131.9, 128.6, 128.2, 61.3, 58.9, 32.1, 29.8, 29.6, 29.5, 22.9, 14.4, 14.3.

<11-3> Synthesis of 2,2'-(1,3-phenylenebis(methylene))bis(2-tetradecylpropane-1,3-diol) (13')

2,2'-(1,3-phenylenebis(methylene))bis(2-tetradecylpropane-1,3-diol) (13') was synthesized with a yield of 85% according to the general procedure for the reduction of an ester using LAH of Example 2-3. $^1$H NMR (400 MHz, CDCl$_3$): δ 7.28 (s, 1H), 7.19 (t, J=6.8 Hz, 1H), 6.99 (d, J=7.2 Hz, 2H), 3.57 (d, J=7.2 Hz, 4H), 3.45 (d, J=7.2 Hz, 4H), 2.70 (s, 4H), 1.33-1.09 (m, 52H), 0.88 (t, J=6.8 Hz, 6H); $^{13}$C NMR (100 MHz, CDCl$_3$): δ 137.9, 133.5, 128.2, 127.8, 68.4, 43.0, 36.8, 32.2, 31.5, 30.8, 29.9, 29.6, 23.2, 22.9, 14.4.

<11-4> Synthesis of M-XMA-C14a

M-XMA-C14a was synthesized with a yield of 68% according to the general procedure for the glycosylation of Example 2-4. $^1$H NMR (400 MHz, CDCl$_3$): δ 8.17 (d, J=7.2 Hz, 4H), 8.09-7.96 (m, 24H), 7.89-7.82 (m, 20H), 7.75-7.72 (m, 8H), 7.57-7.19 (m, 84H), 6.87 (t, J=7.2 Hz, 1H), 6.72-6.70 (m, 2H), 6.65 (s, 1H), 6.17-6.09 (m, 4H), 5.76-5.57 (m, 10H), 5.33-5.24 (m, 4H), 5.20-5.09 (m, 4H), 4.74-4.65 (m, 10H), 4.54-4.11 (m, 20H), 3.20 (d, J=8.8 Hz, 2H), 3.11 (d, J=8.8 Hz, 2H), 3.01 (d, J=8.8 Hz, 2H), 2.81 (d, J=8.8 Hz, 2H), 2.47 (d, J=8.8 Hz, 2H), 2.30 (d, J 8.8 Hz, 2H), 1.29-1.13 (m, 40H), 0.87 (t, J=7.2 Hz, 6H); $^{13}$C NMR (100 MHz, CDCl$_3$): δ 166.7, 166.0, 165.8, 165.5, 165.4, 165.2, 165.0, 164.9, 164.7, 135.9, 134.0, 133.6, 133.5, 133.3, 133.2, 132.9, 130.2, 130.1, 130.0, 129.9, 129.8, 129.7, 129.6, 129.5, 129.3, 129.2, 129.1, 128.9, 128.8, 128.7, 128.5, 128.4, 128.3, 127.8, 100.9, 100.6, 96.4, 95.4, 74.7, 72.3, 72.1, 71.9, 71.8, 71.4, 71.0, 70.1, 69.2, 68.9, 62.8, 62.5, 41.6, 32.1, 30.4, 30.0, 29.9, 29.8, 29.5, 22.8, 22.3, 14.3.

<11-5> Synthesis of M-XMA-C14

M-XMA-C14 was synthesized with a yield of 96% according to the general procedure for the deprotection of Example 2-5. FIG. 20 shows the $^1$H NMR spectrum, and FIG. 21 shows the $^{13}$C NMR spectrum. $^1$H NMR (400 MHz, CD$_3$OD): δ 7.18 (s, 1H), 7.12-7.10 (m, 3H), 5.20-5.16 (m, 4H), 4.42-4.37 (m, 4H), 3.92-3.82 (m, 14H), 3.75-3.51 (m, 28H), 3.48-3.32 (m, 16H), 3.31-3.25 (m, 6H), 2.71 (d, J=13.2 Hz, 2H), 2.61 (d, J=13.2 Hz, 2H), 1.39-1.23 (m, 52H), 0.90 (t, J=6.8 Hz, 6H); $^{13}$C NMR (100 MHz, CD$_3$OD): δ 138.8, 129.8, 105.1, 103.1, 99.2, 81.6, 81.5, 78.1, 76.7, 75.2, 74.9, 74.3, 71.6, 62.9, 62.4, 43.7, 33.3, 31.9, 31.1, 30.9, 30.7, 23.9, 14.7; HRMS (EI): calcd. for C$_{90}$H$_{158}$O$_{44}$ [M+Na]$^+$ 1967.0058, found 1967.0087.

<Preparation Example 12> Synthesis of M-XMA-C16

<12-1> Synthesis of diethyl 2-hexadecylmalonate (4)

Diethyl 2-hexadecylmalonate (4) was synthesized with a yield of 86% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.25 (m, 34H), 0.87 (t, J=7.2 Hz, 314); $^{13}$C NMR (100 MHz, CDCl$_3$): δ 169.9, 61.5, 52.3, 32.1, 29.9, 29.7, 29.6, 29.5, 29.4, 28.9, 27.5, 27.2, 22.9, 14.4.

<12-2> Synthesis of tetraethyl 2,2'-(1,3-phenylenebis(methylene))bis(2-hexadecylmalonate) (9')

Tetraethyl 2,2'-(1,3-phenylenebis(methylene))bis(2-hexadecylmalonate) (9') was synthesized with a yield of 80% by introducing an m-xylene linker according to the general procedure for the introduction of a xylene linker of Example 2-2. $^1$H NMR (400 MHz, CDCl$_3$): δ 7.12 (t, J=7.6 Hz, 1H), 6.92-6.90 (m, 2H), 6.81 (s, 1H), 4.21-4.12 (m, 8H), 3.16 (s, 4H), 1.75-1.57 (m, 4H), 1.30-1.21 (m, 68H), 0.88 (t, J=6.8 Hz, 6H); $^{13}$C NMR (100 MHz, CDCl$_3$): δ 171.6, 136.4, 131.9, 128.6, 128.2, 61.3, 58.9, 32.1, 29.8, 29.6, 29.5, 22.9, 14.4, 14.3.

<12-3> Synthesis of 2,2'-(1,3-phenylenebis(methylene))bis(2-hexadecylpropane-1,3-diol) (14')

2,2'-(1,3-phenylenebis(methylene))bis(2-hexadecylpropane-1,3-diol) (14') was synthesized with a yield of 80% according to the general procedure for the reduction of an ester using LAH of Example 2-3. $^1$H NMR (400 MHz, CDCl$_3$): δ 7.29 (s, 1H), 7.20 (t, J=6.8 Hz, 1H), 6.99 (d, J=7.2 Hz, 2H), 3.57 (d, J=7.2 Hz, 4H), 3.45 (d, J=7.2 Hz, 4H), 2.70 (s, 4H), 1.34-1.09 (m, 60H), 0.88 (t, J=6.8 Hz, 6H); $^{13}$C NMR (100 MHz, CDCl$_3$): δ 137.9, 133.5, 128.2, 127.8, 68.4, 43.0, 36.8, 32.2, 31.5, 30.8, 30.0, 29.9, 29.6, 23.2, 22.9, 14.4.

<12-4> Synthesis of M-XMA-C16a

M-XMA-C16a was synthesized with a yield of 68% according to the general procedure for the glycosylation of Example 2-4. $^1$H NMR (400 MHz, CDCl$_3$): δ 8.17 (d, J=7.2 Hz, 4H), 8.09-7.96 (m, 24H), 7.89-7.82 (m, 20H), 7.75-7.72 (m, 8H), 7.57-7.19 (m, 84H), 6.87 (t, J=7.2 Hz, 1H), 6.72-6.70 (m, 2H), 6.65 (s, 1H), 6.17-6.09 (m, 4H), 5.76-5.57 (m, 10H), 5.33-5.24 (m, 4H), 5.20-5.09 (m, 4H), 4.74-4.65 (m, 10H), 4.54-4.11 (m, 20H), 3.20 (d, J=8.8 Hz, 2H), 3.11 (d, J=8.8 Hz, 2H), 3.01 (d, J=8.8 Hz, 2H), 2.81 (d, J=8.8 Hz, 2H), 2.47 (d, J=8.8 Hz, 2H), 2.30 (d, J=8.8 Hz, 2H), 1.29-1.13 (m, 40H), 0.87 (t, J=7.2 Hz, 6H); $^{13}$C NMR (100 MHz, CDCl$_3$): δ 166.7, 166.0, 165.8, 165.5, 165.4, 165.2, 165.0, 164.9, 164.7, 135.9, 134.0, 133.6, 133.5, 133.3, 133.2, 132.9, 130.2, 130.1, 130.0, 129.9, 129.8, 129.7, 129.6, 129.5, 129.3, 129.2, 129.1, 128.9, 128.8, 128.7, 128.5, 128.4, 128.3, 127.8, 100.9, 100.6, 96.4, 95.4, 74.7, 72.3, 72.1, 71.9, 71.8, 71.4, 71.0, 70.1, 69.2, 68.9, 62.8, 62.5, 41.6, 32.1, 30.4, 30.0, 29.9, 29.8, 29.5, 22.8, 22.3, 14.3.

<12-5> Synthesis of M-XMA-C16

M-XMA-C16 was synthesized with a yield of 92% according to the general procedure for the deprotection of Example 2-5. FIG. 22 shows the $^1$H NMR spectrum, and FIG. 23 shows the $^{13}$C NMR spectrum. $^1$H NMR (400 MHz, CD$_3$OD): δ 7.18 (s, 1H), 7.15-7.09 (m, 3H), 5.20-5.16 (m, 4H), 4.41-4.37 (m, 4H), 3.92-3.82 (m, 14H), 3.75-3.51 (m, 28H), 3.48-3.32 (m, 16H), 3.31-3.25 (m, 6H), 2.72 (d, J=13.2 Hz, 2H), 2.59 (d, J=13.2 Hz, 2H), 1.39-1.23 (m, 60H), 0.90 (t, J=6.8 Hz, 6H); $^{13}$C NMR (100 MHz, CD$_3$OD): δ 138.8, 129.8, 105.0, 103.1, 81.6, 78.1, 76.7, 75.2, 74.9, 74.4, 71.6, 62.9, 62.4, 43.7, 33.3, 31.9, 31.1, 31.0, 30.9, 30.7, 23.9, 14.7; HRMS (EI): calcd. for C$_{94}$H$_{166}$O$_{44}$ [M+Na]$^+$ 2023.0684, found 2022.0645.

<Preparation Example 13> Synthesis of M-XMA-C18

<13-1> Synthesis of diethyl 2-octadecylmalonate (5)

Diethyl 2-octadecylmalonate (5) was synthesized with a yield of 88% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.25 (m, 38H), 0.87 (t, J=7.2 Hz, 3H); $^{13}$C NMR (100 MHz, CDCl$_3$): δ 169.9, 61.5, 52.3, 32.1, 29.9, 29.8, 29.7, 29.6, 29.5, 29.4, 28.9, 27.5, 27.2, 22.9, 14.4.

<13-2> Synthesis of tetraethyl 2,2'-(1,3-phenylenebis(methylene))bis(2-octadecylmalonate) (10')

Tetraethyl 2,2'-(1,3-phenylenebis(methylene))bis(2-octadecylmalonate) (10') was synthesized with a yield of 81% by introducing an m-xylene linker according to the general procedure for the introduction of a xylene linker of Example 2-2. $^1$H NMR (400 MHz, CDCl$_3$): δ 7.12 (t, J=7.6 Hz, 1H), 6.92-6.90 (m, 2H), 6.81 (s, 1H), 4.21-4.12 (m, 8H), 3.16 (s, 4H), 1.75-1.57 (m, 4H), 1.30-1.21 (m, 76H), 0.88 (t, J=6.8 Hz, 6H); $^{13}$C NMR (100 MHz, CDCl$_3$): δ 171.6, 136.4, 131.9, 128.6, 128.2, 61.3, 58.9, 32.1, 29.8, 29.6, 29.5, 23.2, 22.9, 14.4, 14.3.

<13-3> Synthesis of 2,2'-(1,3-phenylenebis(methylene))bis(2-octadecylpropane-1,3-diol) (15')

2,2'-(1,3-phenylenebis(methylene))bis(2-octadecylpropane-1,3-diol)) (15') was synthesized with a yield of 75% according to the general procedure for the reduction of an ester using LAH of Example 1-3. $^1$H NMR (400 MHz, CDCl$_3$): δ 7.29 (s, 1H), 7.20 (t, J=6.8 Hz, 1H), 6.99 (d, J=7.2 Hz, 2H), 3.57 (d, J=7.2 Hz, 4H), 3.45 (d, J=7.2 Hz, 4H), 2.70 (s, 4H), 1.34-1.09 (m, 68H), 0.88 (t, J=6.8 Hz, 6H); $^{13}$C NMR (100 MHz, CDCl$_3$): δ 137.9, 133.5, 128.2, 127.8, 68.4, 43.0, 36.8, 32.2, 31.5, 30.8, 30.0, 29.9, 29.6, 23.2, 22.9, 14.4, 14.2.

<13-4> Synthesis of M-XMA-C18a

M-XMA-C18a was synthesized with a yield of 62% according to the general procedure for the glycosylation of Example 2-4. $^1$H NMR (400 MHz, CDCl$_3$): δ 8.17 (d, J=7.2 Hz, 4H), 8.09-7.96 (m, 24H), 7.89-7.82 (m, 20H), 7.75-7.72 (m, 8H), 7.57-7.19 (m, 84H), 6.87 (t, J=7.2 Hz, 1H), 6.72-6.70 (m, 2H), 6.65 (s, 1H), 6.17-6.09 (m, 4H), 5.76-5.57 (m, 10H), 5.33-5.24 (m, 4H), 5.20-5.09 (m, 4H), 4.74-4.65 (m, 10H), 4.54-4.11 (m, 20H), 3.20 (d, J=8.8 Hz, 2H), 3.11 (d, J=8.8 Hz, 2H), 3.01 (d, J=8.8 Hz, 2H), 2.81 (d, J=8.8 Hz, 2H), 2.47 (d, J=8.8 Hz, 2H), 2.30 (d, J=8.8 Hz, 2H), 1.29-1.13 (m, 40H), 0.87 (t, J=7.2 Hz, 6H); $^{13}$C NMR (100 MHz, CDCl$_3$): δ 166.7, 166.0, 165.8, 165.5, 165.4, 165.2, 165.0, 164.9, 164.7, 135.9, 134.0, 133.6, 133.5, 133.3, 133.2, 132.9, 130.2, 130.1, 130.0, 129.9, 129.8, 129.7, 129.6, 129.5, 129.3, 129.2, 129.1, 128.9, 128.8, 128.7, 128.5, 128.4, 128.3, 127.8, 100.9, 100.6, 96.4, 95.4, 74.7, 72.3, 72.1, 71.9, 71.8, 71.4, 71.0, 70.1, 69.2, 68.9, 62.8, 62.5, 41.6, 32.1, 30.4, 30.0, 29.9, 29.8, 29.5, 22.8, 22.3, 14.3.

<13-5> Synthesis of M-XMA-C18

M-XMA-C18 was synthesized with a yield of 90% according to the general procedure for the deprotection of Example 2-5. FIG. 24 shows the $^1$H NMR spectrum, and FIG. 25 shows the $^{13}$C NMR spectrum. $^1$H NMR (400 MHz, CD$_3$OD+1% (CD$_3$)$_2$SO): δ 7.18 (s, 1H), 7.15-7.09 (m, 3H), 5.20-5.16 (m, 4H), 4.41-4.37 (m, 4H), 3.92-3.82 (m, 14H), 3.75-3.51 (m, 28H), 3.48-3.32 (m, 16H), 3.31-3.25 (m, 6H), 2.72 (d, J=13.2 Hz, 2H), 2.59 (d, J=13.2 Hz, 2H), 1.39-1.23 (m, 68H), 0.90 (t, J 6.8 Hz, 6H); $^{13}$C NMR (100 MHz, CD$_3$OD+1% (CD$_3$)$_2$SO): δ 138.8, 129.8, 105.0, 103.1, 81.6, 78.1, 76.7, 75.2, 74.9, 74.4, 71.6, 62.9, 62.4, 43.7, 33.3, 31.9, 31.1, 30.8, 31.0, 30.9, 30.7, 23.9, 14.7; HRMS (EI): calcd. for C$_{98}$H$_{174}$O$_{44}$ [M+Na]$^+$ 2079.1310, found 2079.1018.

<Preparation Example 14> Synthesis of O-XMA-C11

<14-1> Synthesis of diethyl 2-undecylmalonate (1)

Diethyl 2-undecylmalonate (1) was synthesized with a yield of 91% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.24 (m, 24H), 0.87 (t, J Hz, 3H); $^{13}$C NMR (100 MHz, CDCl$_3$): δ 169.8, 61.5, 52.3, 33.1, 29.8, 29.7, 29.6, 29.4, 28.9, 27.5, 22.9, 14.3.

<14-2> Synthesis of tetraethyl 2,2'-(1,2-phenylenebis(methylene))bis(2-undecylmalonate) (6")

Tetraethyl 2,2'-(1,2-phenylenebis(methylene))bis(2-undecylmalonate) (6") was synthesized with a yield of 80% by introducing an o-xylene linker according to the general procedure for the introduction of a xylene linker of Example 2-2. $^1$H NMR (400 MHz, CDCl$_3$): δ 7.10-7.07 (m, 2H), 7.05-7.03 (m, 2H), 4.19-4.08 (m, 8H), 3.27 (s, 4H), 1.76-1.74 (m, 4H), 1.27-1.20 (m, 48H), 0.88 (t, J=7.2 Hz, 6H); $^{13}$C NMR (100 MHz, CDCl$_3$): δ 171.7, 135.9, 126.8, 61.3, 59.2, 33.9, 32.1, 30.0, 29.9, 29.8, 29.6, 24.6, 22.9, 14.2.

<14-3> Synthesis of 2,2'-(1,2-phenylenebis(methylene))bis(2-undecylpropane-1,3-diol) (11")

2,2'-(1,2-phenylenebis(methylene))bis(2-undecylpropane-1,3-diol) (11") was synthesized with a yield of 86% according to the general procedure for the reduction of an ester using LAH of Example 2-3. $^1$H NMR (400 MHz, CDCl$_3$): δ 7.22-7.21 (m, 2H), 7.15-7.12 (m, 2H), 3.59-3.52 (m, 8H), 2.84 (s, 4H), 1.43-1.24 (m, 40H), 0.88 (t, J=7.2 Hz, 6H); $^{13}$C NMR (100 MHz, CDCl$_3$): δ 138.5, 124.7, 124.6, 66.9, 39.1, 35.9, 31.9, 31.2, 30.2, 29.6, 29.3, 22.7, 14.1.

<14-4> Synthesis of O-XMA-C11a

O-XMA-C11a was synthesized with a yield of 68% according to the general procedure for the glycosylation of Example 2-4. $^1$H NMR (400 MHz, CDCl$_3$): δ 8.02-7.96 (m, 27H), 7.93-7.91 (m, 4H), 7.89-7.86 (m, 8H), 7.83-7.77 (m, 8H), 7.76-7.74 (m, 8H), 7.67 (t, J=7.2 Hz, 2H), 7.59 (t, J=7.2 Hz, 2H), 7.54-7.24 (m, 81H), 7.13-7.11 (m, 2H), 6.54-6.52 (m, 2H), 6.18-6.11 (m, 4H), 5.75-5.63 (m, 8H), 5.37-5.30 (m, 4H), 5.26-5.20 (m, 4H), 5.17-5.13 (m, 4H), 4.66-4.15 (m, 32H), 3.39 (d, J=8.8 Hz, 2H), 3.21 (d, J=8.8 Hz, 2H), 2.87 (d, J=8.8 Hz, 2H), 2.75 (d, J=8.8 Hz, 2H), 2.24 (d, J=8.8 Hz, 2H), 2.22 (d, J=8.8 Hz, 2H), 1.27-1.07 (m, 40H), 0.88 (t, J=7.2 Hz, 6H); $^{13}$C NMR (100 MHz, CDCl$_3$): δ 166.2, 166.1, 166.0, 165.9, 165.7, 165.6, 165.3, 165.2, 164.9, 136.3, 133.9, 133.7, 133.6, 133.4, 133.3, 130.1, 129.9, 129.8, 129.6, 129.4, 129.2, 129.1, 129.0, 128.9, 128.8, 128.7, 128.6, 128.5, 128.4, 100.9, 96.1, 95.6, 74.8, 72.2, 72.0, 71.9, 71.6, 71.4, 69.9, 96.2, 69.1, 62.8, 62.7, 42.4, 32.1, 31.6, 30.8, 30.1, 30.0, 29.9, 29.7, 29.6, 23.7, 22.9, 14.3.

<14-5> Synthesis of O-XMA-C11

O-XMA-C11 was synthesized with a yield of 96% according to the general procedure for the deprotection of Example 2-5. FIG. 26 shows the $^1$H NMR spectrum, and FIG. 27 shows the $^{13}$C NMR spectrum. $^1$H NMR (400 MHz, CD$_3$OD): δ 7.26-7.24 (m, 2H), 7.09-7.07 (m, 2H), 5.19-5.16 (m, 4H), 4.40-4.37 (m, 4H), 3.92-3.80 (m, 14H), 3.73-3.52 (m, 28H), 3.47-3.36 (m, 16H), 3.33-3.24 (m, 6H), 2.99 (d, J=13.2 Hz, 2H), 2.75 (d, J=13.2 Hz, 2H), 1.33-1.21 (m, 40H), 0.90 (t, J=7.2 Hz, 6H); $^{13}$C NMR (100 MHz, CD$_3$OD): δ 139.3, 132.9, 105.0, 104.9, 103.1, 81.7, 78.1, 76.6, 75.2, 75.0, 74.9, 74.3, 73.3, 72.9, 71.6, 67.1, 62.9, 62.6, 62.5, 44.4, 33.3, 32.9, 31.9, 31.0, 30.9, 30.7, 24.4, 23.9, 15.6, 14.7; FIRMS (EI): calcd. for C$_{84}$H$_{146}$O$_{44}$ [M+Na]$^+$ 1881.9085, found 1881.9089.

<Preparation Example 15> Synthesis of O-XMA-C12

<15-1> Synthesis of diethyl 2-dodecylmalonate (2)

Diethyl 2-dodecylmalonate (2) was synthesized with a yield of 89% according to the general procedure for the synthesis of Compound A of Example 2-1. $^1$H NMR (400 MHz, CDCl$_3$): δ 4.22-4.16 (m, 4H), 3.31 (t, J=7.6 Hz, 1H), 1.90-1.87 (m, 2H), 1.30-1.25 (m, 26H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 22.9, 14.4.

<15-2> Synthesis of tetraethyl 2,2'-(1,2-phenylenebis(methylene))bis(2-dodecylmalonate) (7")

Tetraethyl 2,2'-(1,2-phenylenebis(methylene))bis(2-dodecylmalonate) (7") was synthesized with a yield of 78% by introducing an o-xylene linker according to the general procedure for the introduction of a xylene linker of Example 2-2. $^1$H NMR (400 MHz, CDCl$_3$): δ 7.10-7.07 (m, 2H), 7.05-7.03 (m, 2H), 4.19-4.09 (m, 8H), 3.26 (s, 4H), 1.76-1.74 (m, 4H), 1.27-1.20 (m, 52H), 0.88 (t, J=7.2 Hz, 6H); $^{13}$C NMR (100 MHz, CDCl$_3$): δ 171.7, 135.9, 126.8, 61.3, 59.2, 33.9, 32.1, 30.0, 29.9, 29.8, 29.6, 24.6, 22.9, 14.4, 14.2.

<15-3> Synthesis of 2,2'-(1,2-phenylenebis(methylene))bis(2-dodecylpropane-1,3-diol) (12")

2,2'-(1,2-phenylenebis(methylene))bis(2-dodecylpropane-1,3-diol) (12") was synthesized with a yield of 83% according to the general procedure for the reduction of an ester using LAH of Example 2-3. $^1$H NMR (400 MHz, CDCl$_3$): δ 7.10-7.07 (m, 2H), 7.05-7.03 (m, 2H), 4.19-4.09 (m, 8H), 3.26 (s, 4H), 1.76-1.74 (m, 4H), 1.27-1.20 (m, 52H), 0.88 (t, J=7.2 Hz, 6H); $^{13}$C NMR (100 MHz, CDCl$_3$): δ 171.7, 135.9, 126.8, 61.3, 59.2, 33.9, 32.1, 30.0, 29.9, 29.8, 29.6, 24.6, 22.9, 14.4, 14.2.

<15-4> Synthesis of O-XMA-C12a

O-XMA-C12a was synthesized with a yield of 64% according to the general procedure for the glycosylation of Example 2-4. $^1$H NMR (400 MHz, CDCl$_3$): δ 8.02-7.96 (m, 27H), 7.93-7.91 (m, 4H), 7.89-7.86 (m, 8H), 7.83-7.77 (m, 8H), 7.76-7.74 (m, 8H), 7.67 (t, J=7.2 Hz, 2H), 7.59 (t, J=7.2 Hz, 2H), 7.54-7.24 (m, 81H), 7.13-7.11 (m, 2H), 6.54-6.52 (m, 2H), 6.18-6.11 (m, 4H), 5.75-5.63 (m, 8H), 5.37-5.30 (m, 4H), 5.26-5.20 (m, 4H), 5.17-5.13 (m, 4H), 4.66-4.15 (m, 32H), 3.39 (d, J=8.8 Hz, 2H), 3.21 (d, J=8.8 Hz, 2H), 2.87 (d, J=8.8 Hz, 2H), 2.75 (d, J=8.8 Hz, 2H), 2.24 (d, J=8.8 Hz, 2H), 2.22 (d, J=8.8 Hz, 2H), 1.27-1.07 (m, 44H), 0.88 (t, J=7.2 Hz, 6H); $^{13}$C NMR (100 MHz, CDCl$_3$): δ 166.2, 166.1, 166.0, 165.9, 165.7, 165.6, 165.3, 165.2, 164.9, 136.3, 133.9, 133.7, 133.6, 133.4, 133.3, 130.1, 129.9, 129.8, 129.6, 129.4, 129.2, 129.1, 129.0, 128.9, 128.8, 128.7, 128.6, 128.5, 128.4, 100.9, 96.1, 95.6, 74.8, 72.2, 72.0, 71.9, 71.6, 71.4, 69.9, 96.2, 69.1, 62.8, 62.7, 42.4, 32.1, 31.6, 30.8, 30.1, 30.0, 29.9, 29.8, 29.6, 23.7, 22.9, 14.3.

<15-5> Synthesis of O-XMA-C12

O-XMA-C12 was synthesized with a yield of 93% according to the general procedure for the deprotection of Example 2-5. FIG. 28 shows the $^1$H NMR spectrum, and FIG. 29 shows the $^{13}$C NMR spectrum. $^1$H NMR (400 MHz, CD$_3$OD): δ 7.26-7.24 (m, 2H), 7.09-7.07 (m, 2H), 5.20-5.16 (m, 4H), 4.41-4.37 (m, 4H), 3.92-3.81 (m, 14H), 3.73-3.52 (m, 28H), 3.47-3.36 (m, 16H), 3.33-3.24 (m, 6H), 3.00 (d, J=13.2 Hz, 2H), 2.76 (d, J=13.2 Hz, 2H), 1.34-1.21 (m, 44H), 0.90 (t, J=7.2 Hz, 6H); $^{13}$C NMR (100 MHz, CD$_3$OD): δ 139.3, 132.9, 126.6, 105.0, 104.9, 103.1, 81.7, 78.1, 76.6, 75.2, 75.0, 74.9, 74.3, 73.3, 62.9, 62.5, 44.4, 33.3, 32.9, 31.9, 31.0, 30.9, 30.7, 24.4, 23.9, 14.7; HRMS (EI): calcd. for C$_{86}$H$_{150}$O$_{44}$ [M+Na]$^+$ 1909.9398, found 1909.9406.

<Preparation Example 16> Synthesis of O-XMA-C14

<16-1> Synthesis of diethyl 2-tetradecylmalonate (3)

Diethyl 2-tetradecylmalonate (3) was synthesized with a yield of 90% according to the general procedure for the synthesis of Compound A of Example 2-1. $^1$H NMR (400 MHz, CDCl$_3$): δ 4.22-4.16 (m, 4H), 3.31 (t, J=7.6 Hz, 1H), 1.90-1.87 (m, 2H), 1.30-1.25 (m, 30H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 22.9, 14.4.

<16-2> Synthesis of tetraethyl 2,2'-(1,2-phenylenebis(methylene))bis(2-tetradecylmalonate) (8")

Tetraethyl 2,2'-(1,2-phenylenebis(methylene))bis(2-tetradecylmalonate) (8") was synthesized with a yield of 79% by introducing an o-xylene linker according to the general procedure for the introduction of a xylene linker of Example 2-2. $^1$H NMR (400 MHz, CDCl$_3$): δ 7.10-7.08 (m, 2H), 7.06-7.03 (m, 2H), 4.21-4.06 (m, 8H). 3.27 (s, 4H), 1.76-1.74 (m, 4H), 1.31-1.18 (m, 60H), 0.89 (t, J=7.2 Hz, 6H); $^{13}$C NMR (100 MHz, CDCl$_3$): δ 171.7, 135.9, 126.8, 61.3, 59.2, 33.9, 32.4, 32.1, 30.0, 29.9, 29.8, 29.6, 22.9, 14.4, 14.2.

<16-3> Synthesis of 2,2'-(1,2-phenylenebis(methylene))bis(2-tetradecylpropane-1,3-diol) (13")

2,2'-(1,2-phenylenebis(methylene))bis(2-tetradecylpropane-1,3-diol) (13") was synthesized with a yield of 84% according to the general procedure for the reduction of an ester using LAH of Example 2-3. $^1$H NMR (400 MHz, CDCl$_3$): δ 7.22-7.21 (m, 2H), 7.15-7.12 (m, 2H), 3.59-3.52 (m, 8H), 2.84 (s, 4H), 1.43-1.24 (m, 52H), 0.88 (t, J=7.2 Hz, 6H); $^{13}$C NMR (100 MHz, CDCl$_3$): δ 138.5, 124.7, 124.6, 66.8, 39.1, 35.9, 31.9, 31.3, 30.2, 29.6, 29.3, 25.3, 22.7, 14.1.

<16-4> Synthesis of O-XMA-C14a

O-XMA-C14a was synthesized with a yield of 65% according to the general procedure for the glycosylation of Example 2-4. $^1$H NMR (400 MHz, CDCl$_3$): δ 8.02-7.96 (m, 27H), 7.93-7.91 (m, 4H), 7.89-7.86 (m, 8H), 7.83-7.77 (m, 8H), 7.76-7.74 (m, 8H), 7.67 (t, J=7.2 Hz, 2H), 7.59 (t, J=7.2 Hz, 2H), 7.54-7.24 (m, 81H), 7.13-7.11 (m, 2H), 6.54-6.52 (m, 2H), 6.18-6.11 (m, 4H), 5.75-5.63 (m, 8H), 5.37-5.30 (m, 4H), 5.26-5.20 (m, 4H), 5.17-5.13 (m, 4H), 4.66-4.15 (m, 32H), 3.39 (d, J=8.8 Hz, 2H), 3.21 (d, J=8.8 Hz, 2H), 2.87 (d, J=8.8 Hz, 2H), 2.75 (d, J=8.8 Hz, 2H), 2.24 (d, J=8.8 Hz, 2H), 2.22 (d, J=8.8 Hz, 2H), 1.27-1.07 (m, 52H), 0.88 (t, J=7.2 Hz, 6H); $^{13}$C NMR (100 MHz, CDCl$_3$): δ 166.2, 166.1, 166.0, 165.9, 165.7, 165.6, 165.3, 165.2, 164.9, 136.3, 133.9, 133.7, 133.6, 133.4, 133.3, 130.1, 129.9, 129.8, 129.6, 129.4, 129.2, 129.1, 129.0, 128.9, 128.8, 128.7, 128.6, 128.5, 128.4, 100.9, 96.1, 95.6, 74.8, 72.2, 72.0, 71.9, 71.6, 71.4, 69.9, 96.2, 69.1, 62.8, 62.7, 42.4, 32.1, 31.6, 30.8, 30.1, 30.0, 29.9, 29.8, 29.6, 23.7, 22.9, 14.3.

<16-5> Synthesis of O-XMA-C14

O-XMA-C14 was synthesized with a yield of 92% according to the general procedure for the deprotection of Example 2-5. FIG. 30 shows the $^1$H NMR spectrum, and FIG. 31 shows the $^{13}$C NMR spectrum. $^1$H NMR (400 MHz, CD$_3$OD): δ 7.26-7.24 (m, 2H), 7.09-7.07 (m, 2H), 5.20-5.16 (m, 4H), 4.41-4.37 (m, 4H), 3.92-3.81 (m, 14H), 3.73-3.52 (m, 28H), 3.47-3.36 (m, 16H), 3.33-3.24 (m, 6H), 3.00 (d, J=13.2 Hz, 2H), 2.76 (d, J=13.2 Hz, 2H), 1.34-1.21 (m, 52H), 0.90 (t, J=7.2 Hz, 6H); $^{13}$C NMR (100 MHz, CD$_3$OD): δ 139.4, 126.6, 105.0, 104.9, 103.1, 81.7, 78.1, 76.7, 75.2, 75.0, 74.9, 74.3, 71.6, 62.9, 62.5, 44.4, 33.3, 31.9, 31.0, 30.9, 30.7, 24.4, 23.9, 14.7; HRMS (EI): calcd. for C$_{90}$H$_{158}$O$_{44}$ [M+Na]$^+$ 1967.0058, found 1967.0082.

<Preparation Example 17> Synthesis of O-XMA-C16

<17-1> Synthesis of diethyl 2-hexadecylmalonate (4)

Diethyl 2-hexadecylmalonate (4) was synthesized with a yield of 86% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.25 (m, 34H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 27.2, 22.9, 14.4.

<17-2> Synthesis of tetraethyl 2,2'-(1,2-phenylenebis(methylene))bis(2-hexadecylmalonate) (9")

Tetraethyl 2,2'-(1,2-phenylenebis(methylene))bis(2-hexadecylmalonate) (9") was synthesized with a yield of 75% by introducing an o-xylene linker according to the general procedure for the introduction of a xylene linker of Example 2-2. $^1$H NMR (400 MHz, CDCl$_3$): δ 7.10-7.07 (m, 2H), 7.05-7.03 (m, 2H), 4.19-4.08 (m, 8H), 3.27 (s, 4H), 1.76-1.74 (m, 4H), 1.27-1.20 (m, 68H), 0.88 (t, J=7.2 Hz, 6H); $^{13}$C NMR (100 MHz, CDCl$_3$): δ 171.7, 135.9, 126.8, 61.3, 59.2, 33.9, 32.1, 30.0, 29.9, 29.8, 29.6, 24.6, 22.9, 14.4, 14.2.

<17-3> Synthesis of 2,2'-(1,2-phenylenebis(methylene))bis(2-hexadecylpropane-1,3-diol) (14")

2,2'-(1,2-phenylenebis(methylene))bis(2-hexadecylpropane-1,3-diol) (14") was synthesized with a yield of 80% according to the general procedure for the reduction of an ester using LAH of Example 2-3. $^1$H NMR (400 MHz, CDCl$_3$): δ 7.22-7.21 (m, 2H), 7.15-7.12 (m, 2H), 3.59-3.52 (m, 8H), 2.84 (s, 4H), 1.43-1.24 (m, 60H), 0.88 (t, J=7.2 Hz, 6H); $^{13}$C NMR (100 MHz, CDCl$_3$): δ 138.5, 124.7, 124.6, 66.8, 39.1, 35.8, 31.9, 31.2, 30.2, 29.6, 29.4, 25.2, 22.7, 14.1.

<17-4> Synthesis of O-XMA-C16a

O-XMA-C16a was synthesized with a yield of 61% according to the general procedure for the glycosylation of Example 2-4. $^1$H NMR (400 MHz, CDCl$_3$): δ 8.02-7.96 (m, 27H), 7.93-7.91 (m, 4H), 7.89-7.86 (m, 8H), 7.83-7.77 (m, 8H), 7.76-7.74 (m, 8H), 7.67 (t, J=7.2 Hz, 2H), 7.59 (t, J=7.2 Hz, 2H), 7.54-7.24 (m, 81H), 7.13-7.11 (m, 2H), 6.54-6.52 (m, 2H), 6.18-6.11 (m, 4H), 5.75-5.63 (m, 8H), 5.37-5.30 (m, 4H), 5.26-5.20 (m, 4H), 5.17-5.13 (m, 4H), 4.66-4.15 (m, 32H), 3.39 (d, J=8.8 Hz, 2H), 3.21 (d, J=8.8 Hz, 2H), 2.87 (d, J=8.8 Hz, 2H), 2.75 (d, J=8.8 Hz, 2H), 2.24 (d, J=8.8 Hz, 2H), 2.22 (d, J=8.8 Hz, 2H), 1.27-1.07 (m, 60H), 0.88 (t, J=7.2 Hz, 6H); $^{13}$C NMR (100 MHz, CDCl$_3$): δ 166.2, 166.1, 166.0, 165.9, 165.7, 165.6, 165.3, 165.2, 164.9, 136.3, 133.9, 133.7, 133.6, 133.4, 133.3, 130.1, 129.9, 129.8, 129.6, 129.4, 129.2, 129.1, 129.0, 128.9, 128.8, 128.7, 128.6, 128.5, 128.4, 100.9, 96.1, 95.6, 74.8, 72.2, 72.0, 71.9, 71.6, 71.4, 69.9, 96.2, 69.1, 62.8, 62.7, 42.4, 32.1, 31.6, 30.8, 30.1, 30.0, 29.9, 29.8, 29.6, 23.7, 22.9, 14.3.

<17-5> Synthesis of O-XMA-C16

O-XMA-C16 was synthesized with a yield of 94% according to the general procedure for the deprotection of Example 2-5. FIG. 32 shows the $^1$H NMR spectrum, and FIG. 33 shows the $^{13}$C NMR spectrum. $^1$H NMR (400 MHz, CD$_3$OD): δ 7.26-7.24 (m, 2H), 7.09-7.07 (m, 2H), 5.20-5.16 (m, 4H), 4.41-4.37 (m, 4H), 3.92-3.81 (m, 14H), 3.73-3.52 (m, 28H), 3.47-3.36 (m, 16H), 3.33-3.24 (m, 6H), 3.00 (d, J=13.2 Hz, 2H), 2.76 (d, J=13.2 Hz, 2H), 1.34-1.21 (m, 52H), 0.90 (t, J 7.2 Hz, 6H); $^{13}$C NMR (100 MHz, CD$_3$OD): δ 139.3, 132.9, 105.0, 104.9, 103.1, 81.7, 78.1, 76.6, 75.2, 74.9, 74.3, 71.6, 62.9, 62.6, 44.4, 34.9, 33.3, 31.9, 31.0, 30.9, 30.7, 24.4, 23.9, 14.7; HRMS (EI): calcd. for C$_{94}$H$_{166}$O$_{44}$ [M+Na]$^+$ 2023.0684, found 2022.0647.

<Preparation Example 18> Synthesis of O-XMA-C18

<18-1> Synthesis of diethyl 2-octadecylmalonate (5)

Diethyl 2-octadecylmalonate (5) was synthesized with a yield of 88% according to the general procedure for the synthesis of Compound A of Example 2-1. $^1$H NMR (400 MHz, CDCl$_3$): δ 4.23-4.16 (m, 4H), 3.31 (t, J=7.6 Hz, 1H), 1.90-1.87 (m, 2H), 1.30-1.25 (m, 38H), 0.87 (t, J=7.2 Hz, 3H); $^{13}$C NMR (100 MHz, CDCl$_3$): δ 169.9, 61.5, 52.3, 32.1, 29.9, 29.8, 29.7, 29.6, 29.5, 29.4, 28.9, 27.5, 27.2, 22.9, 14.4.

<18-2> Synthesis of tetraethyl 2,2'-(1,2-phenylenebis(methylene))bis(2-octadecylmalonate) (10")

Tetraethyl 2,2'-(1,2-phenylenebis(methylene))bis(2-octadecylmalonate) (10") was synthesized with a yield of 71% by introducing an o-xylene linker according to the general procedure for the introduction of a xylene linker of Example 2-2. $^1$H NMR (400 MHz, CDCl$_3$): δ 7.10-7.07 (m, 2H), 7.05-7.03 (m, 2H), 4.19-4.08 (m, 8H), 3.27 (s, 4H), 1.76-1.74 (m, 4H), 1.27-1.20 (m, 76H), 0.88 (t, J=7.2 Hz, 6H); $^{13}$C NMR (100 MHz, CDCl$_3$): δ 171.7, 135.9, 126.8, 61.3, 59.2, 33.9, 32.1, 30.0, 29.9, 29.8, 29.7, 29.6, 24.6, 22.9, 14.2.

<18-3> Synthesis of 2,2'-(1,2-phenylenebis(methylene))bis(2-octadecylpropane-1,3-diol) (15")

2,2'-(1,2-phenylenebis(methylene))bis(2-octadecylpropane-1,3-diol) (15") was synthesized with a yield of 77% according to the general procedure for the reduction of an ester using LAH of Example 2-3. $^1$H NMR (400 MHz, CDCl$_3$): δ 7.22-7.21 (m, 2H), 7.15-7.12 (m, 2H), 3.59-3.52 (m, 8H), 2.84 (s, 4H), 1.43-1.24 (m, 68H), 0.88 (t, J=7.2 Hz, 6H); $^{13}$C NMR (100 MHz, CDCl$_3$): δ 138.5, 124.7, 124.6, 66.8, 39.2, 35.9, 31.9, 31.2, 30.2, 29.6, 29.3, 25.2, 22.7, 14.1.

<18-4> Synthesis of O-XMA-C18a

O-XMA-C18a was synthesized with a yield of 62% according to the general procedure for the glycosylation of Example 2-4. $^1$H NMR (400 MHz, CDCl$_3$): δ 8.02-7.96 (m, 27H), 7.93-7.91 (m, 4H), 7.89-7.86 (m, 8H), 7.83-7.77 (m, 8H), 7.76-7.74 (m, 8H), 7.67 (t, J=7.2 Hz, 2H), 7.59 (t, J=7.2 Hz, 2H), 7.54-7.24 (m, 81H), 7.13-7.11 (m, 2H), 6.54-6.52 (m, 2H), 6.18-6.11 (m, 4H), 5.75-5.63 (m, 8H), 5.37-5.30 (m, 4H), 5.26-5.20 (m, 4H), 5.17-5.13 (m, 4H), 4.66-4.15 (m, 32H), 3.39 (d, J=8.8 Hz, 2H), 3.21 (d, J=8.8 Hz, 2H), 2.87 (d, J=8.8 Hz, 2H), 2.75 (d, J=8.8 Hz, 2H), 2.24 (d, J=8.8 Hz, 2H), 2.22 (d, J=8.8 Hz, 2H), 1.27-1.07 (m, 68H), 0.88 (t, J=7.2 Hz, 6H); $^{13}$C NMR (400 MHz, CDCl$_3$): δ 166.2, 166.1, 166.0, 165.9, 165.7, 165.6, 165.3, 165.2, 164.9, 136.3, 133.9, 133.7, 133.6, 133.4, 133.3, 130.1, 129.9, 129.8, 129.6, 129.4, 129.2, 129.1, 129.0, 128.9, 128.8, 128.7, 128.6, 128.5, 128.4, 100.9, 96.1, 95.6, 74.8, 72.2, 72.0, 71.9, 71.6, 71.4, 69.9, 96.2, 69.1, 62.8, 62.7, 42.4, 32.1, 31.6, 30.8, 30.1, 30.0, 29.9, 29.8, 29.6, 23.7, 22.9, 14.3.

<18-5> Synthesis of O-XMA-C18

O-XMA-C18 was synthesized with a yield of 91% according to the general procedure for the deprotection of Example 2-5. FIG. 34 shows the $^1$H NMR spectrum, and FIG. 35 shows the $^{13}$C NMR spectrum. $^1$H NMR (400 MHz, CD$_3$OD+1% (CD$_3$)$_2$SO): δ 7.27-7.25 (m, 2H), 7.09-7.07 (m, 2H), 5.19-5.16 (m, 4H), 4.40-4.37 (m, 4H), 3.91-3.81 (m, 14H), 3.72-3.51 (m, 28H), 3.46-3.34 (m, 16H), 3.30-3.23 (m, 6H), 2.98 (d, J=13.2 Hz, 2H), 2.75 (d, J=13.2 Hz, 2H), 1.34-1.23 (m, 52H), 0.90 (t, J=7.2 Hz, 6H); $^{13}$C NMR (100 MHz, CD$_3$OD): δ 139.3, 132.9, 105.0, 104.9, 103.0, 81.6, 78.1, 76.7, 75.2, 75.0, 74.9, 74.3, 73.2, 71.6, 62.8, 62.5, 44.4, 33.2, 31.9, 31.0, 30.9, 30.6, 23.9, 14.7; HRMS (EI): calcd. for C$_{98}$H$_{174}$O$_{44}$ [M+Na]$^+$ 2079.1310, found 2079.1541.

<Example 3> Characteristics of XMAs

To confirm the characteristics of P-XMAs of Preparation Examples 1 to 5 synthesized according to the synthesis method of Example 1, and M-XMAs and 0-XMAs of Preparation Examples 9 to 18 synthesized according to the synthesis method of Example 2, molecular weights (M.W.) of XMAs, a critical micellar concentration (CMC) and hydrodynamic radii (R$_h$) of the formed micelles were measured.

Specifically, the critical micellar concentration (CMC) was measured using fluorescence staining and diphenylhexatriene (DPH), and the hydrodynamic radii (R$_h$) of the micelles formed by agents were measured through a dynamic light scattering (DLS) experiment. The measured results are shown in Tables 1 and 2, compared with a conventional amphiphilic molecule (detergent), DDM.

TABLE 1

| Detergent | M.W. | CMC (μM) | CMC (wt %) | R$_h$ (nm) |
|---|---|---|---|---|
| P-XMA-C8 | 1775.9 | ~20 | ~0.004 | 2.7 ± 0.04 |
| P-XMA-C9 | 1803.9 | ~10 | ~0.002 | 3.2 ± 0.01 |
| P-XMA-C10 | 1832.0 | ~7 | ~0.001 | 3.5 ± 0.01 |
| P-XMA-C11 | 1860.0 | ~3 | ~0.0006 | 3.3 ± 0.03 |
| P-XMA-C12 | 1888.1 | ~1 | ~0.0002 | 3.7 ± 0.01 |
| DDM | 510.1 | ~170 | ~0.0087 | 3.4 ± 0.02 |

TABLE 2

| Detergent | M.W. | CMC (μM) | CMC (wt %) | R$_h$ (nm) |
|---|---|---|---|---|
| P-XMA-C11 | 1860.0 | ~3.0 | ~0.0006 | 3.3 ± 0.03 |
| M-XMA-C11 | 1860.0 | ~6.0 | ~0.0011 | 3.2 ± 0.01 |
| O-XMA-C11 | 1860.0 | ~10 | ~0.0019 | 3.0 ± 0.02 |
| M-XMA-C12 | 1888.1 | ~4.0 | ~0.0008 | 3.4 ± 0.02 |
| O-XMA-C12 | 1888.1 | ~6.0 | ~0.0011 | 3.2 ± 0.03 |
| M-XMA-C14 | 1994.2 | ~2.5 | ~0.0005 | 3.6 ± 0.07 |

TABLE 2-continued

| Detergent | M.W. | CMC (μM) | CMC (wt %) | $R_h$ (nm) |
|---|---|---|---|---|
| O-XMA-C14 | 1994.2 | ~3.0 | ~0.0006 | 3.5 ± 0.04 |
| M-XMA-C16 | 2000.3 | ~2.0 | ~0.0004 | 3.9 ± 0.04 |
| O-XMA-C16 | 2000.3 | ~2.0 | ~0.0004 | 3.9 ± 0.06 |
| M-XMA-C18 | 2056.4 | ~1.5 | ~0.0003 | 4.1 ± 0.04 |
| O-XMA-C18 | 2056.4 | ~1.5 | ~0.0003 | 3.9 ± 0.04 |
| DDM | 510.1 | ~170 | ~0.0087 | 3.4 ± 0.02 |

The CMC values of XMAs were 1 to 20 μM, which were smaller than that of DDM (170 μM). In addition, as the alkyl chain length of a compound was increased, the CMC value became smaller. Among P-XMAs, P-XMA-C8, which has the shortest alkyl chain, had a CMC value of approximately 20 μM (~0.004 wt %), and P-XMA-C12, which has the longest alkyl chain, had a CMC value of 1 μM (~0.0002 wt %). The CMC values of M-XMAs and O-XMAs tended to be reduced as the alkyl chain lengths thereof were increased. Specifically, O-XMA-C11 having the shortest alkyl chain had the highest CMC value of approximately 10 μM, and O-XMA-C18 having the longest alkyl chain had the smallest CMC value of approximately 1.5 μM. In comparison between isomers, the CMC values of O-XMAs were a little higher than those of M-XMAs. Therefore, micelles were easily formed even with a small amount of XMAs, confirming that XMAs have higher solubility than DDM.

Sizes of the micelles formed by P-XMAs tended to increase according to the length of an alkyl chain. That is, the smallest micelle was P-XMA-C8 (2.7 nm), and the largest micelle was P-XMA-C12 (3.7 nm). In terms of the micelle size, P-XMA-C8 and P-XMA-C9 were smaller than DDM, and P-XMA-C10 and P-XMA-C11 were similar to DDM. In addition, M-/O-XMAs having a longer alkyl chain formed larger micelles, which corresponded to the experimental result for P-XMAs according to the change in alkyl chain length. In comparison between isomers, M-XMAs tended to form larger micelles than O-XMAs.

Therefore, M-XMAs had smaller CMC values and formed larger micelles than O-XMAs. P-XMAs tended to have smaller CMC values, and form larger micelles. It was considered that differences in CMC value (that is, agglomerating tendency) and micelle size between the isomeric XMAs were associated with the difference in efficiency of an amphiphilic compound with respect to a target membrane protein. Compared to DDM, all XMAs had smaller CMC values than DDM, and the micelle sizes of XMAs were larger or smaller than that of DDM according to the alkyl chain length.

Meanwhile, the results of measuring the size distribution of XMA micelles are shown in FIGS. 36 and 37. P-XMA-C8 and P-XMA-C9 showed one set of micelles like DDM, and P-XMA-C10, P-XMA-C11 and P-XMA-C12 had two sets of micelles having different radii (FIG. 36). The number (%) of the two sets of micelles was estimated to be 10⁶ or more, which is based on the fact that dynamic light scattering is proportional to the sixth power of the micelle radius. Therefore, a set of micelles having a smaller radius is an exclusive entity present in an amphiphilic solution containing P-XMA-C10, P-XMA-C11 or P-XMA-C12. In addition, M-XMAs and O-XMAs showed a single set of micelles in terms of a size, indicating high micelle uniformity (FIG. 37).

From such a result, since XMAs of the present invention had smaller CMC values than DDM and thus easily form micelles even with a small amount, it can be confirmed that they had a much higher self-assembly tendency than DDM, similar sizes of micelles formed by XMAs to DDM, and were similar to the conventional DDM in terms of a geometrical structure of a molecule.

<Example 4> Evaluation of Ability to Stabilize Structure of Membrane Protein (Bor1) of Compound According to the Present Invention An experiment for measuring the structural stability of a boron transporter (Bor1) in an aqueous solution due to P-XMAs was performed. The Bor1 structural stability was measured using a CPM assay, and concentrations of P-XMAs and DDM were estimated by measuring relative amounts of folded proteins at CMC+0.04 wt % (a) and CMC+0.2 wt % (b) to analyze Bor1 protein stability according to the concentration of an amphiphilic molecule.

Specifically, Bor1 was expressed as a fusion protein with a C-terminal GFP-His tag in *S. cerevisiae*. All steps were carried out at 4° C. A Bor1-containing membrane was resuspended with PBS (pH 7.4), 100 mM NaCl, and 10% glycerol and solubilized in 1% DDM for 1 hour with gentle stirring, followed by ultracentrifugation at 200,000 g for 45 minutes. The supernatant was adjusted with 10 mM imidazole, and applied to two 5 ml $Ni^{2+}$-NTA columns pre-equilibrated with Buffer A (PBS (pH 7.4), 100 mM NaCl, 10% glycerol, 0.03% DDM) supplemented with 10 mM imidazole. The column was washed with 5 CV of Buffer A supplemented with 30 mM imidazole, and washed with 5 CV of Buffer A supplemented with 50 mM imidazole, followed by elution in Buffer A supplemented with 500 mM imidazole. Fractions containing Bor1-GFP were diluted (1:10) in Buffer B (20 mM Tris (pH 7.5), 150 mM NaCl, 0.03% DDM) supplemented with 10% glycerol, and incubated overnight with an equi-molar concentration of His-tagged TEV protease to cleave the GFP-His tag. The sample was applied to a 5 ml $Ni^{2+}$-NTA column pre-equilibrated with Buffer B supplemented with 20 mM imidazole to separate Bor1 from the GFP-His tag and TEV. The flow-through containing Bor1 was concentrated to 0.5 ml using a centrifugal concentrator. The protein was subjected to gel filtration purification using a Superdex 200 10/300 column pre-equilibrated with Buffer B. Bor1 was concentrated to 7 mg/ml using a centrifugal concentrator. 4 mg/ml of N-[4-(7-diethylamino)-4-methyl-3-coumarinyl]phenyl)maleimide (CPM dye; Invitrogen) stored in DMSO (Sigma) was diluted in an assay buffer (20 mM Tris (pH 7.5), 150 mM NaCl) supplemented with 0.03% DDM. 150 μl of an assay buffer supplemented with CMC+0.04 wt % or CMC+0.20 wt % of P-XMAs or DDM was loaded into a Nunc 96-well clear bottom plate. 1 μl of Bor1 (7 mg/ml) was added to each well before adding 3 μl of a diluted CPM dye. A clear plate cover was added, and the fluorescence of each well was monitored at 40° C. for 120 minutes.

As shown in FIG. 38, Bor1 solubilized in DDM after two hours of the incubation at 40° C. showed the most instable state, but an amount of structure-denatured protein was relatively small in each P-XMA solution and exhibited a Bor1 protein stabilization effect. In addition, at concentrations of CMC+0.04 wt % and CMC+0.2 wt %, all P-XMAs had higher Bor1 stabilization ability than DDM, and all P-XMAs stabilized the protein at similar levels.

From such a result, it can be seen that P-XMAs had a higher ability to stabilize the Bor1 structure than conventional DDM.

<Example 5> Evaluation of Ability to Stabilize Membrane Protein (LeuT) Structure of Compound According to the Present Invention An experiment for measuring the structural stability of a LeuT protein due to M-XMAs or O-XMAs was performed. Each amphiphilic compound was used at CMC+0.04 wt % (a) or CMC+0.2 wt % (b), and the ligand-binding activity of LeuT was determined using [$^3$H]-Leu by scintillation proximity assay (SPA). Measurement was regularly performed at room temperature during a 12-day incubation period.

Specifically, wild-type leucine transporter (LeuT) derived from thermophilic bacteria *Aquifex aeolicus* was purified according to a previously disclosed protocol (G. Deckert et al., Nature 1998, 392, 353-358). In summary, LeuT was expressed in *E. coli* C41 (DE3) incubated in lysogeny broth supplemented with 0.1 mg/ml ampicillin. Protein expression was induced by adding isopropyl β-D-thiogalactopyranoside at the final concentration of 0.1 mM. Cell membranes were isolated from disrupted cells (Constant Systems Homogenizers, Kennesaw, Ga.), and solubilized in 1% (w/v) n-dodecyl-β-D-maltopyranoside (DDM; Affymetrix, Santa Clara, Calif.). After solubilization, LeuT was fixed to a chelating Sepharose Fast Flow resin (GE Healthcare), and approximately 90 to 100% pure LeuT was eluted in 20 mM Tris-HCl (pH 7.5), 199 mM KCl, 1 mM NaCl, 0.05% (w/v) DDM and 300 mM imidazole. Afterward, the purified LeuT (approximately 1.2 mg mL$^{-1}$) was diluted 10 times with buffer which is the same as that used above and supplemented with M-XMAs and O-XMA, except DDM and imidazole, at the final concentration of CMC+0.04% (w/v) or CMC+0.2% (w/v). DDM and P-XMA-C11 were used as positive controls. Protein samples were stored at room temperature, and protein activity at a predetermined time was determined by measuring [$^3$H]-Leucine binding using SPA. SPA was performed using a total volume of 100 µL of 54 of each protein sample solubilized in a buffer containing 450 mM NaCl, 50 nM [$^3$H]-Leucine and 0.125 mg ml$^{-1}$ copper chelate (His-Tag) YSi beads (Perkin Elmer, Denmark). A [$^3$H]-Leucine binding degree was measured using a MicroBeta liquid scintillation counter (Perkin Elmer).

As a result, M-XMA-C12 and O-XMA-C12 showed substantial reinforcement of long-term stability of LeuT, compared with DDM. M-XMA-C12 showed higher stability than O-XMA-C12. However, as the alkyl chain lengths of XMAs were further increased from C12 to C18, the ligand binding activity of LeuT was reduced, and therefore it can be seen that, when the XMA has a C12 alkyl chain length, it was most preferable for the LeuT protein. Even when a concentration of the amphiphilic compound was increased to CMC+0.2 wt %, a similar tendency was observed. XMAs (M-XMA-C12 and O-XMA-C12) with the C12 alkyl chain were superior at maintaining the ligand binding activity of LeuT compared to DDM, and M-XMA-C12 had generally better performance than O-XMA-C12 (FIG. 39).

As a result, it can be confirmed that M-XMA-C12 and O-XMA-C12 exhibited improved efficiency in maintaining the ligand binding affinity of LeuT, compared to DDM, and thus were excellent in stabilization of the LeuT protein.

<Example 6> Evaluation of Ability to Stabilize Structure of Membrane Protein (MelB) of Compound According to the Present Invention An experiment for measuring the structural stability of the *Salmonella typhimurium* melibiose permease (MelB) protein due to XMAs was performed. The MelB protein was extracted on a membrane using XMAs and DDM, and the amount and structure of the extracted protein were analyzed by SDS-PAGE and western blotting. A concentration of the used compound was 1.5 wt %, and the protein was extracted at a different temperature (0, 45, 55, or 65° C.) to evaluate two kinds of performance such as protein extraction efficiency and stabilization ability of the compound at the same time. Membrane samples that were not treated with XMAs or DDM were used as controls.

Specifically, MelB$_{St}$ stability due to DDM and XMAs was evaluated according to the method described in the paper (P. S. Chae, et al., Nat. Methods 2010, 7, 1003-1008) written by the inventor in 2010. The protein (MelB$_{St}$) was produced using plasmid pK95ΔAHB/WT MelB$_{St}$/CH10 encoding wild-type MelB with a 10-His tag at the C-terminus and *Salmonella typhimurium* DW2 cells (ΔmelB and ΔlacZY). Cell growth and membrane preparation were carried out according to the method described in the paper (Nat. Commun. 2014, 5, 3009) written by A. S. Ethayathulla et al. A protein assay was performed using a Micro BCA kit (Thermo Scientific, Rockford, Ill.). To measure solubilization/stability, MelB$_{St}$-containing membrane samples (final protein concentration of 10 mg/mL) were incubated with a solubilization buffer (20 mM sodium phosphate, pH 7.5, 200 mM NaCl, 10% glycerol, 20 mM melibiose) and 1.5% (w/v) DDM, P-XMAs (P-XMA-C8, P-XMA-C9, P-XMA-C10, P-XMA-C11 and P-XMA-C12), M-XMAs (M-XMA-C11, M-XMA-C12, M-XMA-C14, M-XMA-C16 and M-XMA-C18) or O-XMAs (O-XMA-C11, O-XMA-C12, O-XMA-C14, O-XMA-C16 and O-XMA-C18) at four different temperatures (0, 45, 55 and 65° C.) for 90 minutes. Following ultracentrifugation at 355,590 g in a Beckman Optima™ MAX ultracentrifuge using a TLA-100 rotor for 45 minutes at 4° C., 20 µg proteins were separated by SDS-16% PAGE, and then immunoblotted with a Penta-His-HRP antibody (Qiagen, Germantown, Md.). MelB$_{St}$ was detected using a SuperSignal West Pico chemiluminescent substrate by an ImageQuant LAS 4000 Biomolecular Imager (GE Health Care Life Sciences).

As shown in FIG. 40, DDM showed high protein extraction efficiency at 0 and 45° C., but proteins solubilized at 55° C. or more were hardly observed. This means that, as a temperature of MelB$_{St}$ extracted by DDM was increased, the protein was denatured or agglomerated and thus disappeared. However, P-XMA-C9, P-XMA-C10 and P-XMA-C12 had increased protein extraction efficiency at 45° C. and 55° C., exhibited extraction efficiency at the same level as DDM at 45° C., and had a higher MelB$_{St}$ extraction ability than DDM at 55° C. In addition, at 65° C., while DDM did not extract the protein, P-XMA-C10 and P-XMA-C12 extracted MelB$_{St}$. Such a result shows that P-XMA-C9, P-XMA-C10 and P-XMA-C12 exhibited a higher MelB$_{St}$ stabilization ability than DDM.

In addition, as shown in FIG. 41 and FIG. 42, at 0° C., M-XMAs (e.g., M-XMA-C16 and M-XMA-C18) having a longer alkyl chain showed protein extraction efficiency at almost the same level as DDM. However, M-XMAs and O-XMAs showed protein extraction efficiency at a higher or similar level compared to P-XMA-C11. M-XMAs and O-XMAs exhibited different tendencies with respect to the alkyl chain length of a hydrophobic group of the amphiphilic compound. MelB solubilization efficiency tended to increase according to an increase in the alkyl chain length of M-XMAs, but tended to decrease according to an increase in the alkyl chain length of O-XMAs. When the temperature was increased to 45° C., overall tendencies were similar to those at 0° C. In addition, a solubilization yield tended to increase according to an increase in the alkyl chain length of M-XMAs, but tended to decrease according to an increase in the alkyl chain length of O-XMAs. When the temperature was increased to 55° C., DDM was failed to maintain the solubilization of MelB, and this is because the proteins solubilized with DDM at a high temperature were agglomerated or denatured. However, except M-XMA-C18 and O-XMA-C18, all M-XMAs and O-XMAs had the ability to maintain MelB solubilization. Among M-XMAs, M-XMA-C14 was most effective, and retained approximately 70%-solubilized MelB. Since the ability of M-XMA-C14 to ensure MelB solubility was not greatly changed according to a temperature change, the compound can be seen to be effective in the solubilization and stabilization of a membrane protein.

From such a result, it can be confirmed that XMAs of the present invention had a higher MelB protein stabilization ability than DDM, and MelB protein extraction efficiency, which is the same at 45° C. and higher at 55° C. compared to DDM. Particularly, in terms of stabilization of the MelB protein, it can be seen that M-XMA-C12 and O-XMA-C11~C14 had the optimum alkyl chain lengths.

<Example 6> Evaluation of Ability to Stabilize Structure of Membrane Protein (β$_2$AR) of Compound According to the Present Invention An experiment for measuring the structural stability of a human β$_2$ adrenergic receptor (β$_2$AR) and a G protein-coupled receptor (GPCR) due to XMAs was carried out.

<6-1> Measurement of mBBr-β$_2$AR Solubilized in Micelles Formed by XMAs and DDM According to Absence or Presence of Full Agonist (ISO) and Combination of G-Protein An experiment for measuring the structural change and stability of mBBr-β$_2$AR due to P-XMA-C11 and DDM according to the absence or presence of a full agonist (ISO) and a combination of ISO and a G-protein was carried out.

Specifically, β$_2$AR solubilized in 0.1% DDM was purified according to the method described in the paper (*Science* 2007, 318, 1266-1273) written by D. M. Rosenbaum et al., and concentrated to approximately 1 mg/ml. 0.5 μl of unliganded and BI (agonist)-binding monobromobimane (mBB)-labeled β$_2$AR, which was solubilized in 0.1% DDM at 50 μM, was diluted with 500 μl of a 0.04+CMC % P-XMA-C11 or P-XMA-C12 buffer (finally, 50 nM receptor). The receptor was incubated for 30 minutes, and the mBBr spectrum was measured, compared to the spectrum of mBB-labeled receptor in 0.1% DDM. mBBr-β$_2$AR fluorescence was measured at 370 nm, and emission from 430 to 510 nm was measured using a Spex FluoroMax-3 spectrofluorometer (Jobin Yvon Inc.) at 1-nm units with 1 nm s$^{-1}$, and the photon counting mode was set at 4-nm emission bandwidth pass. The mBBR solubilized in DDM was used as a positive control.

Meanwhile, a G protein coupling assay was carried out by the following method. Monobromobimane (mBBr)-labeled β$_2$AR (mainly at Cys265) was used to measure changes in fluorescence affected by local conformational changes near transmembrane helix 6 (TM6). Such measurement was performed by the method suggested by S. E. Mansoor et al. (*Biochemistry* 2002, 41, 2475-2484.). 0.5 μl of 50 μM unliganded mBBr-labeled receptor was diluted with 500 μl of a 20×CMC P-XMA-C11 or P-XMA-C12 buffer (finally 50 nM receptor) for 10 minutes at RT. In addition, 2 μM isopreoterenol (ISO) was added, and the resulting product was incubated for another 10 minutes. After 250 nM Gs was further added, the resulting product was incubated at RT for 15 minutes, and mBB-β$_2$AR fluorescence was measured.

As shown in FIG. 43a, when the full agonist ISO was present, the bimane spectrum of the receptor in P-XMA-C11 or P-XMA-C12 was similar to that of the receptor in DDM. In addition, the bimane spectrum of the receptor/G-protein complex solubilized in P-XMA-C11 was similar to that of the complex solubilized in DDM. In addition, the receptor solubilized in P-XMA-C12 also showed a similar tendency thereto (FIG. 44).

Such a result shows that P-XMA-C11 and P-XMA-C12 function well in receptor activation by G-protein coupling. Such a decrease in fluorescence intensity and change in maximum emission wavelength mean conformational changes from inactive to active states, generated by the binding of ISO and a G-protein, indicating that the structure of β$_2$AR solubilized in P-XMA-C11 or P-XMA-C12 behaves in a manner similar to receptors present in the cell membrane.

<6-2> Measurement of mBBr-β$_2$AR at CMC or Less

An experiment for comparing changes in protein structures of XMAs and DDM at CMC or less of an amphiphilic molecule was carried out.

Specifically, 0.5 μl of an unliganded mBB-labeled receptor solubilized in 20×CMC P-XMA-C11 or P-XMA-C12 at 50 μM was diluted with 500 μl of a NH buffer (20 mM HEPES pH 7.5, 100 mM NaCl). The protein was incubated for 30 minutes, and the mBBr spectrum was measured. The receptor solubilized in 0.1% DDM was diluted with a NH buffer, and used as a control.

As shown in FIG. 43b, β$_2$AR solubilized in DDM showed a clear structural change due to dilution, but the receptor solubilized in P-XMA-C11 or P-XMA-C12 showed less structural change.

From such a result, it can be confirmed that P-XMA-C11 or P-XMA-C12 has excellent structural stability of the β$_2$AR protein at CMC or less, compared to DDM, which means that a rate of separating the amphiphilic molecules from receptors under a condition of CMC or less is low.

<6-3> Measurement of Ligand (DHA) Binding Activity of mBBr-β₂AR Using Radioligand Binding Assay An activation degree of a receptor (mBBr-β₂AR) purified by DDM or XMAs was measured by [³H]-dihydroalprenolol ([³H]-DHA) binding.

Specifically, a radioligand binding assay was performed by the following method. β₂AR was purified in the presence of 0.1% DDM. After β₂AR was reloaded into an M1 Flag column in the presence of 2 mM CaCl₂, a DDM (0.1%)-XMA (0.2%) buffer mixture was prepared in a ratio of 50:50, 20:80, 10:90, 5:95 or 0:100. The receptor was eluted in 20×CMC XMA with 5 mM EDTA and 0.2 mg/ml of a free Flag peptide. 0.1 pmol purified β₂AR solubilized in DDM, P-XMA-C11, P-XMA-C12, M-XMAs or O-XMAs was incubated with 10 nM of radioactive DHA [³H]-dihydroalprenolol (DHA) for 30 minutes at room temperature. The mixture was loaded into a G-50 column, and a flow-through was collected with a binding buffer (20 mM HEPES pH 7.5, supplemented with 0.5 mg/ml BSA, 100 mM NaCl), and further filled with 15 ml of a scintillation fluid. Receptor-binding [³H]DHA was measured with a scintillation counter (Beckman). Non-specific binding of [³H]-DHA was calculated by adding 1 μM of alprenolol (Sigma) in the same binding reaction. The binding degree of [³H]-DHA was measured as a column graph.

As shown in FIG. 43c, the receptor purified by P-XMA-C11 or P-XMA-C12 had a radioactive-ligand binding degree similar to the receptor purified by DDM. This means that the activity of the receptor is well maintained while amphiphilic molecules of XMAs are replaced with DDM molecules surrounding the receptor.

In addition, as shown in FIG. 45, M-XMA-C11 had a higher radioactive-ligand binding degree than P-XMA-C11. When the alkyl chain length of the amphiphilic molecule was increased from C11 to C12, the effect of the amphiphilic molecule was further increased. In maintaining the ligand binding activity of the receptor, M-XMA-C12 was superior to O-XMA-C12, and similar to DDM. As the alkyl chain length of M-XMAs was increased to C18, the effect of the amphiphilic compound was reduced. That is, in M-XMAs, it can be seen that the C12 alkyl chain length was optimal for maintaining the activity of the receptor, which corresponded to the result for LeuT. O-XMAs had a difference from M-XMAs, and less change in the effect of maintaining the activity of the receptor according to the change in alkyl chain length. It is expected that different tendencies in the effects of M-XMAs and O-XMAs according to the alkyl chain length are caused by different effects on binding to a target membrane protein due to different geometrical structures.

From such a result, it was seen that P-XMA-C11, P-XMA-C12, M-XMA-C11, M-XMA-C12 and O-XMAs can be used as alternatives for DDM, which is most widely used in β₂AR studies.

By using xylene-based compounds according to exemplary embodiments of the present invention, compared to a conventional compound, a membrane protein can be stably stored in an aqueous solution for a long time, and can be subjected to functional analysis and structural analysis.

Since the structural and functional analysis of a membrane protein is one of the fields of highest interest in biology and chemistry, the compounds according to exemplary embodiments of the present invention can be applied in research on protein structure that is closely related to development of a new drug.

Specifically, the compounds according to exemplary embodiments of the present invention can form a high quality membrane protein crystal due to a small size when a complex with the membrane protein is formed, and have a xylene linker which is structurally rigid and two quaternary carbon atoms introduced at a xylene terminal, thereby greatly limiting the flowability of the total molecule, and therefore the crystallization of the membrane protein can be promoted.

In addition, since the compounds of the present invention can be synthesized from a starting material that can be easily obtained by a simple method, the compounds can be mass-produced for research on a membrane protein.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:
1. A compound represented by Formula 1 below:

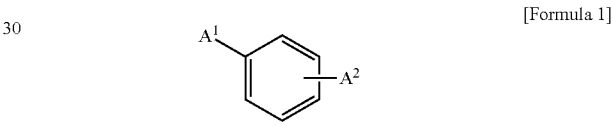

[Formula 1]

where the position of A², relative to A¹, is ortho, meta or para;
A¹ and A² are the same or different and each independently represented by Formula 2 below;

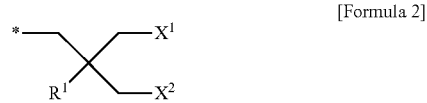

[Formula 2]

R¹ is a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;
X¹ and X² are each independently a saccharide linked by an oxygen atom; and
the symbol * in Formula 2 may represent a part linked to the core structure of Formula 1.

2. The compound of claim 1, wherein the saccharide is a monosaccharide or a disaccharide.

3. The compound of claim 1, wherein the saccharide is glucose or maltose.

4. The compound of claim 1, wherein A¹ and A² are the same as each other; R¹ is a substituted or unsubstituted $C_3$-$C_{26}$ alkyl group; and X¹ and X² are oxygen-linked maltoses.

5. The compound of claim 1, wherein A¹ and A² are the same as each other; R¹ is a substituted or unsubstituted $C_3$-$C_{26}$ alkyl group; and X¹ and X² are oxygen-linked glucoses.

6. The compound of claim 1, wherein the compound is one of Formulas 3 to 20 below:

[Formula 3]
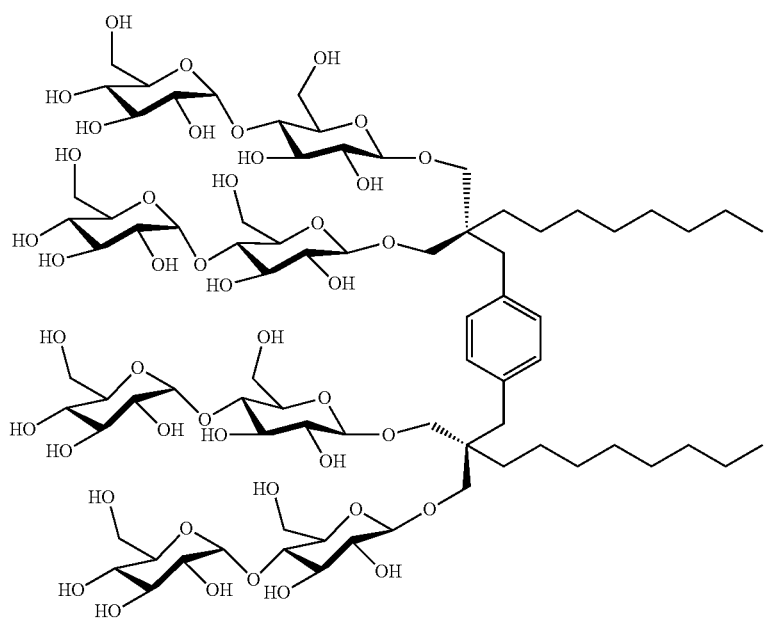
[Formula 4]
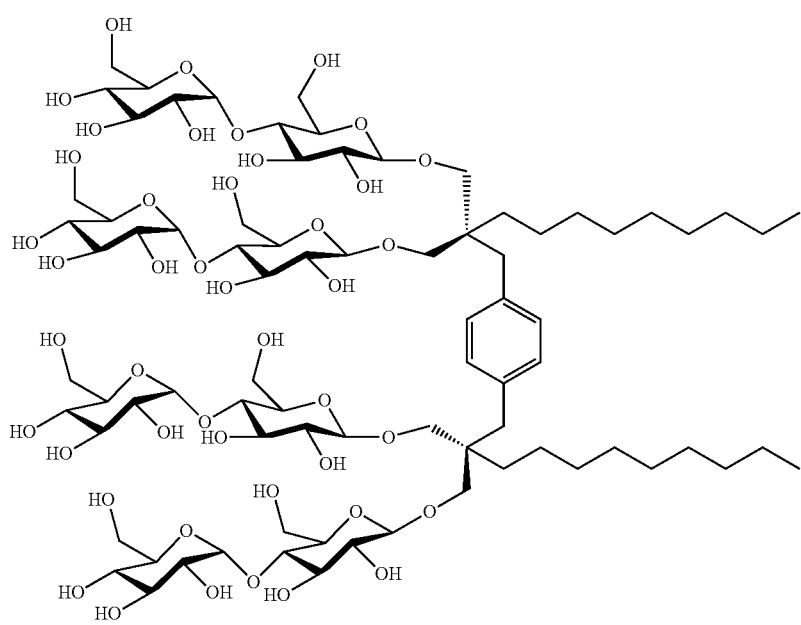

[Formula 5]
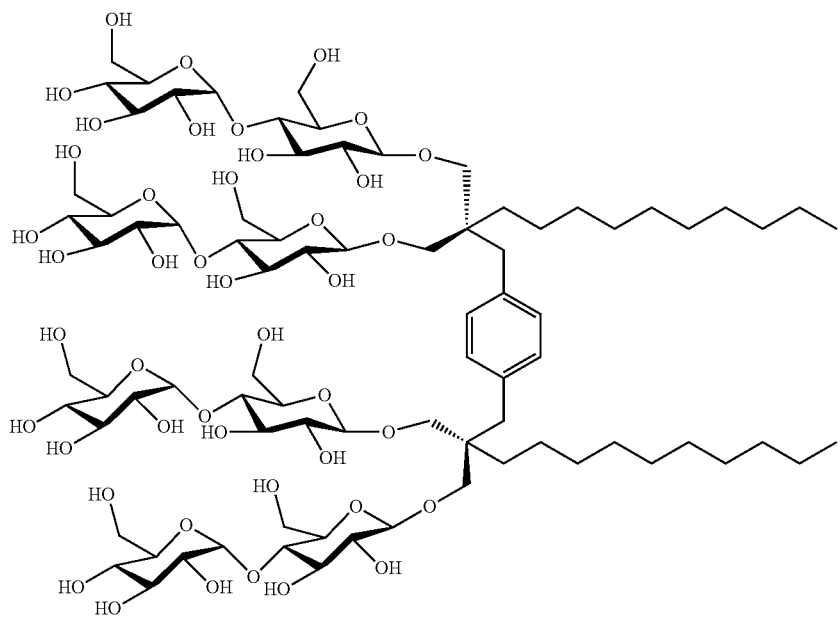
[Formula 6]
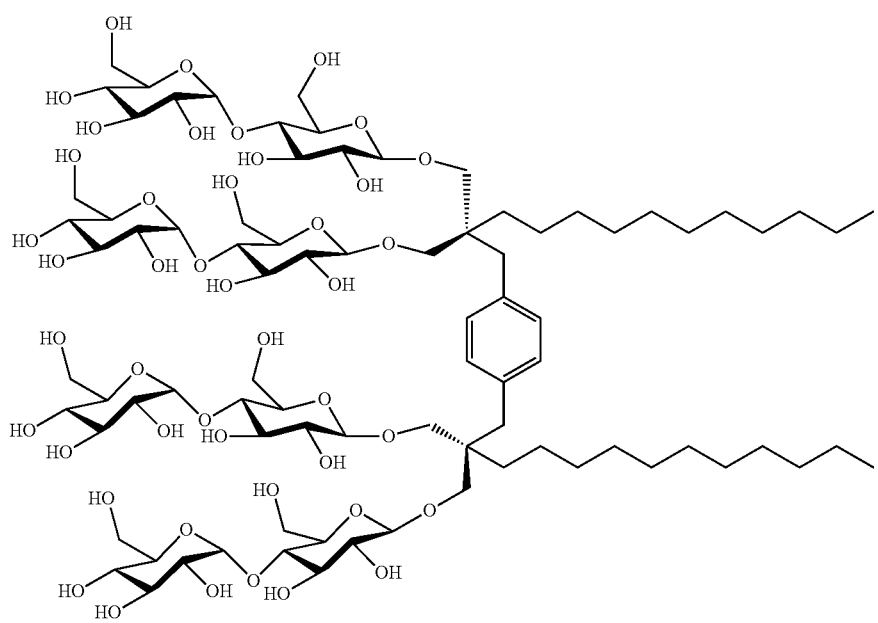

[Formula 7]
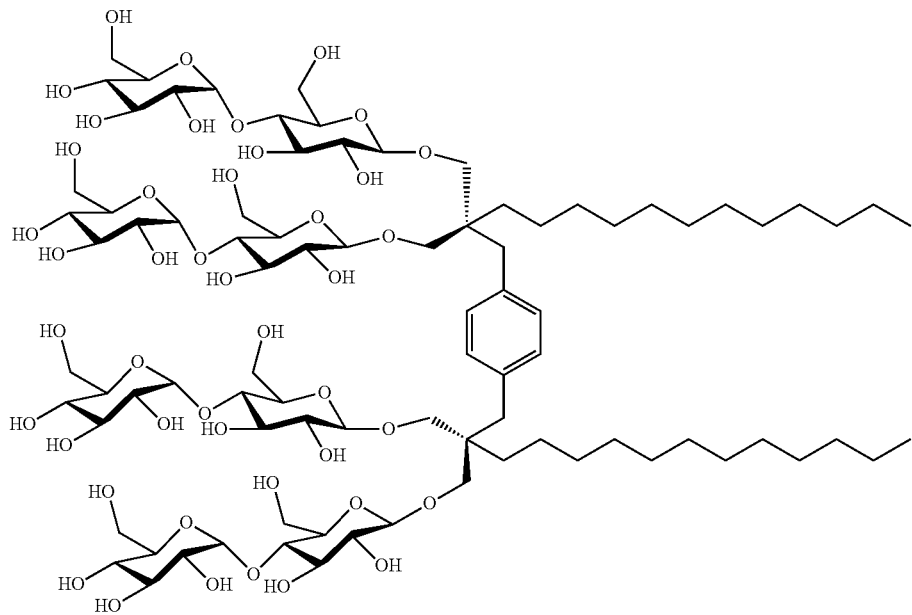
[Formula 8]
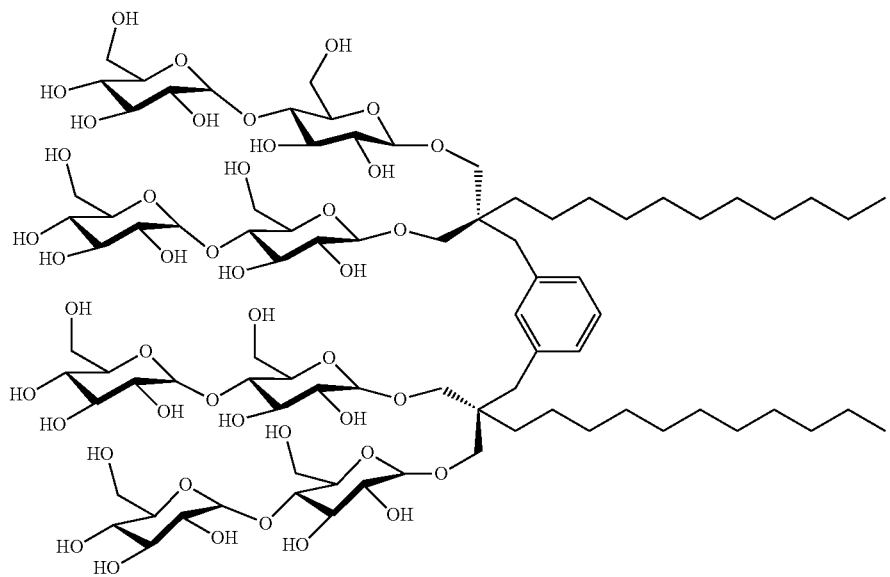

[Formula 9]
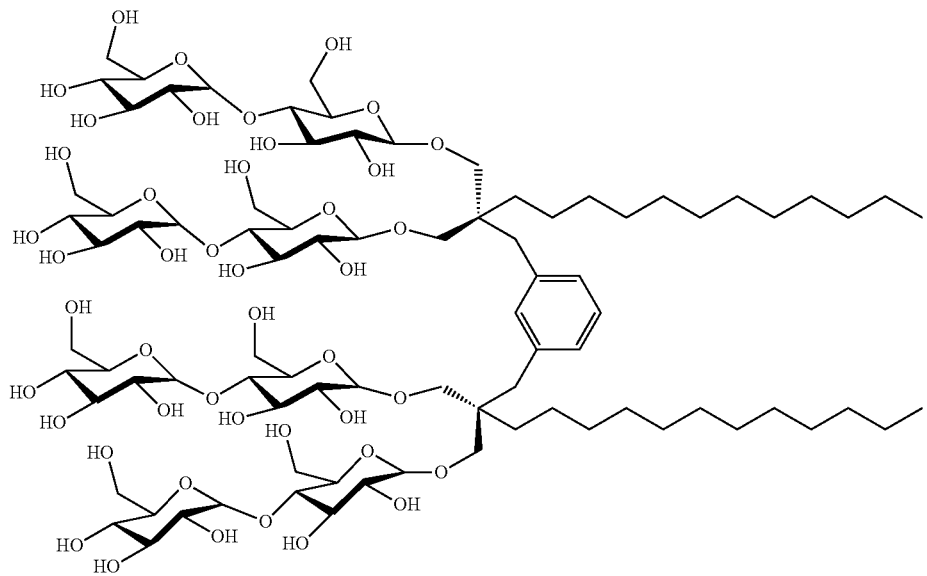
[Formula 10]
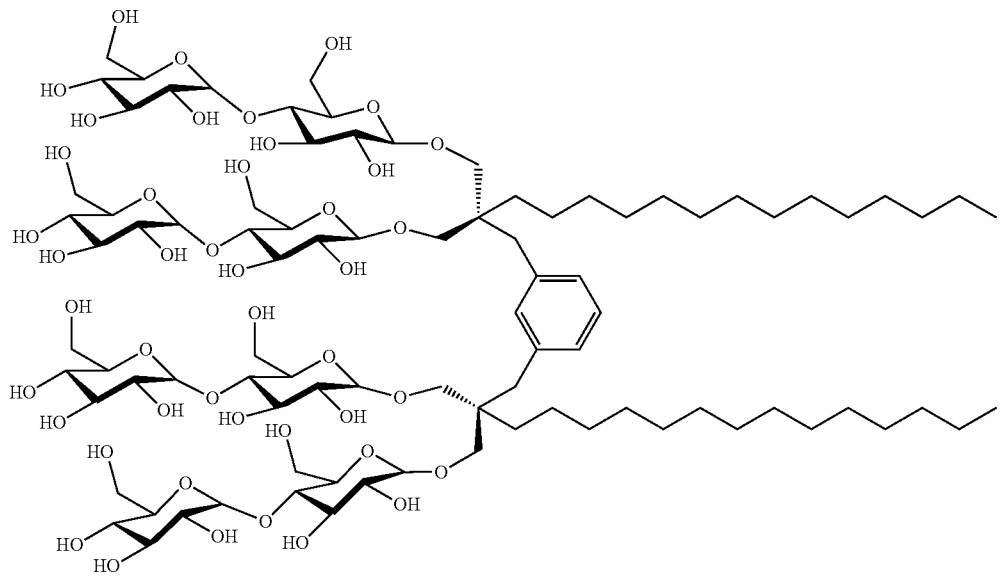

-continued
[Formula 11]
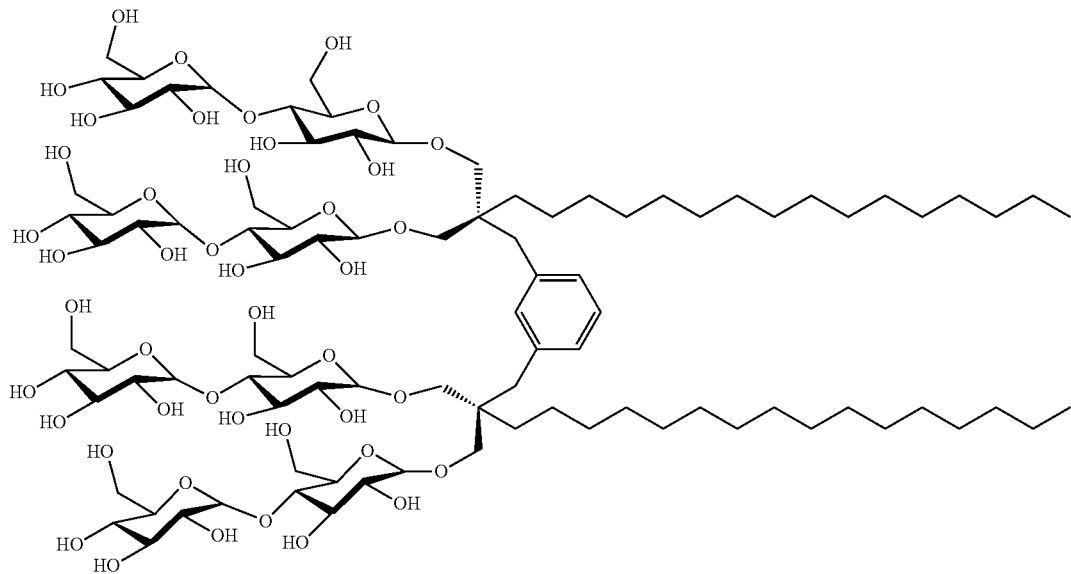
[Formula 12]
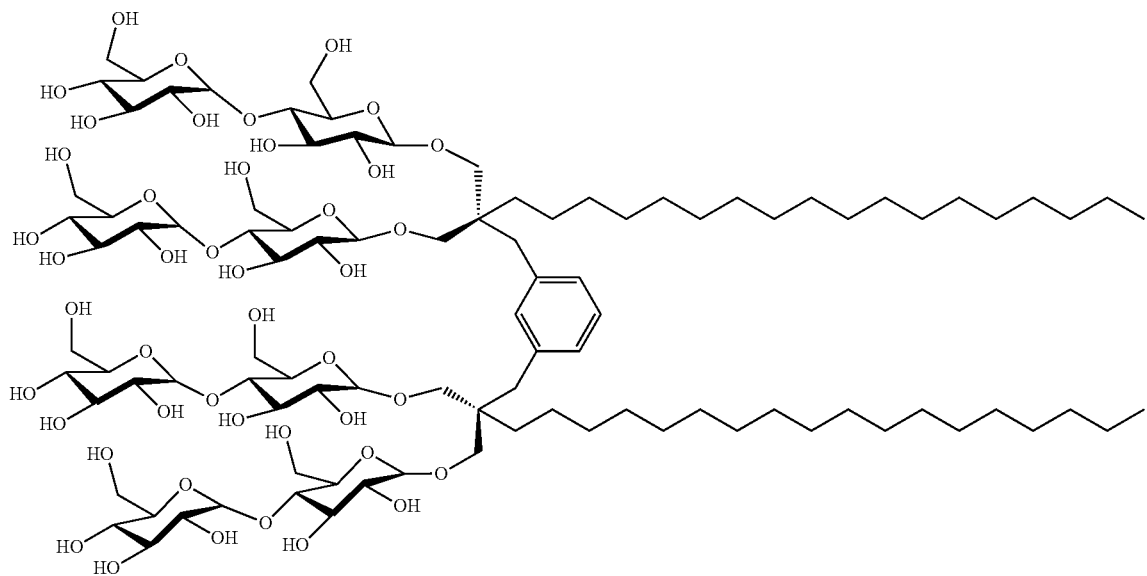

[Formula 13]
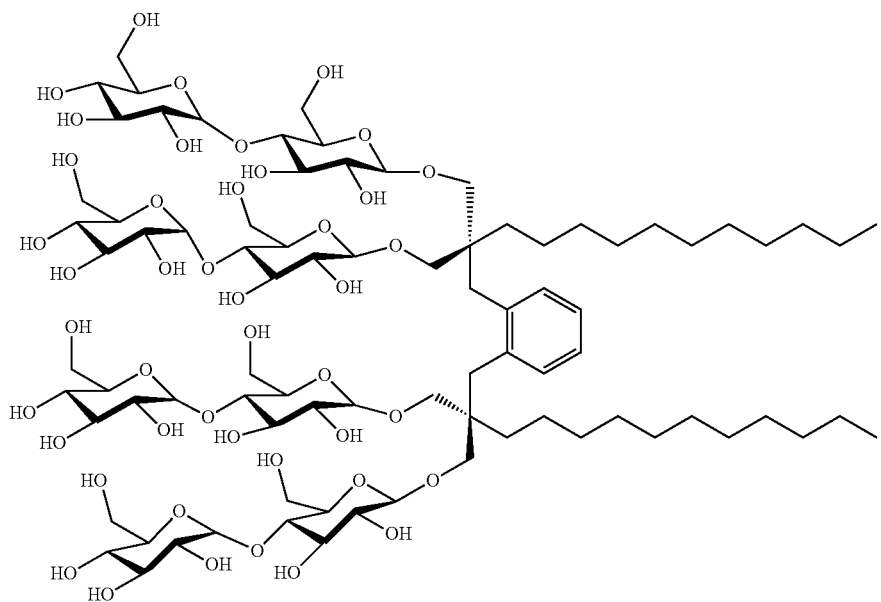
[Formula 14]
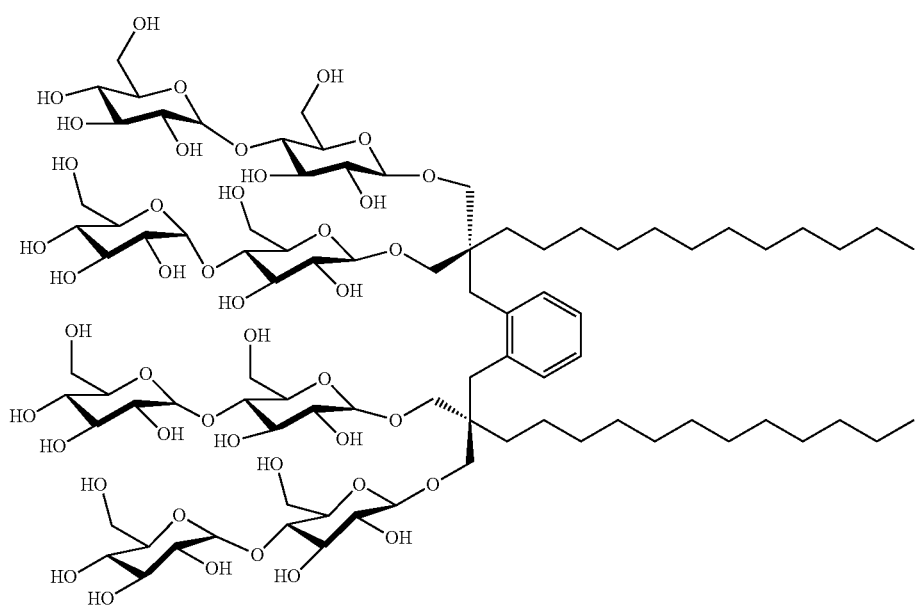

-continued
[Formula 15]
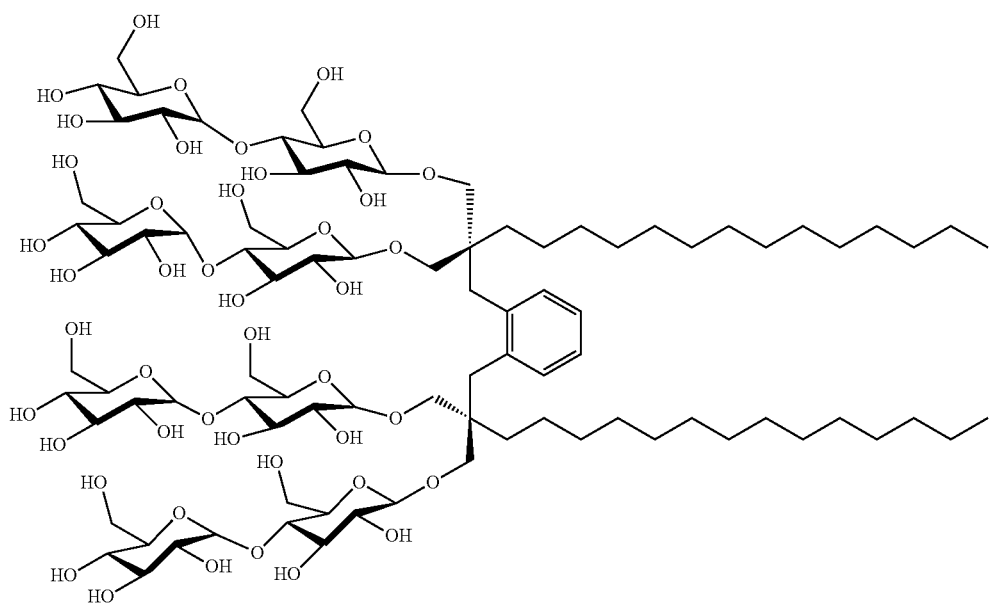
[Formula 16]
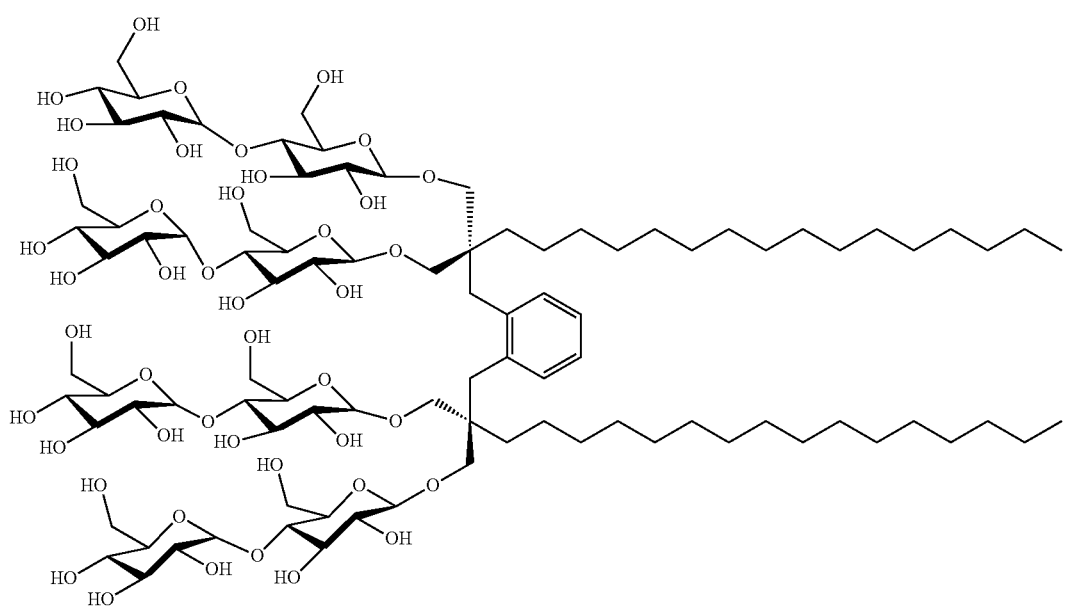

[Formual 17]
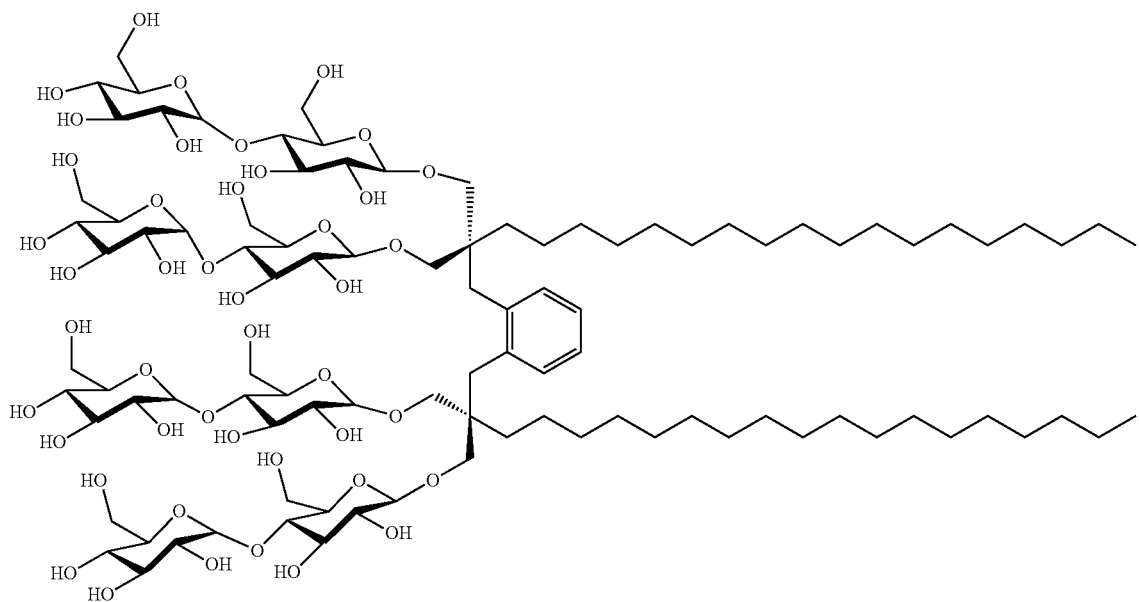
[Formula 18]
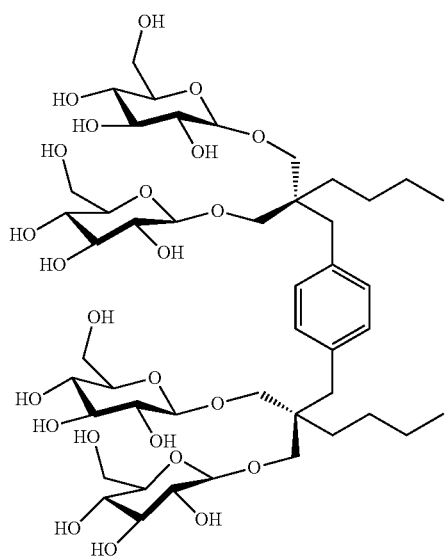
[Formula 19]
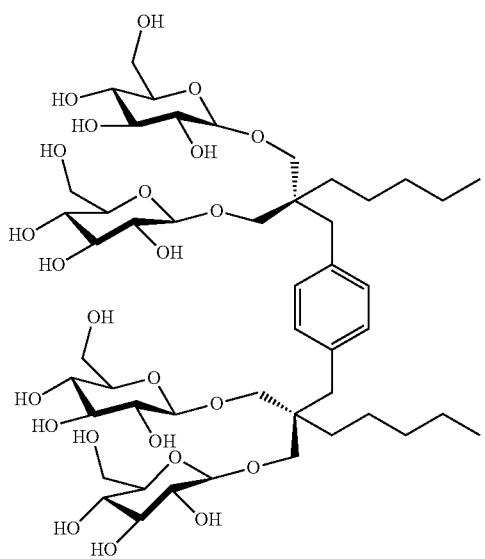

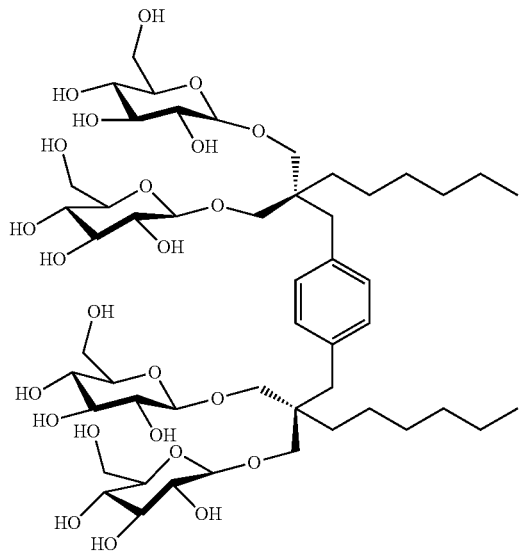

7. The compound of claim 1, wherein the compound is an amphiphilic molecule for extracting, solubilizing, stabilizing, crystallizing or analyzing a membrane protein.

8. The compound of claim 1, wherein the compound has a critical micelle concentration (CMC) of 0.1 to 1000 μM in an aqueous solution.

9. A composition for extracting, solubilizing, stabilizing, crystallizing or analyzing a membrane protein, which includes the compound of claim 1.

10. The composition of claim 9, which is a micelle, a liposome, an emulsion or a nanoparticle.

11. A method for preparing the compound represented by Formula 1 below, the method comprising:
   1) introducing an alkyl group by performing monoalkylation on diethyl malonate;
   2) introducing a xylene linker by coupling the product of step 1) with bis(bromomethyl)benzene;
   3) reducing an ester functional group of the product of step 2) into an alcohol functional group;
   4) introducing a protective group-attached saccharide by performing glycosylation on the product of step 3); and
   5) performing deprotection on the product of step 4):

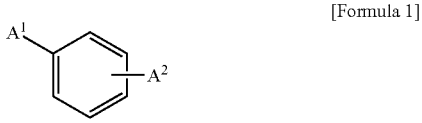

[Formula 1]

where the position of $A^2$, relative to $A^1$, is ortho, meta or para;
$A^1$ and $A^2$ are the same or different and each independently represented by Formula 2 below;

[Formula 2]

$R^1$ is a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;

$X^1$ and $X^2$ are each independently a saccharide linked by an oxygen atom; and the symbol * in Formula 2 may represent a part linked to the core structure of Formula 1.

12. A method for extracting, solubilizing, stabilizing, crystallizing or analyzing a membrane protein, the method comprising:
   treating a membrane protein with the compound represented by Formula 1 below in an aqueous solution:

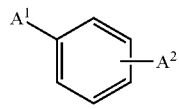

[Formula 1]

where the position of $A^2$, relative to $A^1$, is ortho, meta or para;
$A^1$ and $A^2$ are the same or different and each independently represented by Formula 2 below;

[Formula 2]

$R^1$ is a substituted or unsubstituted $C_3$-$C_{26}$ alkyl group, a substituted or unsubstituted $C_3$-$C_{26}$ cycloalkyl group, or a substituted or unsubstituted $C_3$-$C_{26}$ aryl group;

$X^1$ and $X^2$ are each independently a saccharide linked by an oxygen atom; and the symbol * in Formula 2 may represent a part linked to the core structure of Formula 1.

13. The method of claim 12, wherein the membrane protein is a boron transporter (Bor1), a leucine transporter (LeuT), melibiose permease (MelB), a human $\beta_2$ adrenergic receptor ($\beta_2$AR) or a combination of two or more thereof.

* * * * *